(12) United States Patent
Ging et al.

(10) Patent No.: US 7,878,199 B2
(45) Date of Patent: Feb. 1, 2011

(54) DISPOSABLE MASK SYSTEM

(75) Inventors: Anthony Michael Ging, Vancouver (CA); David John Worboys, Belrose (AU); Gregoy Scott Smart, Randwick (AU); Muditha Pradeep Dantanarayana, Cherrybrook (AU); John Michael Snow, Cremorne (AU); Philip Thomas Stallard, Denistone East (AU)

(73) Assignee: ResMed Limited, Bella Vista (AU)

( * ) Notice: Subject to any disclaimer, the term of this patent is extended or adjusted under 35 U.S.C. 154(b) by 217 days.

(21) Appl. No.: 11/952,167

(22) Filed: Dec. 7, 2007

(65) Prior Publication Data

US 2008/0087287 A1 Apr. 17, 2008

Related U.S. Application Data

(63) Continuation of application No. 11/027,689, filed on Jan. 3, 2005.

(60) Provisional application No. 60/533,229, filed on Dec. 31, 2003, provisional application No. 60/571,488, filed on May 17, 2004, provisional application No. 60/588,341, filed on Jul. 16, 2004, provisional application No. 60/619,022, filed on Oct. 18, 2004.

(51) Int. Cl.
*A62B 18/08* (2006.01)
*A62B 7/10* (2006.01)
*A62B 18/02* (2006.01)
*A62B 18/10* (2006.01)
*A62B 9/02* (2006.01)

(52) U.S. Cl. .......................... 128/206.26; 128/206.12; 128/206.15; 128/206.18; 128/206.21; 128/206.23; 128/206.24; 128/206.27; 128/206.28; 128/207.11; 128/207.12; 128/207.13; 128/205.27; 128/205.24

(58) Field of Classification Search ............. 128/206.12, 128/206.15, 206.18, 206.21, 206.23, 206.24, 128/206.26, 206.27, 206.28, 207.11, 207.12, 128/207.13, 205.27, 205.24, 912
See application file for complete search history.

(56) References Cited

U.S. PATENT DOCUMENTS

| 2,097,676 | A | 11/1937 | Shindel et al. |
| 2,292,568 | A | 8/1942 | Kanter et al. |
| 2,823,671 | A | 2/1958 | Garelick |
| 2,928,387 | A | 3/1960 | Layne |

(Continued)

FOREIGN PATENT DOCUMENTS

AU 59430/94 A 10/1995

(Continued)

OTHER PUBLICATIONS

Supplementary European Search Report mailed May 7, 2009 in European Application No. 04802114.1 (6 pages).

(Continued)

*Primary Examiner*—Patricia M Bianco
*Assistant Examiner*—Nihir Patel
(74) *Attorney, Agent, or Firm*—Nixon & Vanderhye P.C.

(57) ABSTRACT

A mask system includes a frame, cushion, cushion clip, swivel elbow, headgear and/or headgear clips that are configured for use in a clinical or hospital environment. One or more components of the mask system are configured to promote single patient use, e.g., by providing an age indicator and/or preventing disassembly and/or cleaning, etc.

27 Claims, 49 Drawing Sheets

U.S. PATENT DOCUMENTS

| | | | |
|---|---|---|---|
| 4,069,516 A | 1/1978 | Watkins | |
| 4,437,462 A | 3/1984 | Piljay et al. | |
| 4,971,051 A | 11/1990 | Toffolon | |
| 5,069,205 A | 12/1991 | Urso | |
| 5,205,832 A | 4/1993 | Tuman | |
| 5,245,993 A | 9/1993 | McGrady et al. | |
| 5,291,880 A | 3/1994 | Almovist et al. | |
| 5,438,981 A | 8/1995 | Starr et al. | |
| 5,441,046 A | 8/1995 | Starr | |
| 5,657,493 A | 8/1997 | Ferrero et al. | |
| 5,660,174 A | 8/1997 | Jacobelli | |
| 5,662,101 A | 9/1997 | Ogden et al. | |
| 5,884,624 A | 3/1999 | Barnett et al. | |
| 5,918,598 A | 7/1999 | Belfer et al. | |
| 5,921,239 A | 7/1999 | McCall et al. | |
| 5,924,420 A | 7/1999 | Reischel et al. | |
| 6,192,886 B1 | 2/2001 | Rudolph | |
| 6,199,219 B1 | 3/2001 | Silken et al. | |
| D443,355 S | 6/2001 | Gunaratnam et al. | |
| 6,374,826 B1 | 4/2002 | Gunaratnam et al. | |
| 6,412,487 B1 | 7/2002 | Gunaratnam et al. | |
| 6,439,230 B1 | 8/2002 | Gunaratnam et al. | |
| 6,513,526 B2 | 2/2003 | Kwok et al. | |
| 6,530,373 B1 | 3/2003 | Patron | |
| 6,615,830 B1 | 9/2003 | Serowski et al. | |
| 6,631,718 B1 | 10/2003 | Lovell | |
| D493,521 S | 7/2004 | Guney | |
| 6,851,425 B2 | 2/2005 | Jaffre | |
| 7,185,652 B2 | 3/2007 | Gunaratnam et al. | |
| 7,210,481 B1 | 5/2007 | Lovell et al. | |
| 7,621,274 B2 | 11/2009 | Sprinkle et al. | |
| 2002/0096176 A1 | 7/2002 | Gunaratnam et al. | |
| 2003/0075180 A1 | 4/2003 | Raje et al. | |
| 2003/0106557 A1 | 6/2003 | Viljanen et al. | |
| 2003/0178026 A1 | 9/2003 | Byram | |
| 2004/0025883 A1 | 2/2004 | Eaton | |
| 2004/0045551 A1 | 3/2004 | Eaton et al. | |
| 2004/0094157 A1* | 5/2004 | Dantanarayana et al. | 128/206.21 |
| 2004/0112384 A1 | 6/2004 | Lithgow et al. | |
| 2005/0011521 A1 | 1/2005 | Sprinkle et al. | |
| 2005/0022820 A1 | 2/2005 | Kwok et al. | |
| 2005/0076912 A1 | 4/2005 | Eifler et al. | |
| 2005/0126573 A1 | 6/2005 | Jaffre et al. | |
| 2005/0172969 A1 | 8/2005 | Ging et al. | |
| 2006/0076019 A1 | 4/2006 | Ho | |
| 2006/0096598 A1 | 5/2006 | Ho et al. | |
| 2006/0162729 A1 | 7/2006 | Ging et al. | |
| 2006/0196509 A1 | 9/2006 | Drew et al. | |

FOREIGN PATENT DOCUMENTS

| | | |
|---|---|---|
| EP | 0 958 841 A2 | 11/1999 |
| EP | 1027905 | 8/2000 |
| FR | 2727836 | 6/1996 |
| GB | 684788 | 12/1952 |
| GB | 704167 | 2/1954 |
| GB | 2293410 | 3/1996 |
| WO | WO 87/01950 | 4/1987 |
| WO | WO 97/20597 | 6/1997 |
| WO | WO 98/48878 | 11/1998 |
| WO | WO 2004/096332 A1 | 11/2004 |
| WO | WO 2005/002656 | 1/2005 |

OTHER PUBLICATIONS

European Search Report completed Jan. 27, 2006 in EP Application No. 05 02 6584.2.

International Search Report, PCT/AU2004/001760 (Jan. 2004).

International Search Report, PCT/AU2004/001813 (Jan. 2004).

International Preliminary Report on Patentability, PCT/AU2004/001813, Jul. 3, 2006.

International Preliminary Report on Patentability, PCT/AU2004/001760, Jul. 3, 2006.

* cited by examiner

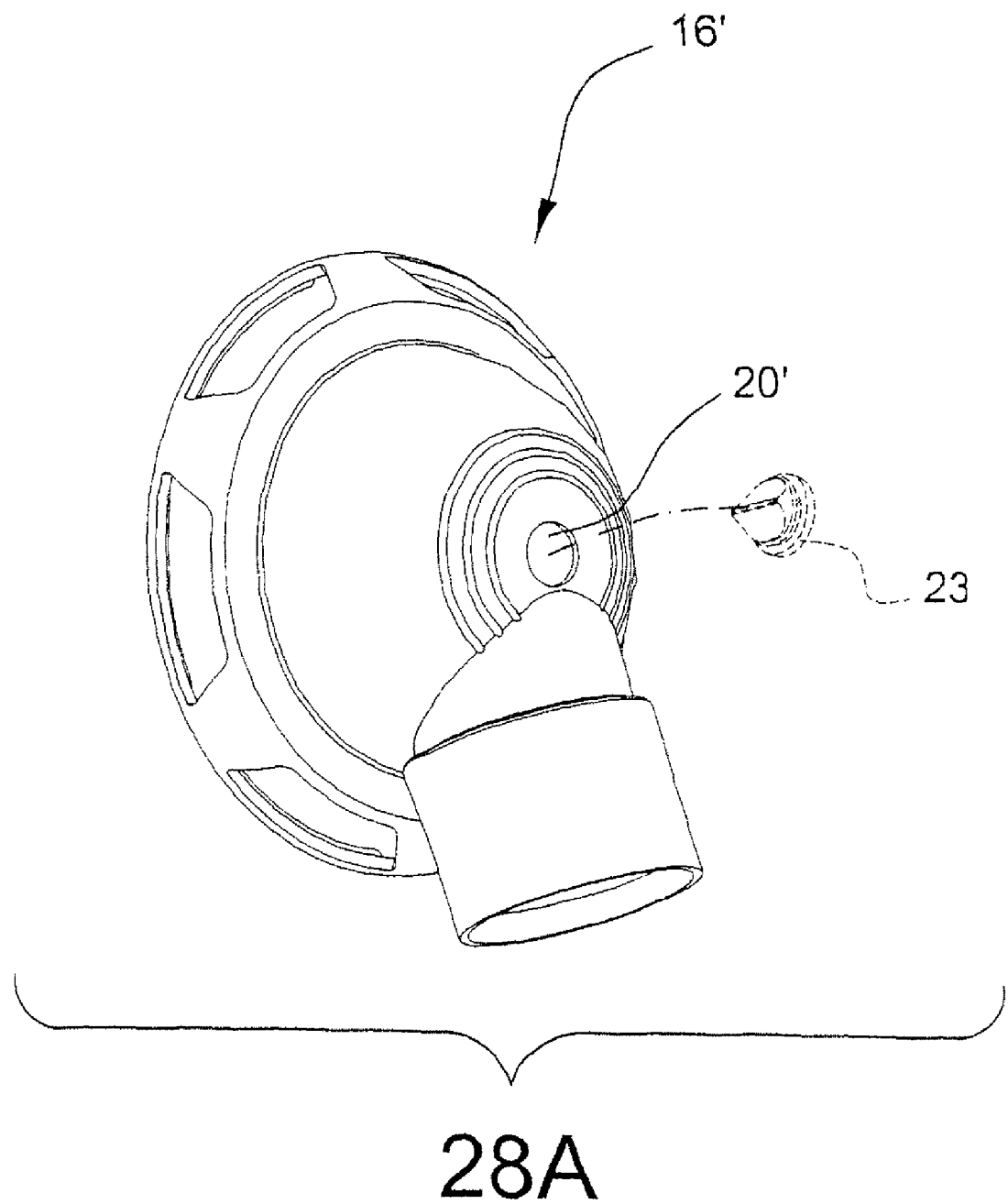

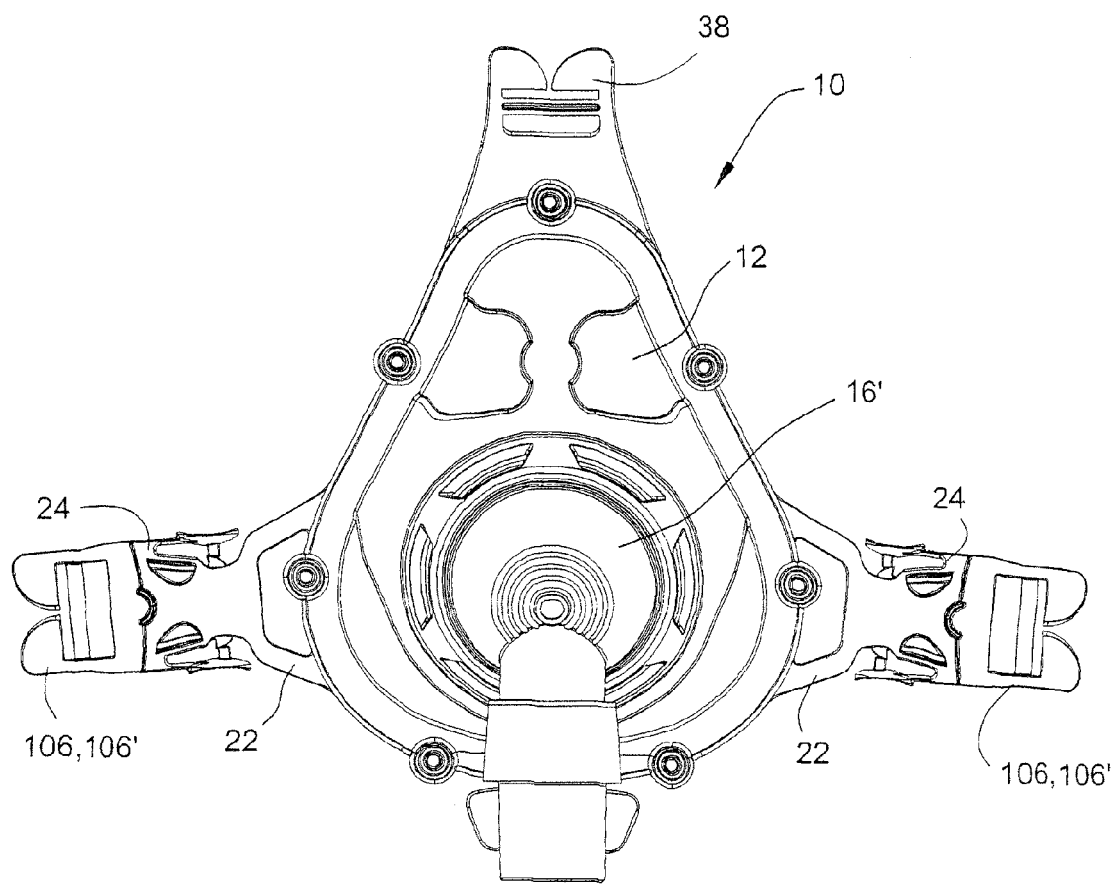
Fig. 31-A

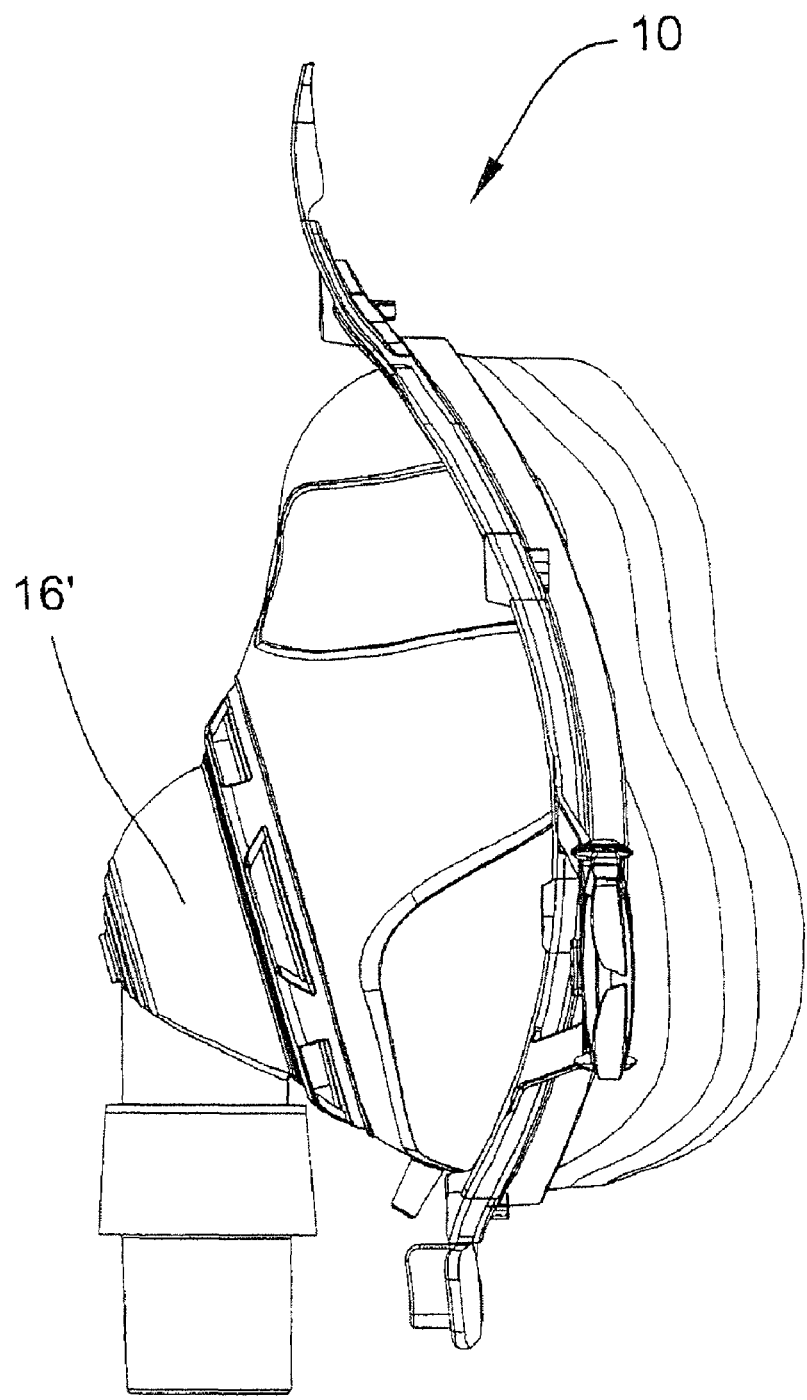
Fig. 31-B

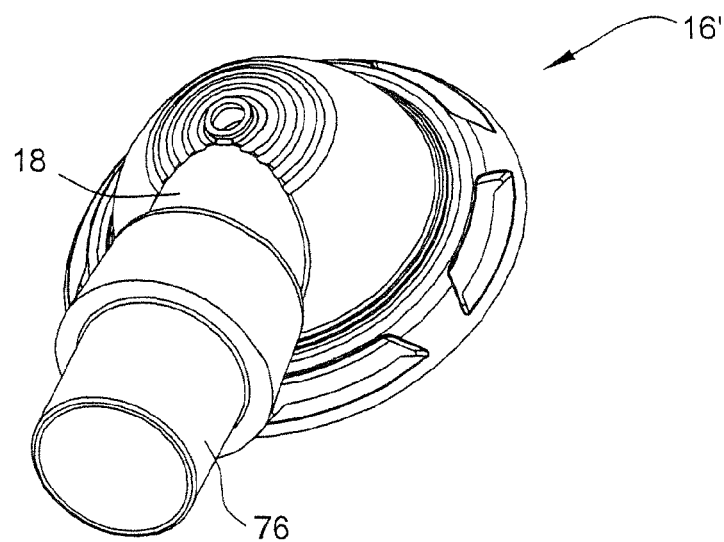
Fig. 31-C
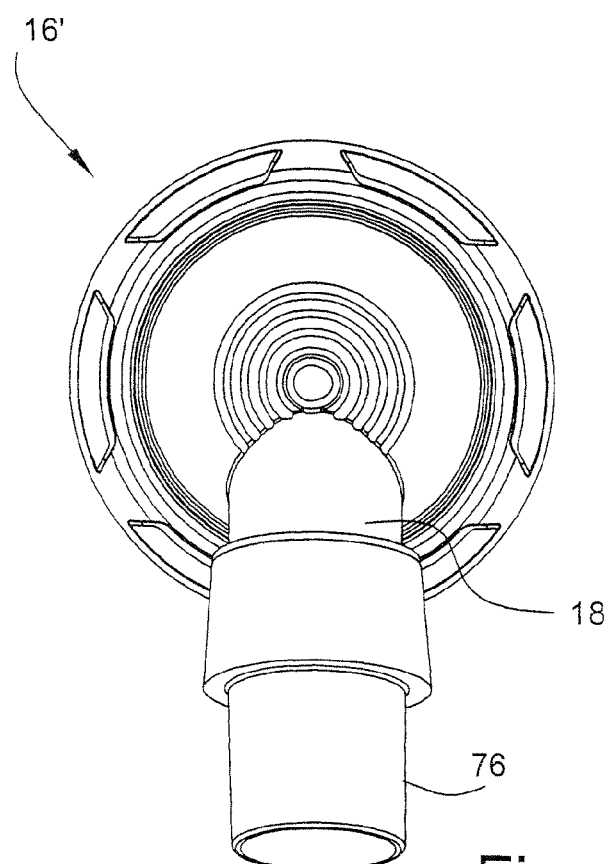
Fig. 31-D

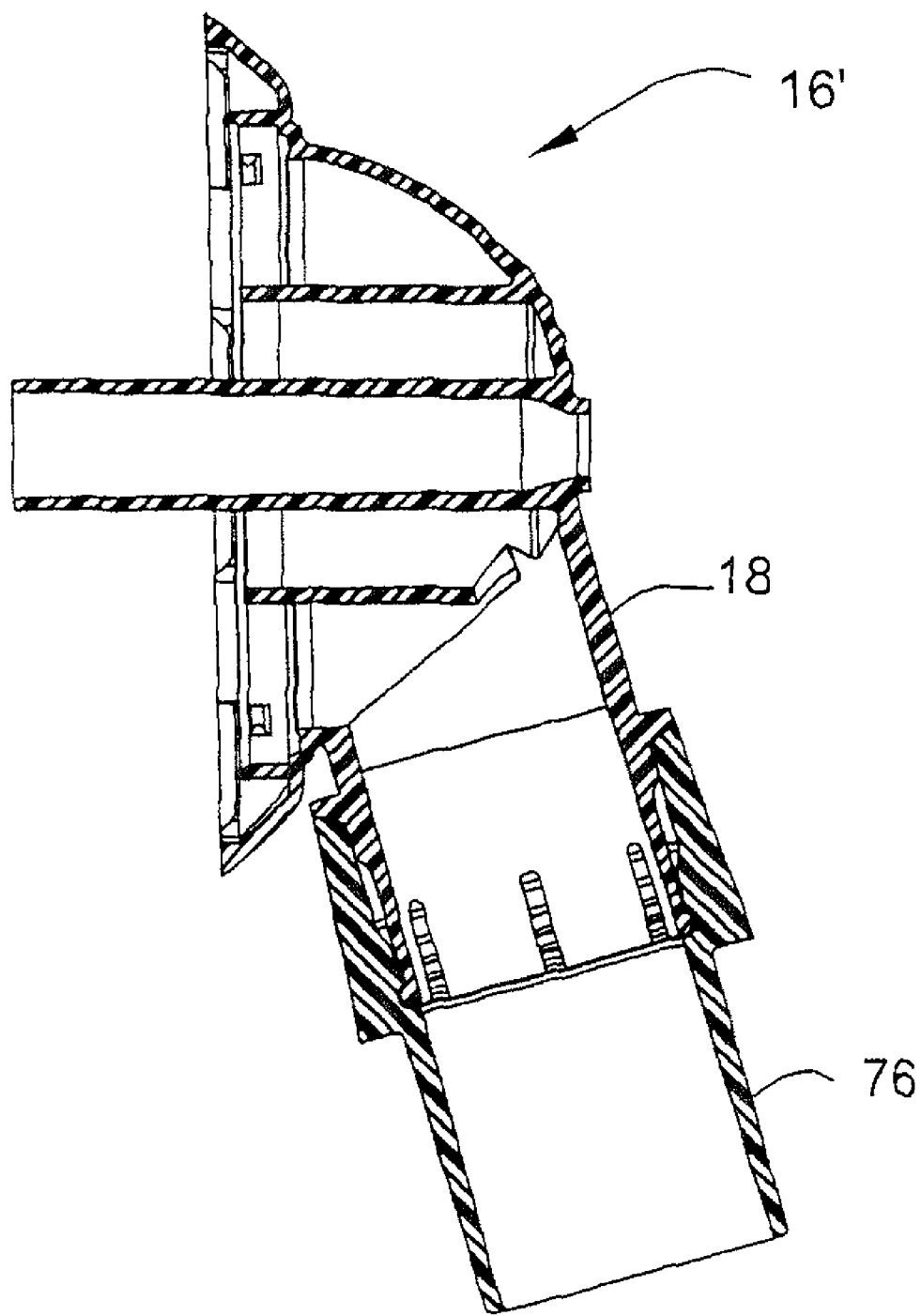
Fig. 31-E

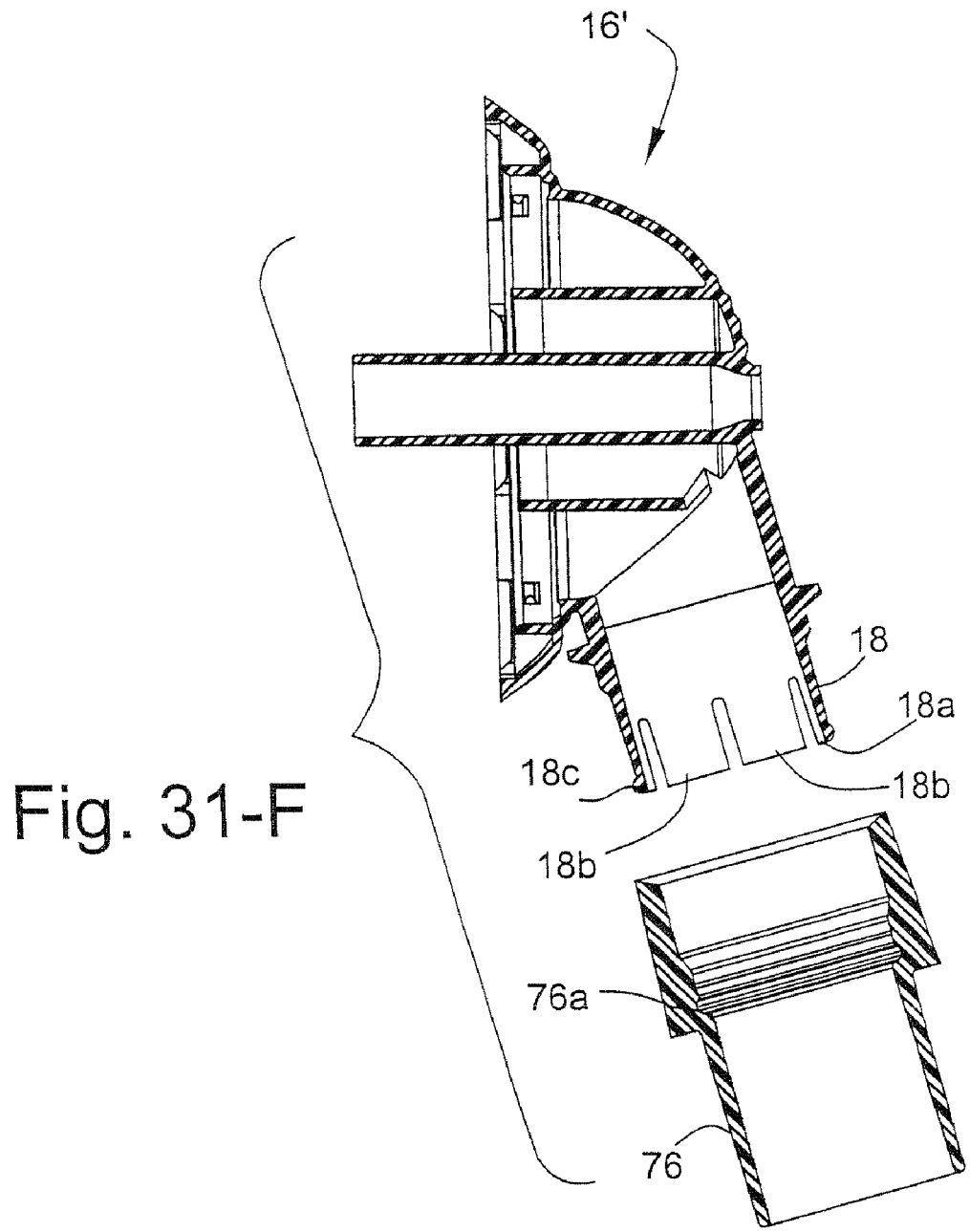
Fig. 31-F

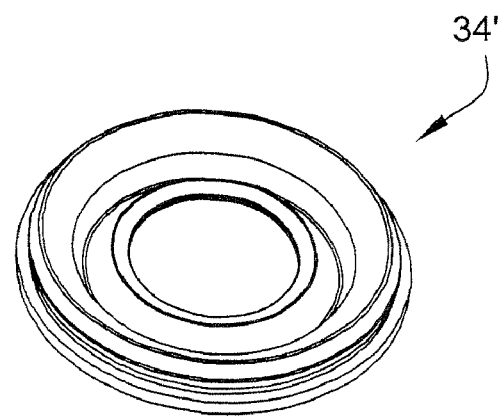
Fig. 31-G
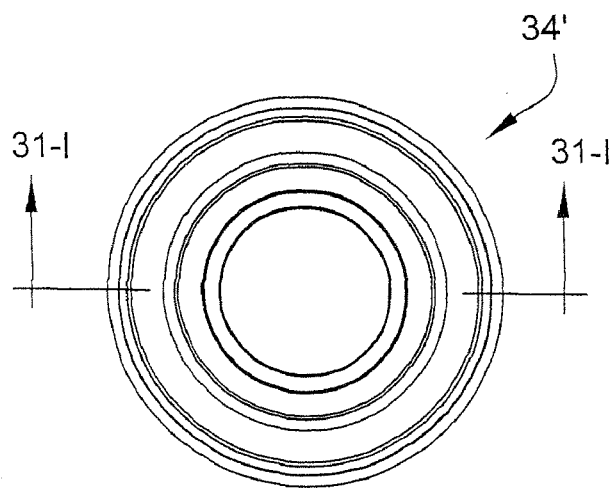
Fig. 31-H
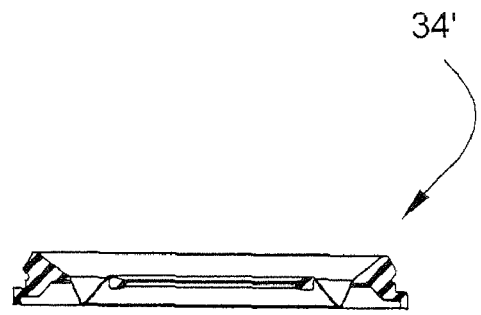
Fig. 31-I

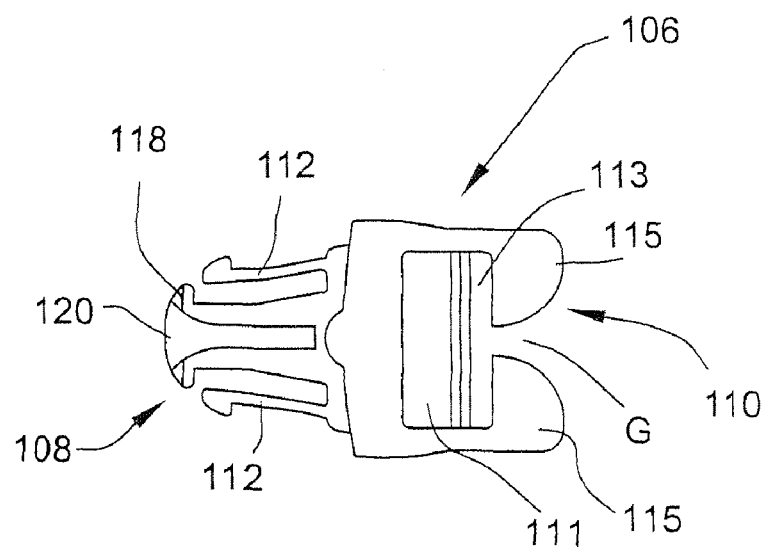
Fig. 32
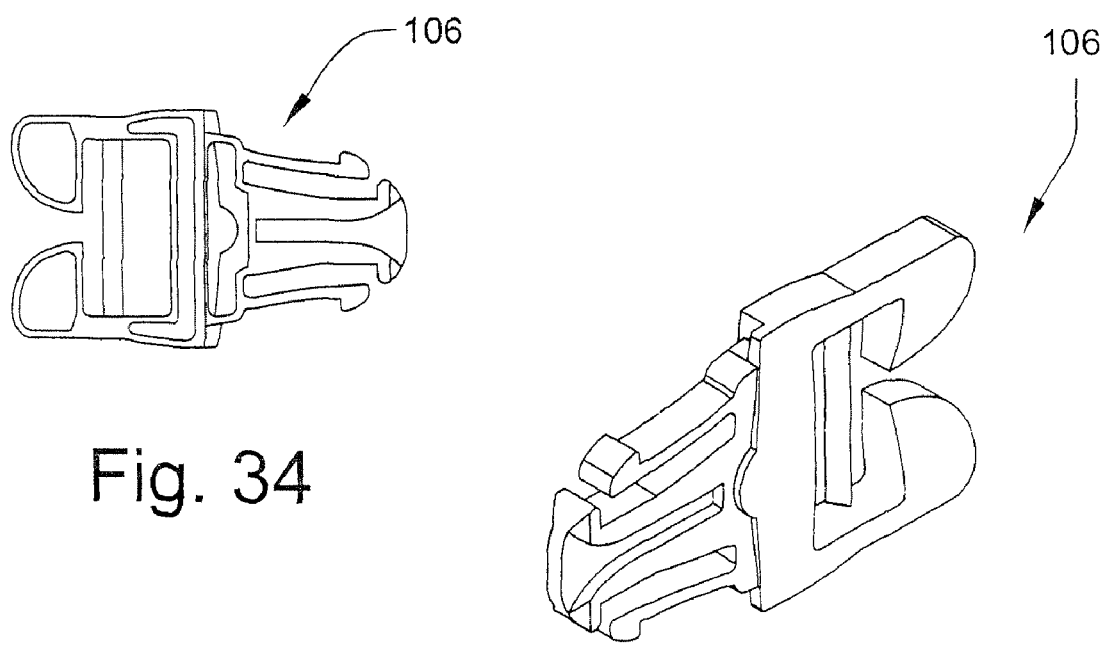
Fig. 34
Fig. 33

DISPOSABLE MASK SYSTEM

CROSS-REFERENCE TO APPLICATIONS

This application is a continuation of U.S. Ser. No. 11/027,689, filed Jan. 3, 2005 which claims the benefit of U.S. Provisional Application Nos. 60/533,229, filed Dec. 31, 2003, 60/571,488, filed May 17, 2004, 60/588,341, filed Jul. 16, 2004, and 60/619,022, filed Oct. 18, 2004, each incorporated herein by reference in its entirety.

BACKGROUND OF THE INVENTION

1. Field of the Invention

The present invention relates to a disposable mask system for use with patients, e.g., adult patients, for the treatment of obstructive sleep apnea (OSA) or the provision of non-invasive positive pressure ventilation (NIPPV) support using continuous positive airway pressure (CPAP), bi-level, or other pressure support ventilators. The mask is intended for single patient, short-term use having a life span, e.g., of about 7-14 days. Preferably, the mask is only usable for up to 7 days.

2. Description of Related Art

ResMed's Mirage® Disposable Full Face mask is formed of a frame with a double wall silicone cushion. The cushion, elbow, and/or vent components can be disassembled from the frame. While this mask performs strongly for seal and comfort, it may not display characteristics that are most amenable for hospital and clinical use, which can differ from the characteristics most suitable for home or other uses.

Another related art disposable mask is ResMed's Disposable Nasal Mask® which has a PVC bubble cushion and a styrene frame. The Image3 Disposable Full Face Mask from Respironics has a frame and a silicone cushion. Yet another full face disposable mask is the Respironics Spectrum Disposable Full Face Mask that has a single PVC cushion and a frame. The Med Series 2100 Disposable Full Face Mask has a PVC frame and a foam cushion. Still another mask is the "Performa Trak," a single use full face mask from Respironics.

These related art masks do not provide fully adequate and/or optimum solutions for use of mask systems in a hospital or clinical environment. For example, these masks exhibit one or more properties that are typically associated with re-useable masks. Therefore, these masks can be accidentally re-used in a manner that could be dangerous to the patient, e.g., the risk of spread of germs, etc.

BRIEF SUMMARY OF THE INVENTION

One aspect of the invention is to provide a mask system which is at least partially capable of overcoming the problems of the related art.

Another aspect of the invention is to provide a disposable mask which has a useful life of either a single use or can be used over a short period of time, e.g., 7-10 days or more. Preferably, the mask can be used only up to 7 days.

Another aspect of the invention is to provide a mask which provides an indication, e.g., a visual indication, that the mask has been used once, more than once or more than the recommended number of times or period of time.

Yet another aspect of the invention is to provide a mask assembly which is difficult to disassemble without breaking, thereby discouraging multiple use and preventing removal of safety components such as an anti-asphyxia valve.

Still another aspect of the invention is to provide a mask which is disposable and/or which satisfies the needs of the clinical or hospital environment, which often differ from the needs of a mask used in a home environment.

In another aspect, the mask is designed to be fitted by a clinician or nurse.

Another aspect of the invention is to provide a low cost mask with high differentiation between disposable and reusable products, in terms of functionality, aesthetics and/or durability.

These and other aspects of the present invention are described in or apparent from the following description of preferred embodiments.

BRIEF DESCRIPTION OF THE DRAWINGS

FIGS. 28A-1-28A-2 illustrate views of an elbow according to still another embodiment of the present invention;

FIGS. 31-A to 31-I illustrate a mask assembly, elbow, swivel and/or anti-asphyxia valve member in accordance with an embodiment of the present invention;

FIG. 32 is a front view of a headgear clip according to the present invention;

FIG. 33 is a perspective view thereof;

FIG. 34 is a rear view thereof;

DETAILED DESCRIPTION OF PREFERRED EMBODIMENTS

Figure 1:
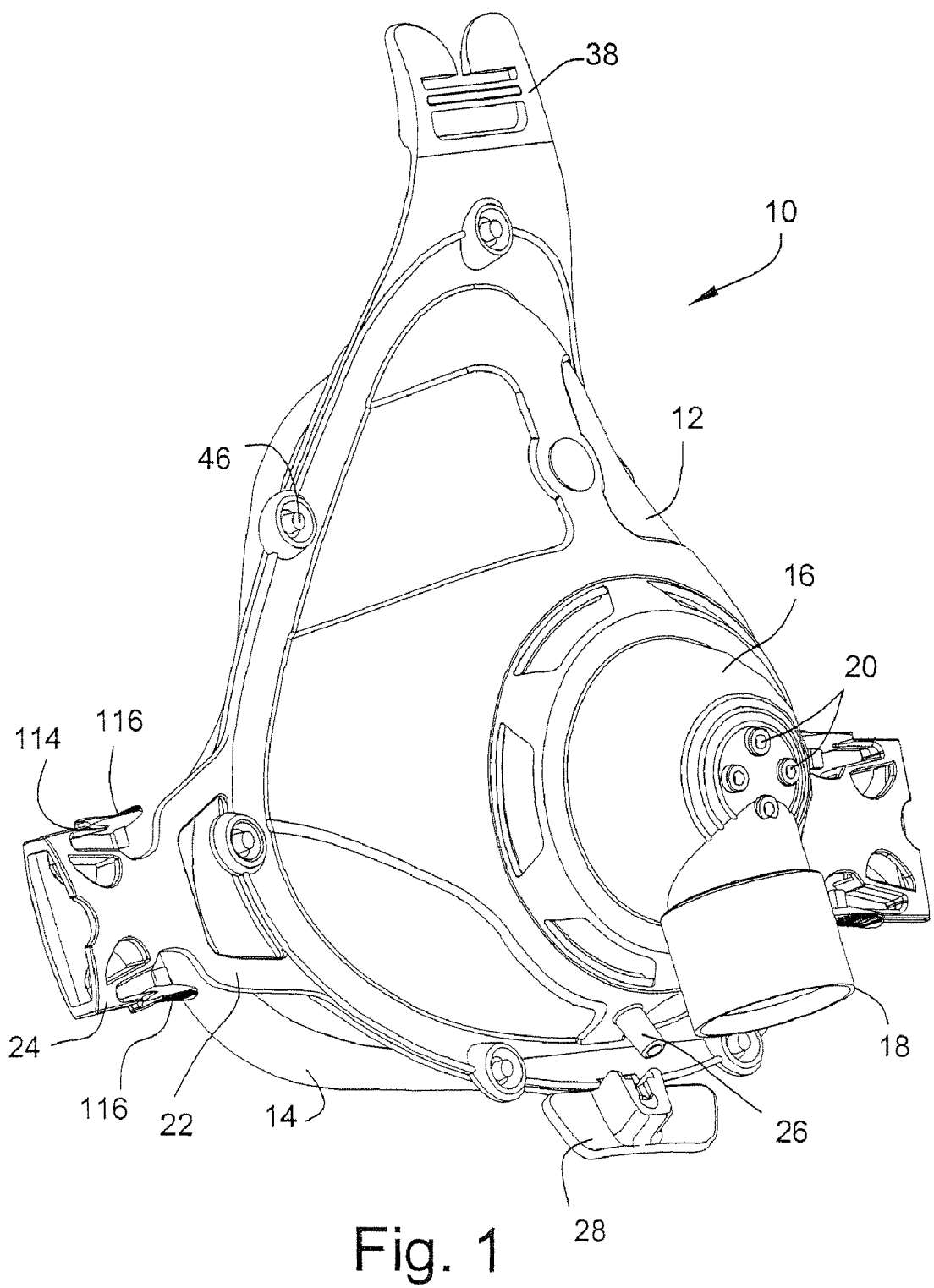
FIG. 1 is a perspective view from the front left side illustrating a first preferred embodiment of the present invention.

Preferred embodiments of the present invention will be described in relation to the appended figures, in which like reference numerals refer to like parts.

FIG. 1 shows a mask assembly 10 which includes a frame 12 in the form of a shell, and a cushion 14 that is provided, e.g., attached, to the frame 12. A swivel elbow 16 is rotatably coupled or provided to the frame 12. The swivel elbow 16 includes an inlet conduit 18 that receives pressurized breathable gas from a suitable source of pressurized air, as is known in the art. The swivel elbow 16 includes one or more apertures 20 which serve to continually wash out exhaled $CO_2$ gas from a breathing chamber formed by the frame 12 and the cushion 14. The frame 12 includes at least a pair of lateral outriggers 22 which support connector clip receptacles 24 designed to receive connector clips (see, e.g., FIGS. 32-34) associated with headgear (see, e.g., FIGS. 35-40). The frame 12 includes a centrally located upper extension 38 including various structure intended to interlock with a headgear strap of headgear.

Frame 12 also includes at least one port 26 that allows for the introduction of a pressure monitoring probe, or a separate gas such as oxygen ($O_2$) to be introduced (via a tube) into the interior of the breathing chamber. The port 26 may be suitably covered by a port cap 28 which is shown in the disconnected position in FIG. 1. As described and shown below, the port cap 28 may be formed as an integral part of the cushion 14.

Figure 2:
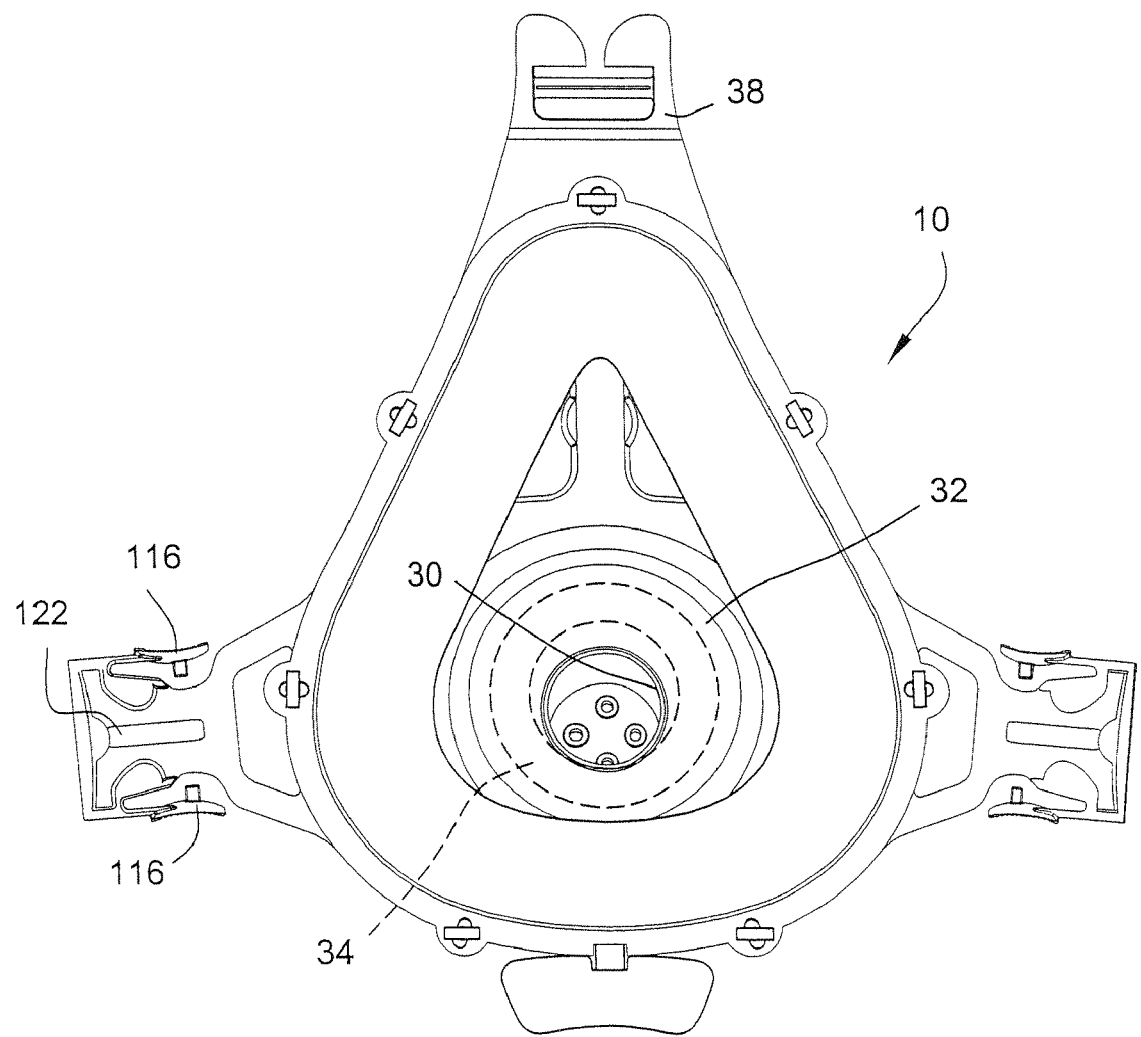
FIG. 2 is a rear view thereof.

FIG. 2 illustrates a patient's side or rear view of the mask assembly 10. The face contacting portion of the cushion 14 preferably includes a double layer, spaced wall configuration as described in U.S. Pat. No. 6,513,526 assigned to ResMed Limited and incorporated herein by reference in its entirety. However, other cushion configurations such as single or triple layer cushion configurations could also be employed without departing from the spirit and scope of the present invention. In addition, the cushion can be made of silicone, foam, gel, etc., or combinations thereof.

FIG. 2 also illustrates an aperture 30 which communicates the inlet conduit 18 of swivel elbow 16 to the breathing chamber. Surrounding aperture 30 is a generally circular support 32 formed as part of the frame 12. The support 32 forms a surface for an anti-asphyxia valve membrane 34 (shown in detail in FIGS. 29-31). As described in more detail below, the anti-asphyxia valve membrane 34 is positioned between the support 32 and the swivel elbow 16.

Figure 3:
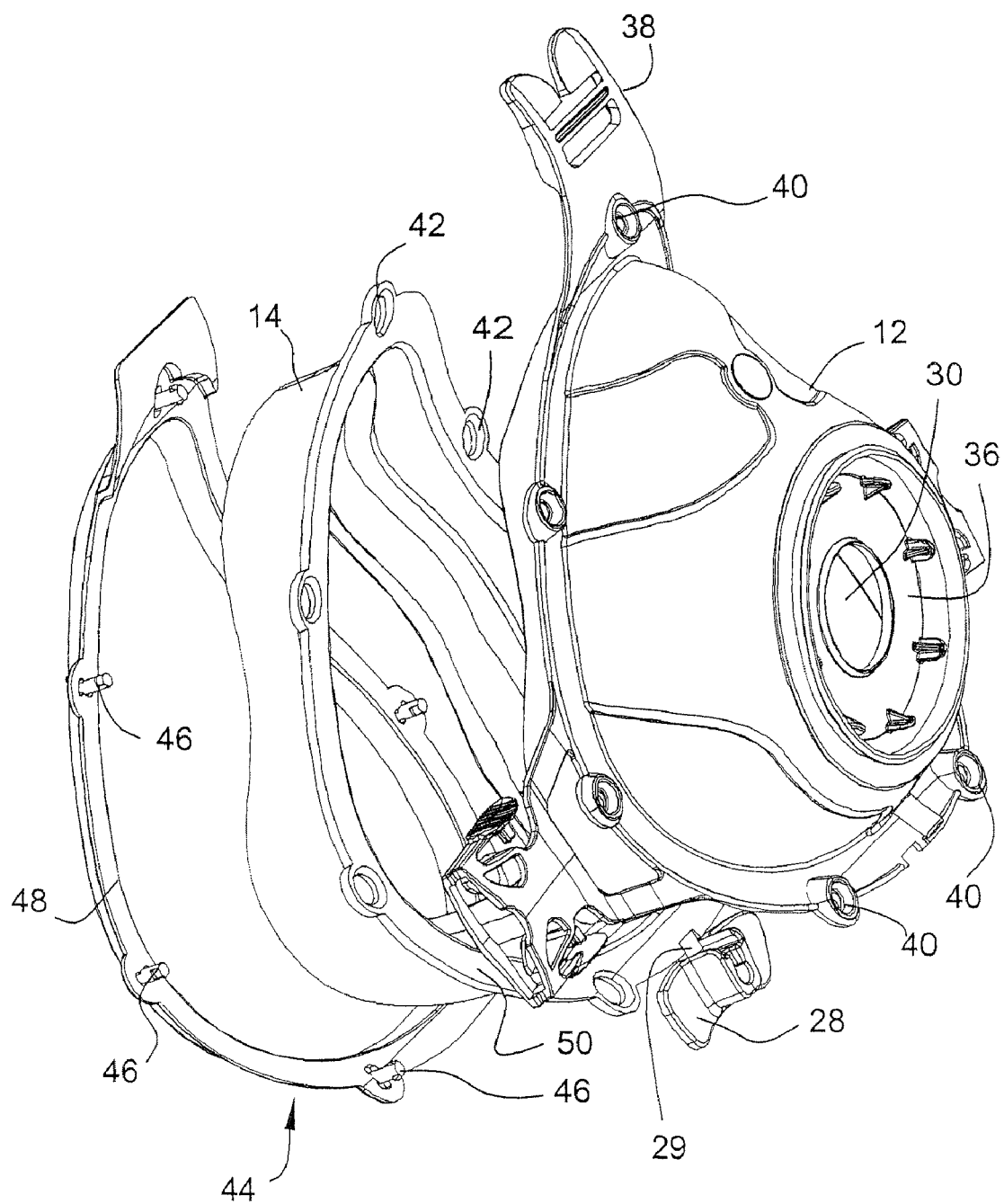
FIG. 3 is a front perspective exploded view of a portion of the assembly shown in FIG. 1.
Figure 4:
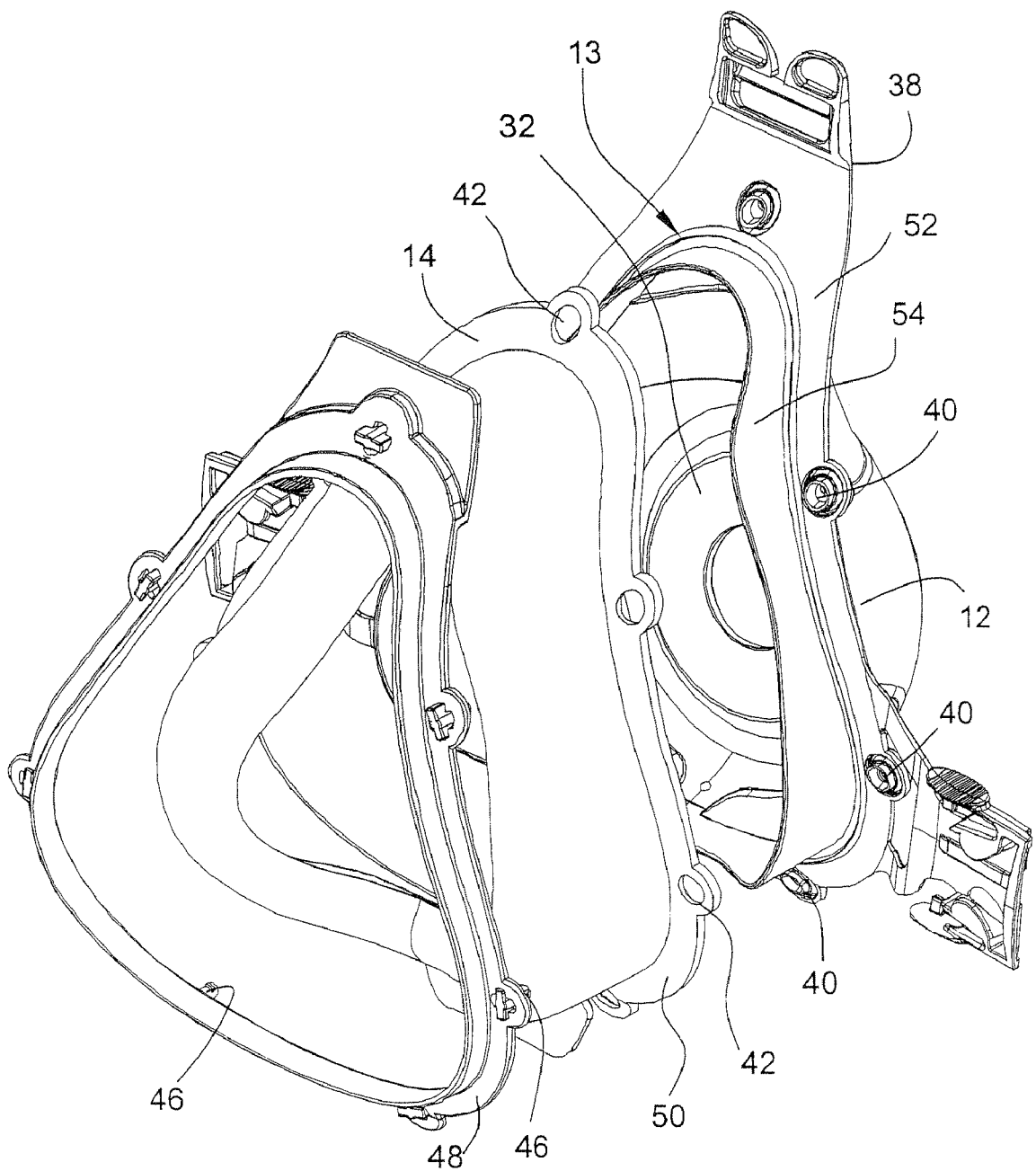
FIG. 4 is a rear perspective exploded view of a portion of the assembly shown in FIG. 1.

FIGS. 3 and 4 illustrate front and rear exploded views of the mask assembly 10 shown in FIG. 1, without the swivel elbow 16 or its associated anti-asphyxia valve membrane 34. As shown in FIG. 3, the anti-asphyxia valve membrane 34 would be positioned adjacent circular support surface 36 of frame 12.

Frame 12 includes at least one and preferably a plurality of through holes 40 which are intended to align with complimentary through holes 42 provided on cushion 14. The cushion 14 is intended to be sandwiched between frame 12 and a cushion clip 44. The cushion clip 44 includes a corresponding number of fasteners or rods 46, e.g., provided along a flanged perimeter portion 48 of the cushion clip 44. The rods 46 are intended to align with and pass through the holes 42 and 40 of the cushion 14 and frame 12, respectively. Tips of rods 46 may be snap-fitted, melted or ultrasonically deformed so as to lock with respect to apertures 40, thereby effectively sandwiching the cushion 14 in place between the frame 12 and the cushion clip 44. Rods 46 may include enlarged head portions that are tapered to allow penetration through holes 40, 42 for assembly purposes. However, enlarged heads help prevent disassembly of the frame, clip and cushion. Therefore, the cushion 14 may be permanently sandwiched in place, i.e., it is difficult to disassemble, which may be a benefit in a hospital or clinical environment. However, the cushion could be structured to allow for selective disassembly, if desired. The cushion 14 includes a lateral perimeter flange 50 which may also be sandwiched or clamped between the frame 12 and the cushion clip 44. FIG. 3 also shows that the flange 50 may provide a support surface for integral connection with port cap 28 via bridge 29. In an alternative, the frame may be provided with the rods, and the cushion clip could be provided with holes.

Figure 5:
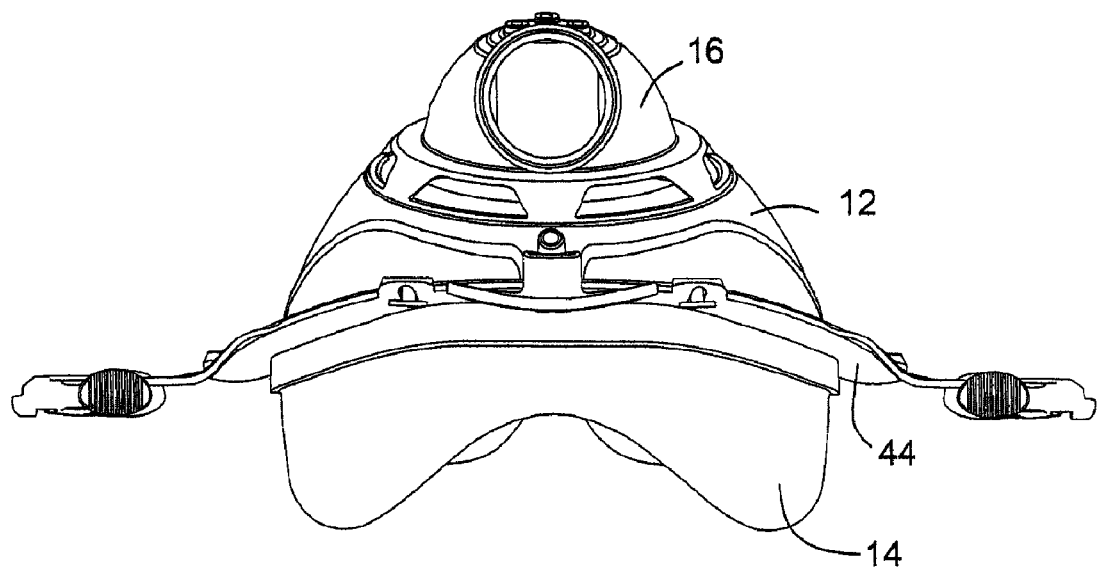
FIG. 5 is a bottom view of the mask assembly shown in FIG. 1.
Figure 6:
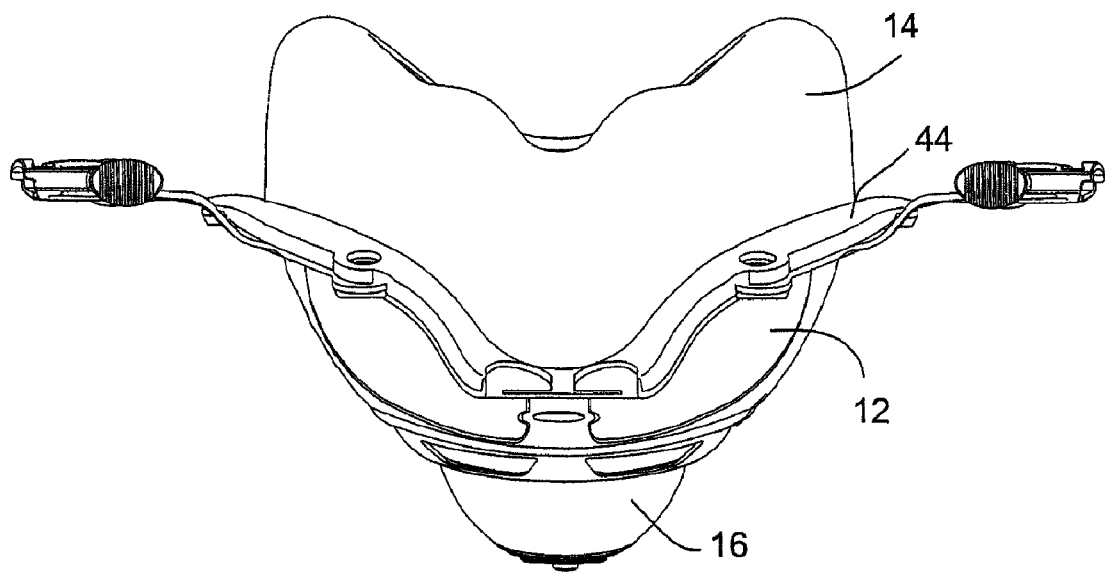
FIG. 6 is a top view thereof.
Figure 7:
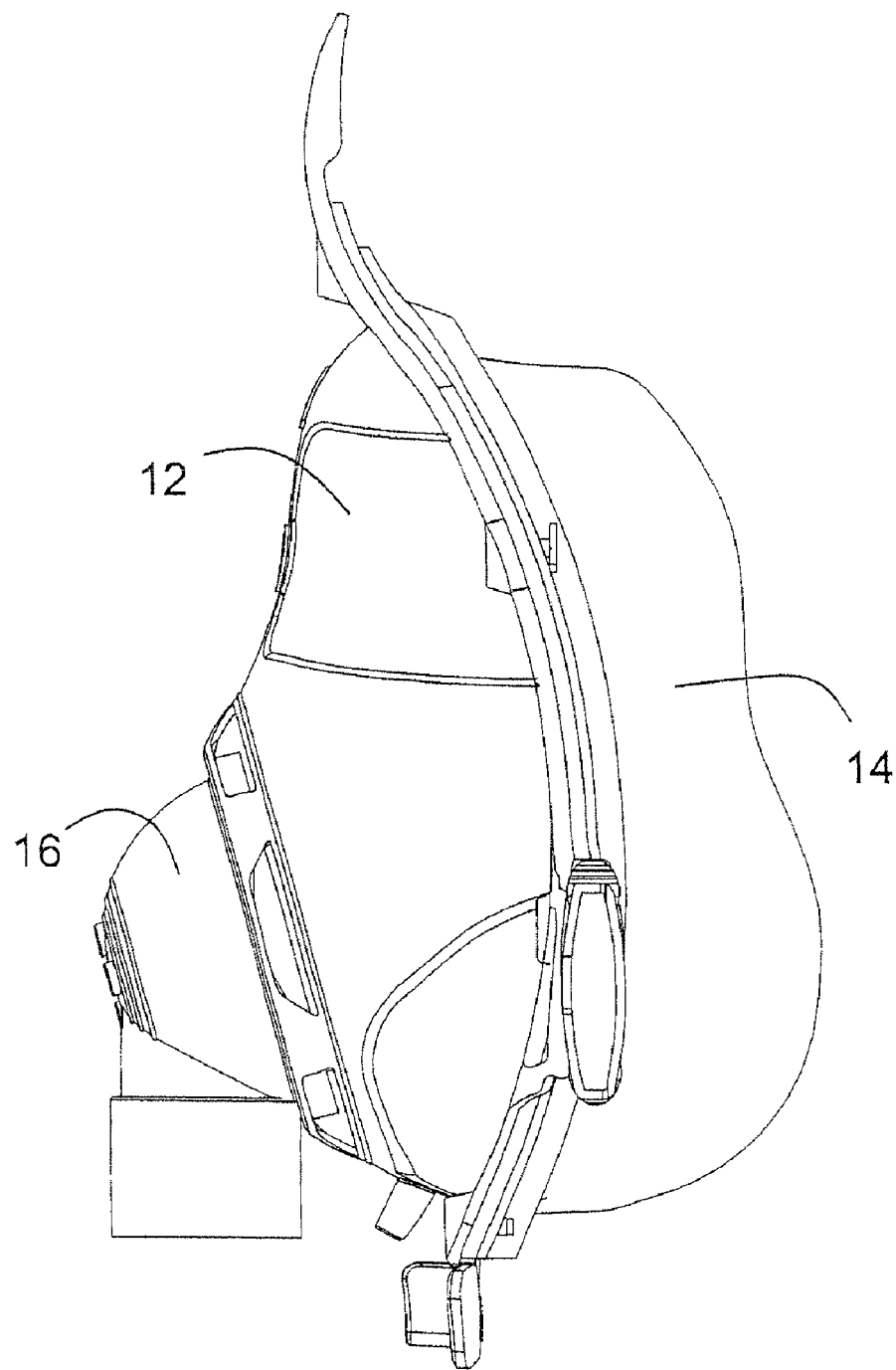
FIG. 7 is a right side view thereof.

FIG. 4 best shows an inside surface 52 of the frame 12. Provided adjacent inside surface 52 is an upstanding wall member 54 which preferably extends along the entire perimeter to define the opening of the frame 12. The wall 54 provides support for the side walls of the cushion 14 as well as the interior side walls of cushion clip 44. FIGS. 5-7 illustrate further assembly views of the frame 12, cushion 14 and swivel elbow 16.

Figure 8:
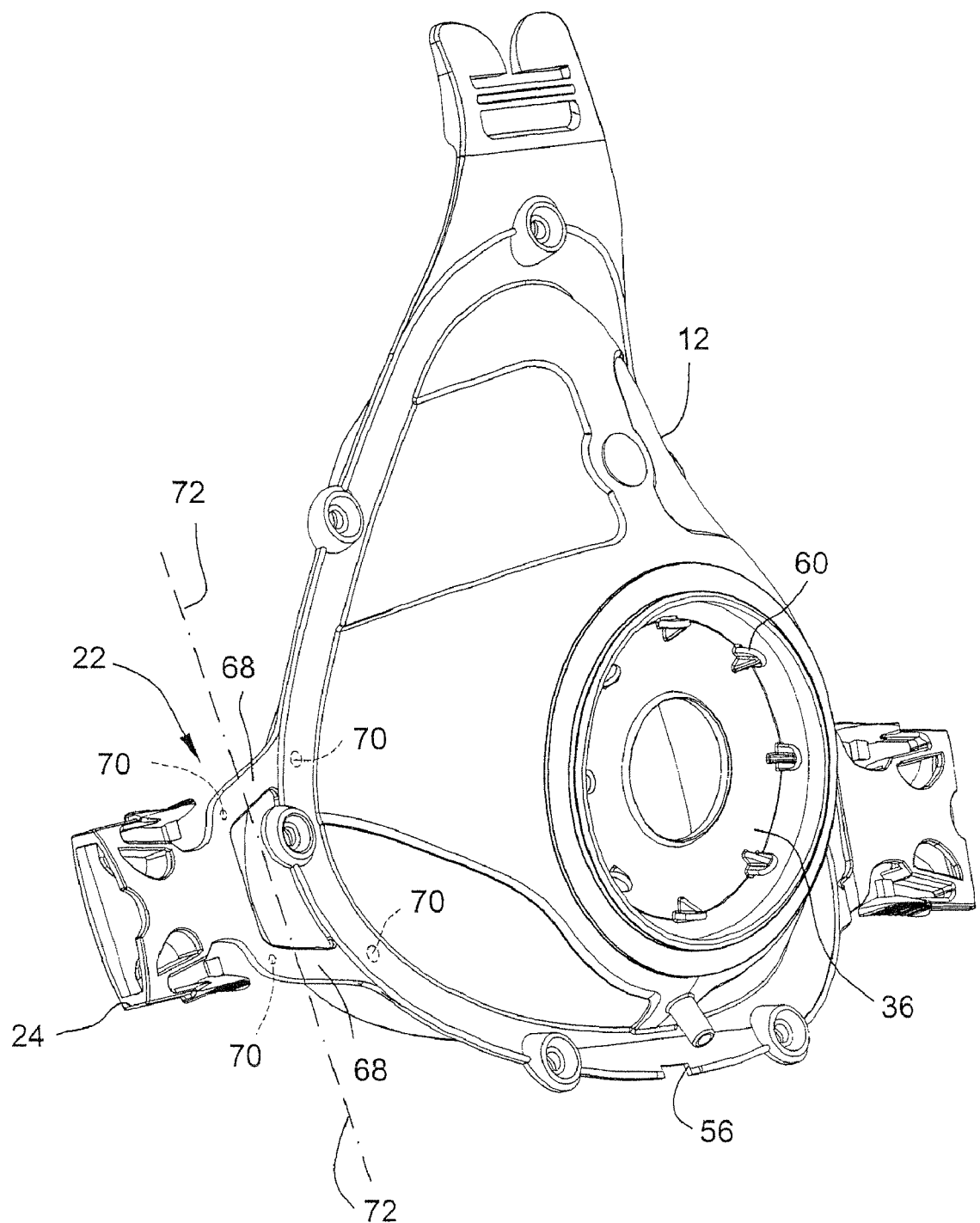
FIG. 8 is a perspective view of a frame according to an embodiment of the present invention.
Figure 10:
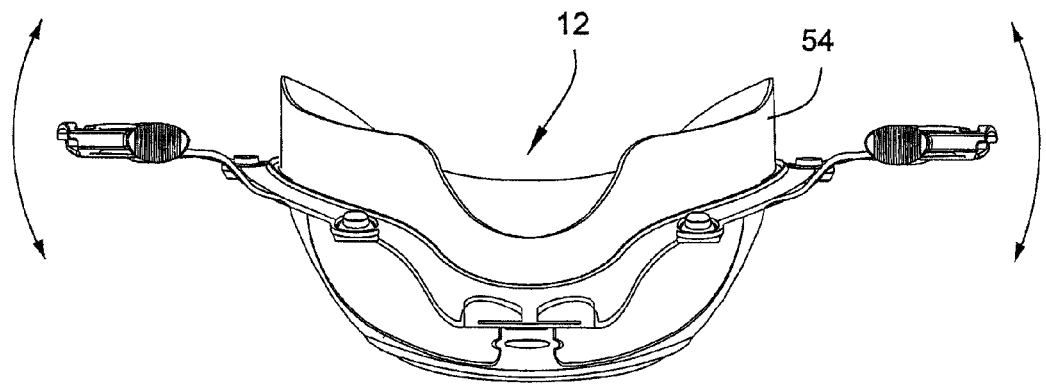
FIG. 10 is a top view thereof.
Figure 11:
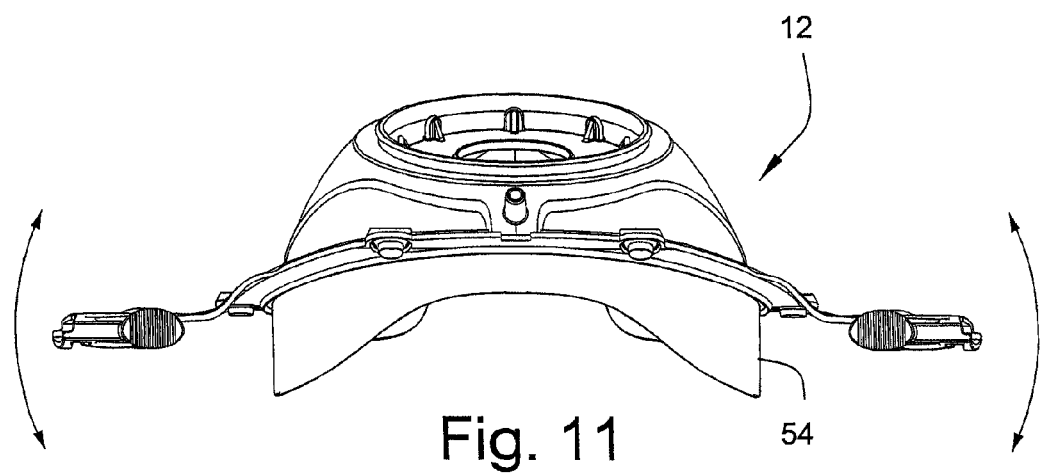
FIG. 11 is a bottom view thereof.
Figure 12:
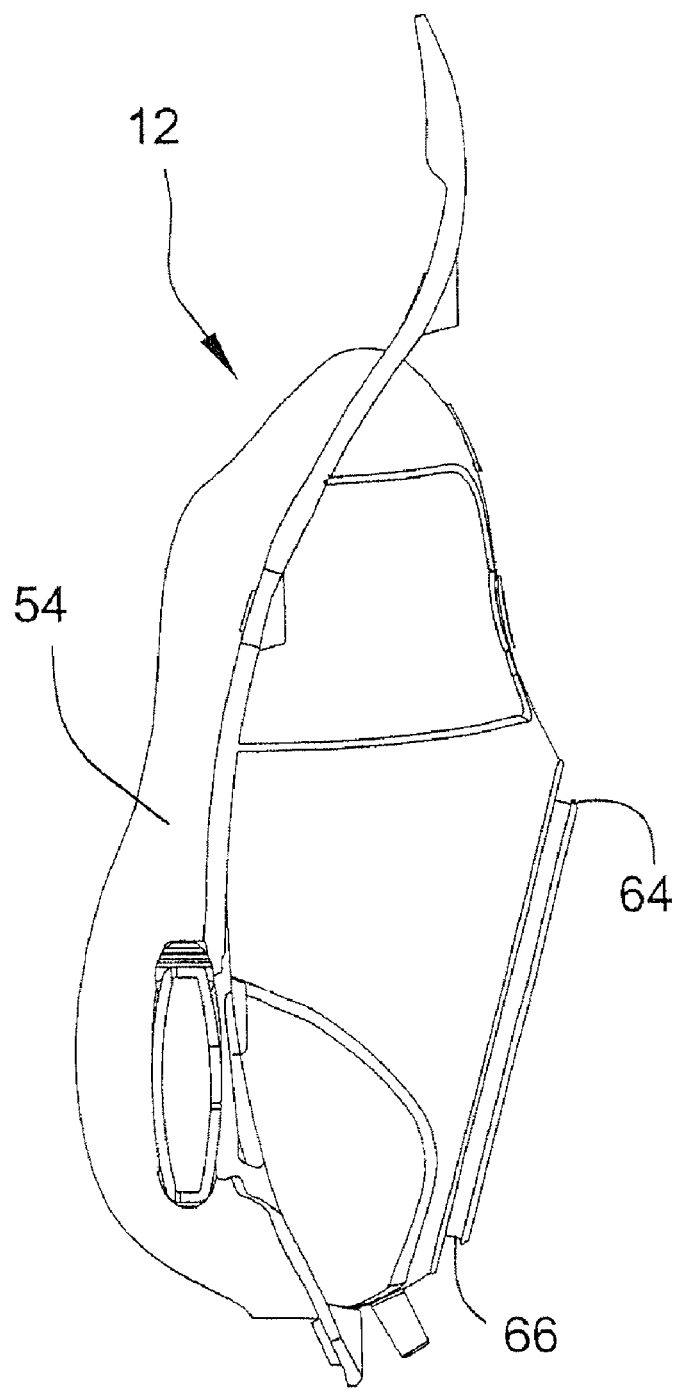
FIG. 12 is a side view thereof.

FIGS. 8-12 illustrate further views of the frame 12 in isolation. FIG. 8 shows that the frame 12 includes a notch 56 provided to facilitate passage of bridge 29 (see FIGS. 3, 14 and 15) from the cushion side to the frame side. The frame 12 also includes a plurality of protrusions or castellations 60, e.g., 8 castellations, for the purposes of assisting with retention of anti-asphyxia valve membrane 34 in elbow assembly (see FIGS. 22, 23 and 29). As shown in FIG. 12, the frame 12 includes a perimeter flange 64 which defines a groove 66 by which the swivel elbow 16 is secured to the frame 12.

Figure 9:
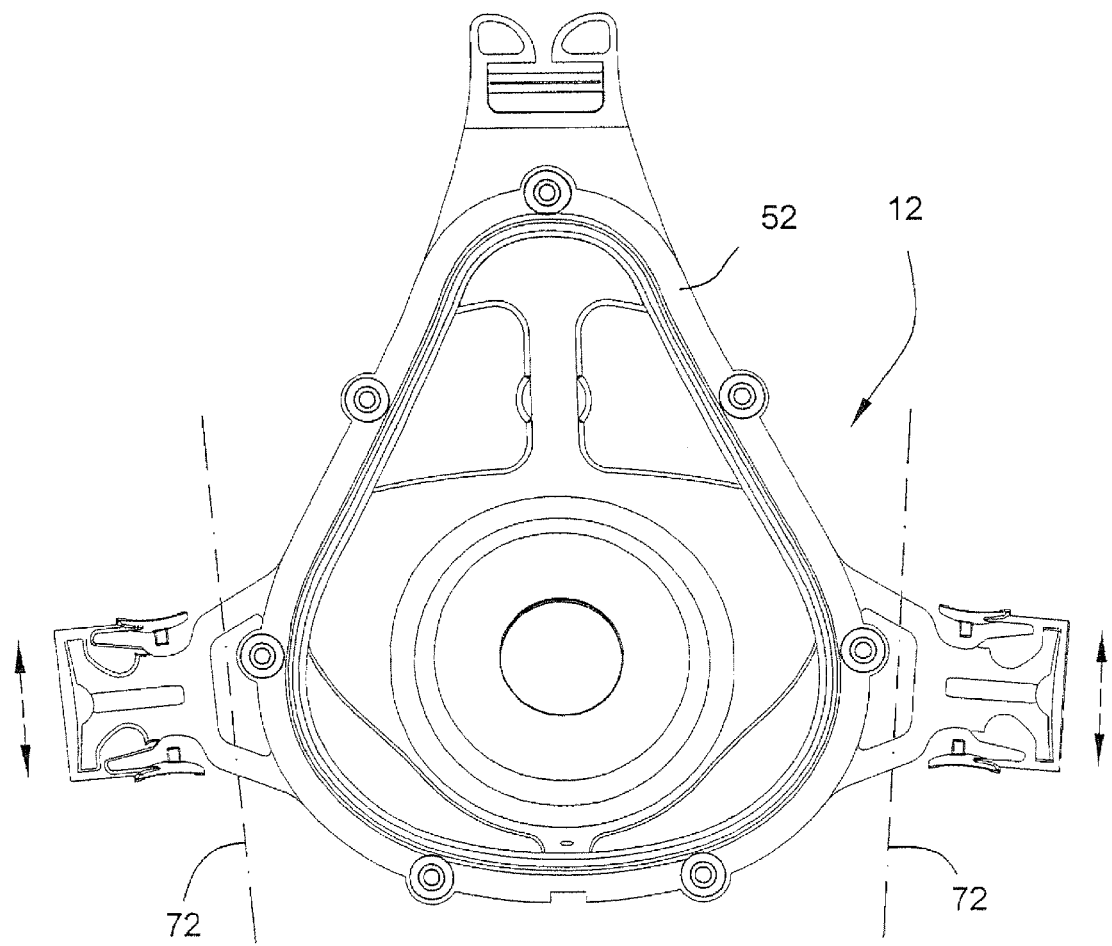
FIG. 9 is a rear view thereof.

FIG. 8 shows that the outrigger 22 includes legs 68, each of which includes a first end attached or otherwise provided to main portion of the frame 12, and a second end attached to or otherwise provided to the connector clip receptacle 24. Preferably, the outriggers are formed as an integral piece with frame 12 and outrigger 24. In addition, the outriggers 22, e.g., legs 68, may bend, and/or flex about an axis 72, as indicated in FIGS. 8 and 9. Legs 68 can also be structured so as to pivot in a hinge-like manner. The provision of this type of movement allows for certain benefits, e.g., headgear strap self-tensioning and/or age/usage indication, more fully described below. FIGS. 10-12 show top, bottom and side views of the frame 12, respectively. FIGS. 10 and 11 have bidirectional arrows which schematically indicate the bending, pivoting and/or flexing of legs 68 about axis 72.

Figure 12A:
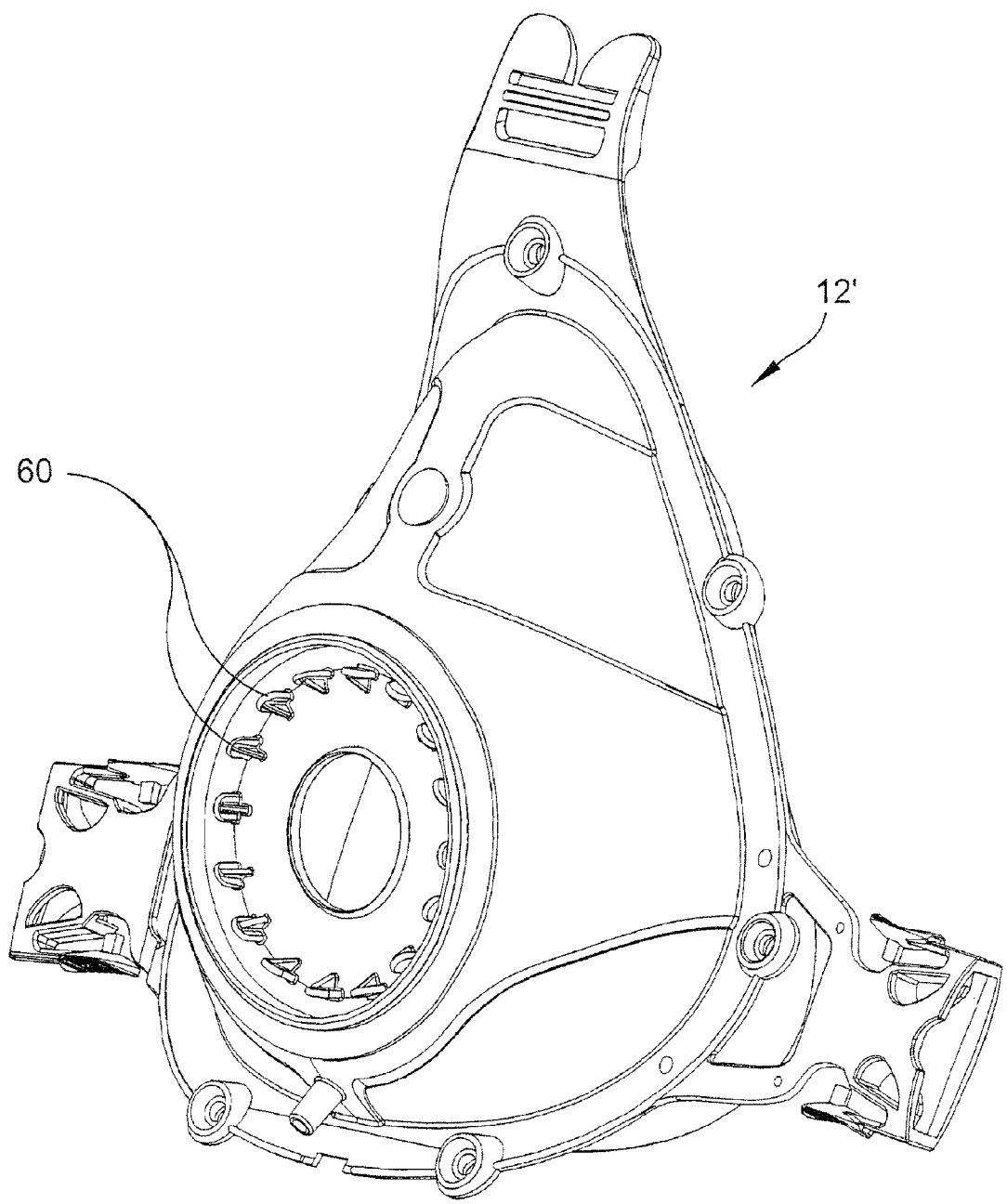
FIG. 12A is a perspective view of a frame according to another embodiment of the present invention.

FIG. 12A illustrates a perspective view of an alternative embodiment of a frame 12'. The frame in FIG. 12A is very similar to the frame shown in FIG. 8, the only main difference being that frame 12' includes 16 instead of 8 castellations 60. The increased number of castellations helps to reduce leak between the elbows and anti-asphyxia valve membrane. However, the number of castellations may vary, and may, for example, include any number above or below 16.

In another embodiment, one or both ends of legs 68 may include a portion 70 about which the arm may pivot, bend and/or flex. This would allow the mask to assume various configurations, e.g., by moving the outrigger vertically up or down with respect to the main body of the frame, as schematically illustrated by arrows in FIG. 9. Preferably, the legs 68 should be parallel to one another to allow this adjustment, even though the legs are seen as non-parallel (i.e., trapezoidal) in FIGS. 8 and 9.

Figure 13:
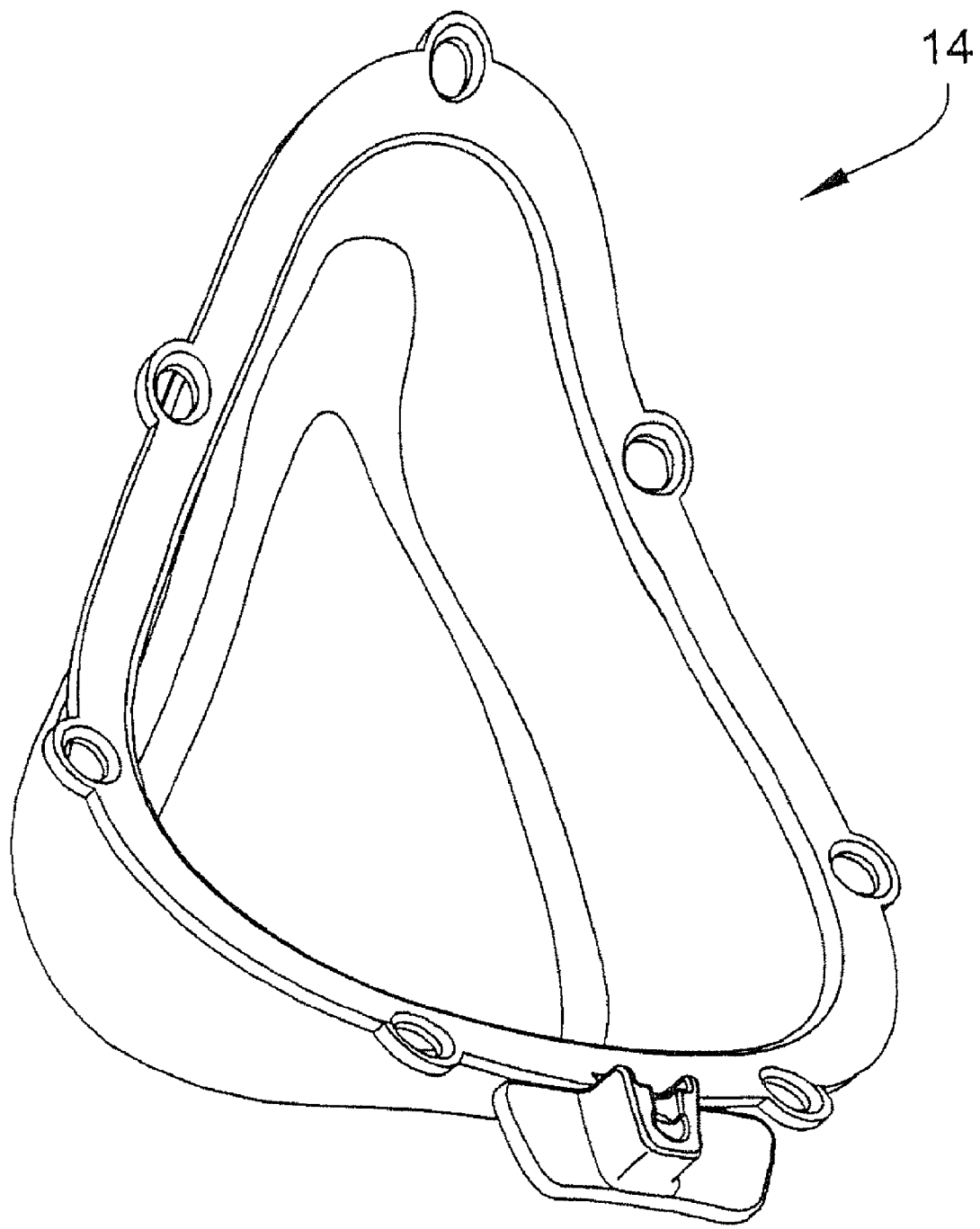
FIG. 13 is a front perspective view of a cushion according to the present invention.
Figure 14:
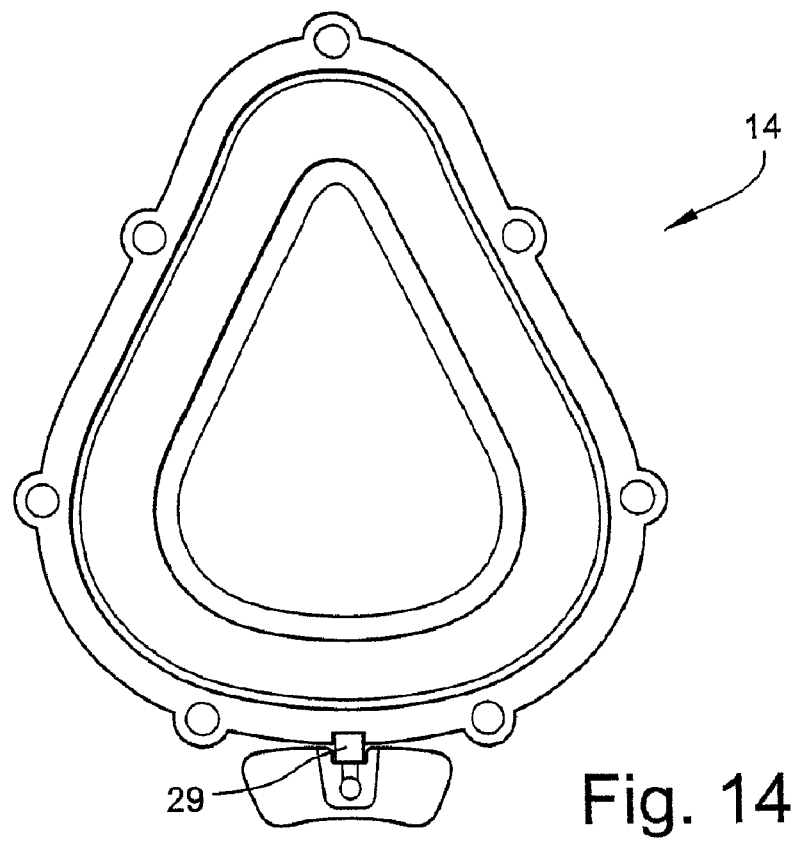
FIG. 14 is a front view thereof.
Figure 15:
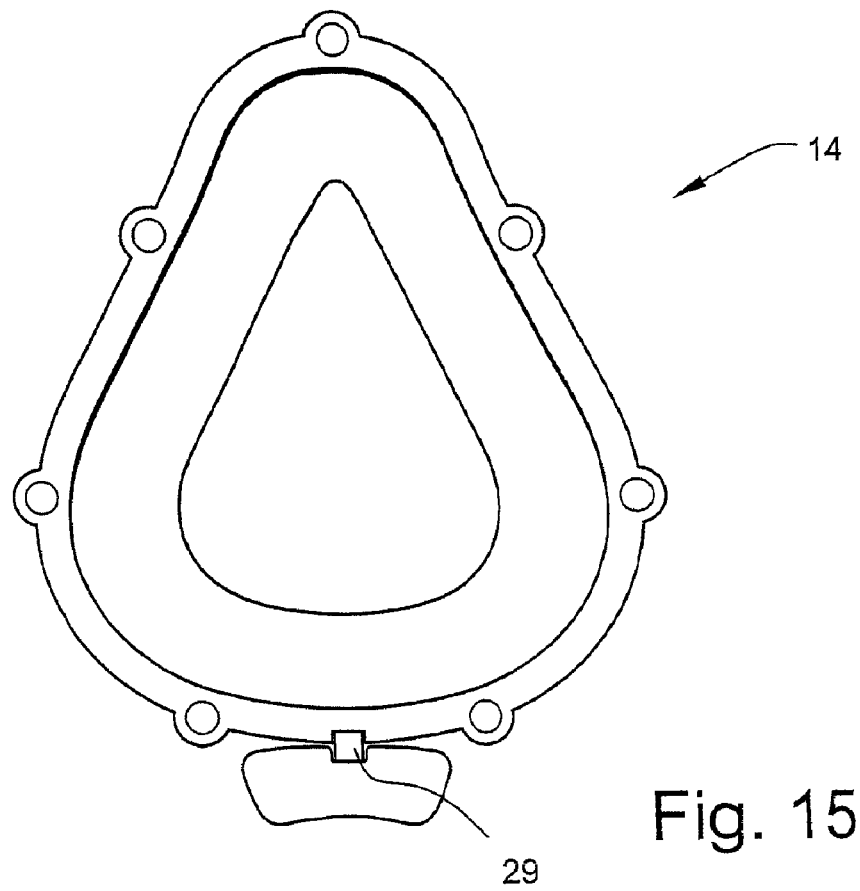
FIG. 15 is a rear view thereof.
Figure 16:
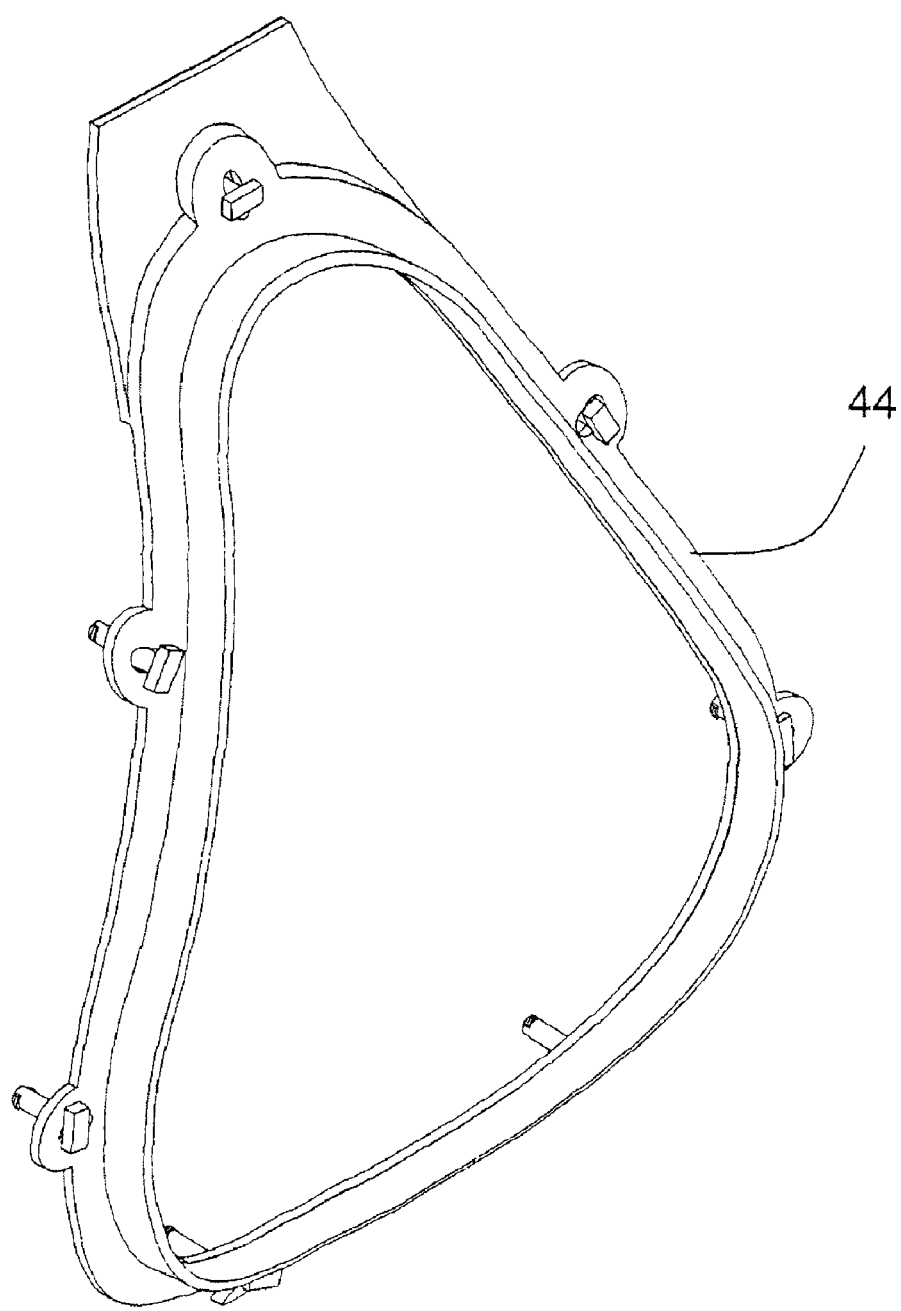
FIG. 16 is a rear perspective view of a cushion clip according to the present invention.
Figure 17:
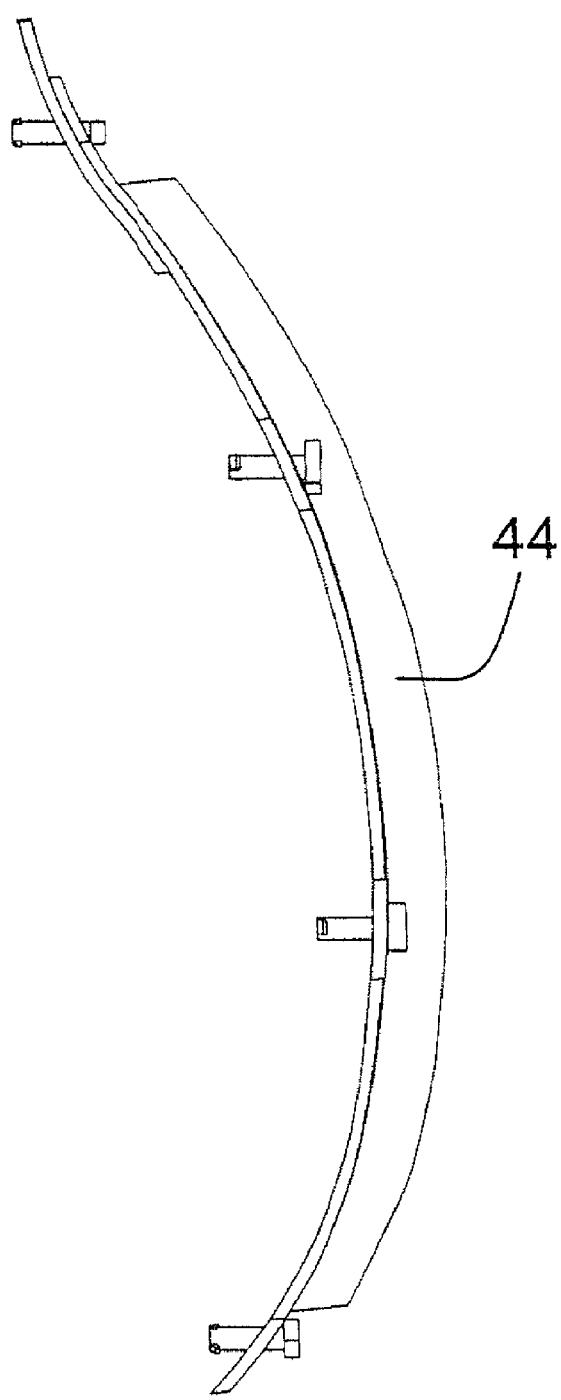
FIG. 17 is a side view thereof.

FIGS. 13 through 15 illustrate various views of the cushion 14 in isolation, while FIGS. 16 and 17 illustrate various views of the cushion clip 44 in isolation.

Figure 18:
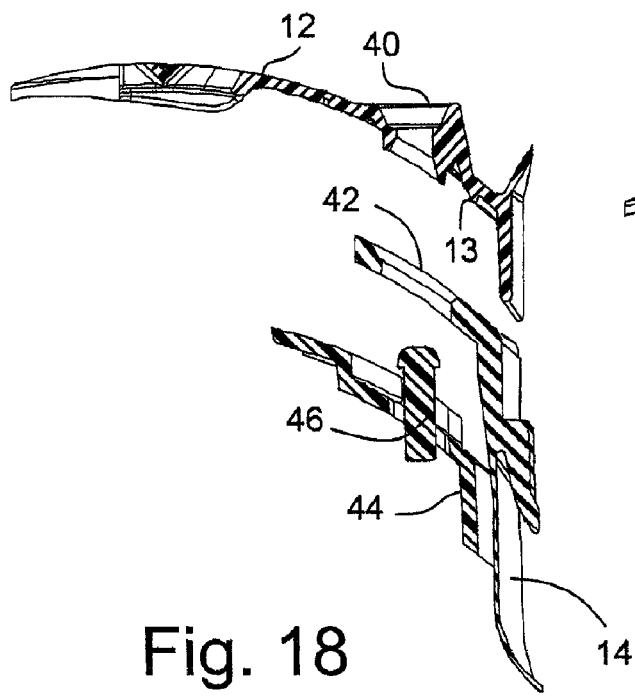
FIG. 18 is a partial exploded cross-sectional view showing assembly of the frame, cushion and cushion clip.
Figure 19:
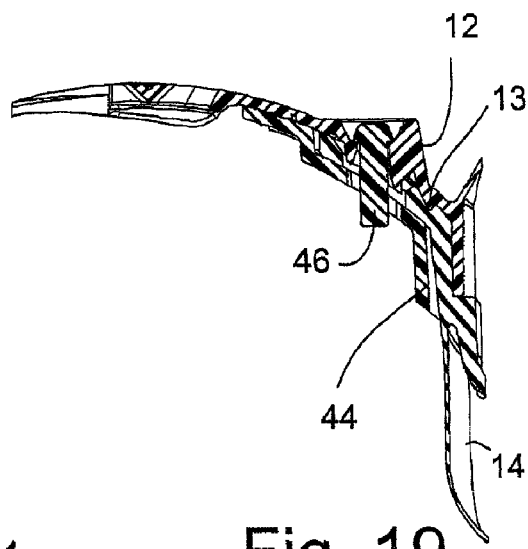
FIG. 19 is an assembled partial cross-sectional view thereof.
Figure 20:
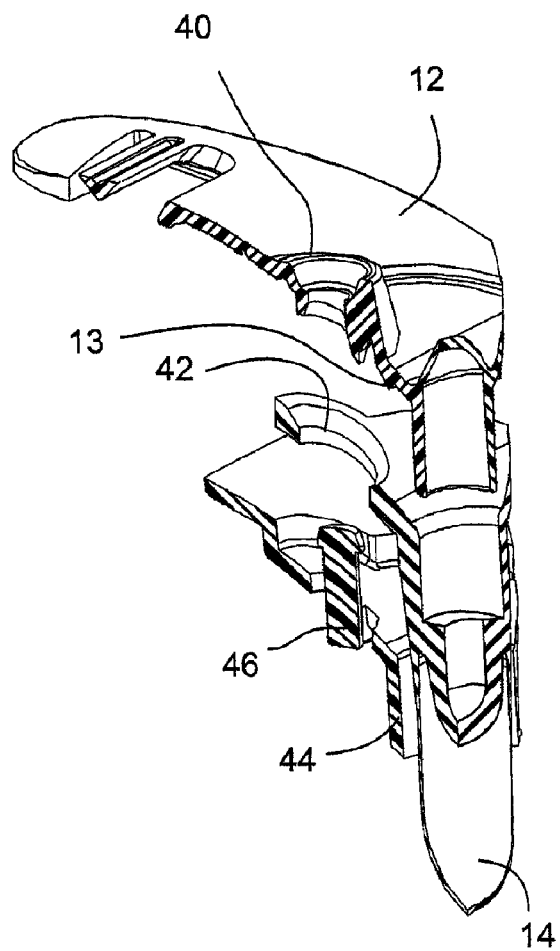
FIG. 20 is a partial exploded cross-sectional perspective view like that shown in FIG. 18.

FIG. 18 illustrates a partial cross-sectional and exploded view to highlight the connection between frame 12, cushion 14, and cushion clip 44. FIG. 19 is an assembled view of the components illustrated in FIG. 18, while FIG. 20 is a perspective version of the exploded view shown in FIG. 18. As seen in FIGS. 18-20, frame 12 includes a bead-like member 13, which helps to establish and ensure a reliable seal between frame 12 and cushion 14. FIG. 19 shows bead member 13 embedded within cushion 14, although cushion 14 could also include a groove or aperture to receive bead member 13. Bead member 13 can also be seen in FIG. 4.

Figure 21:
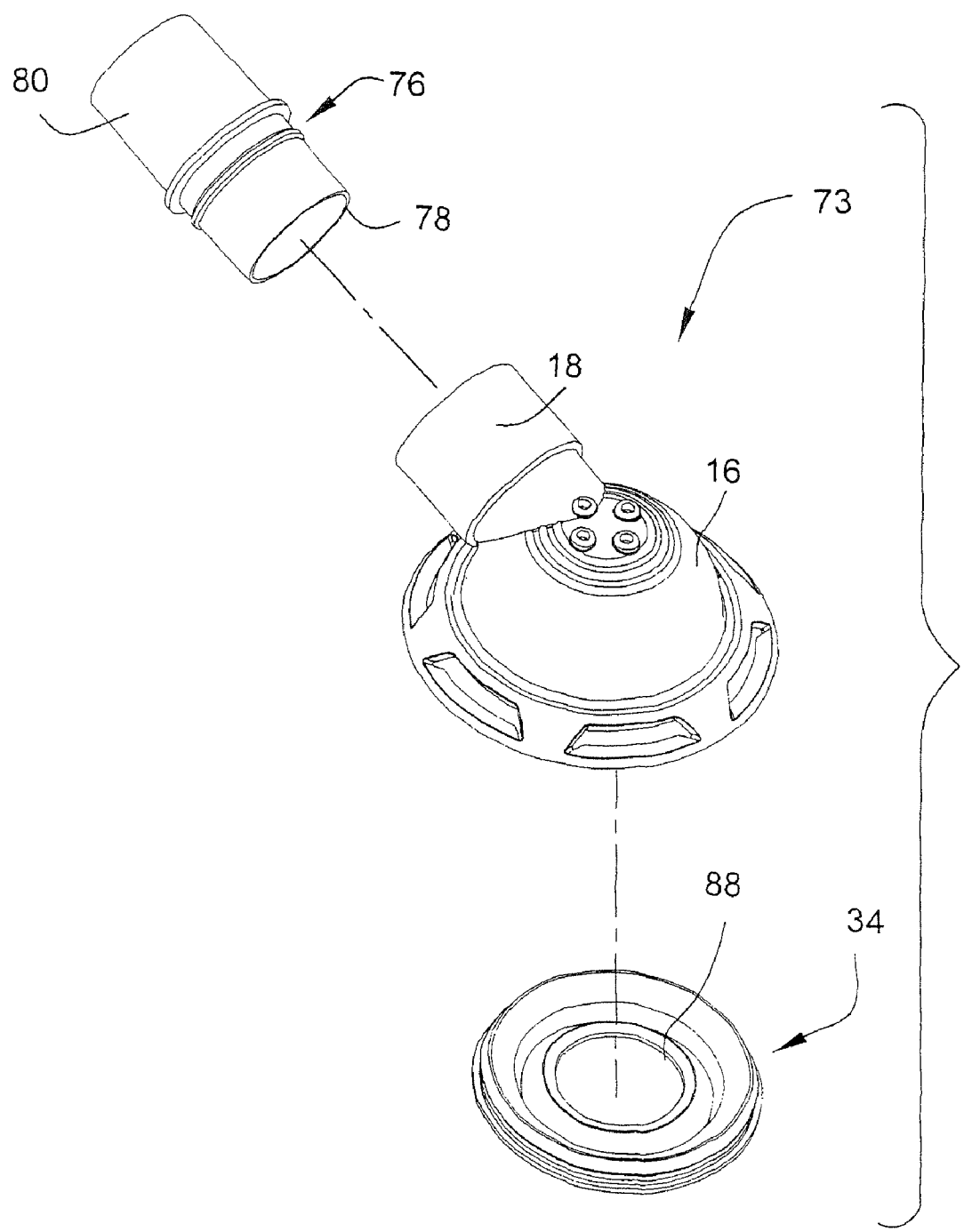
FIG. 21 is an exploded perspective view of a swivel elbow assembly according to the present invention.

FIG. 21 illustrates an exploded view of a swivel elbow assembly 73, including swivel elbow 16, anti-asphyxia valve membrane 34 and swivel joint 76. Swivel joint 76 includes first end 78 provided to inlet conduit 18 and second end 80 provided to an air delivery tube in communication with a source of pressurized breathable gas.

Figure 22:
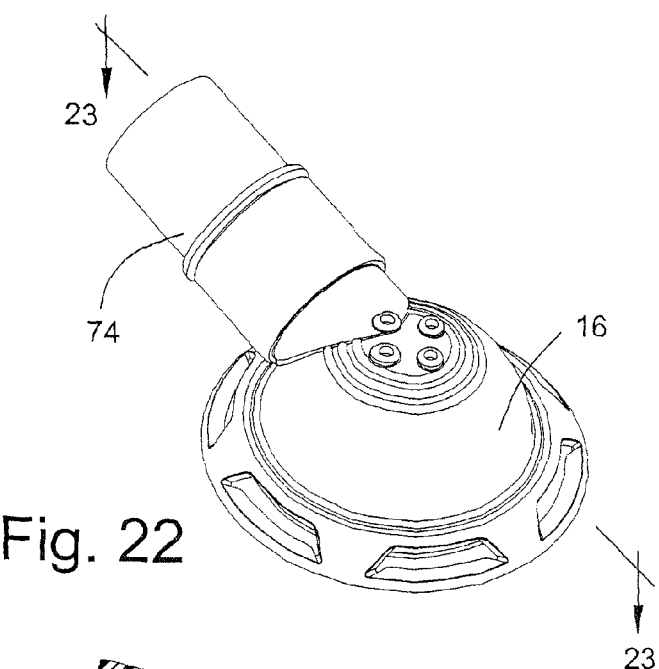
FIG. 22 is an assembled view thereof.
Figure 23:
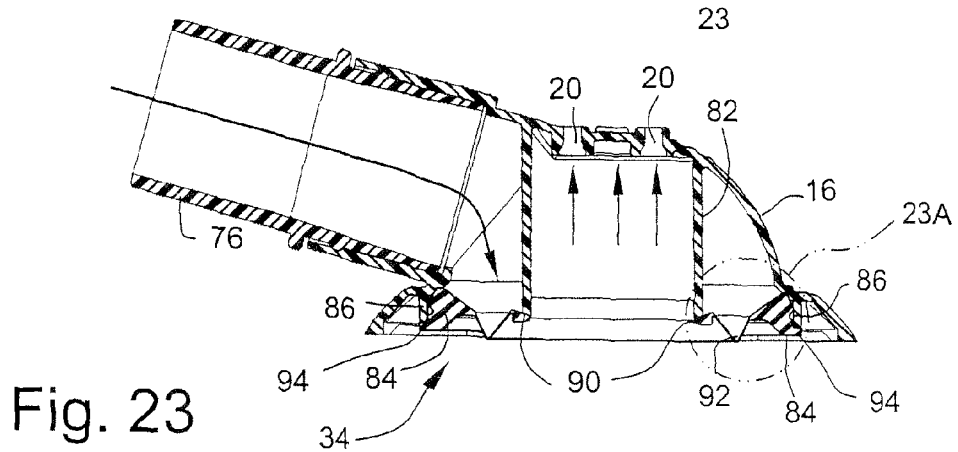
FIG. 23 is a cross-sectional view thereof.
Figure 23A:
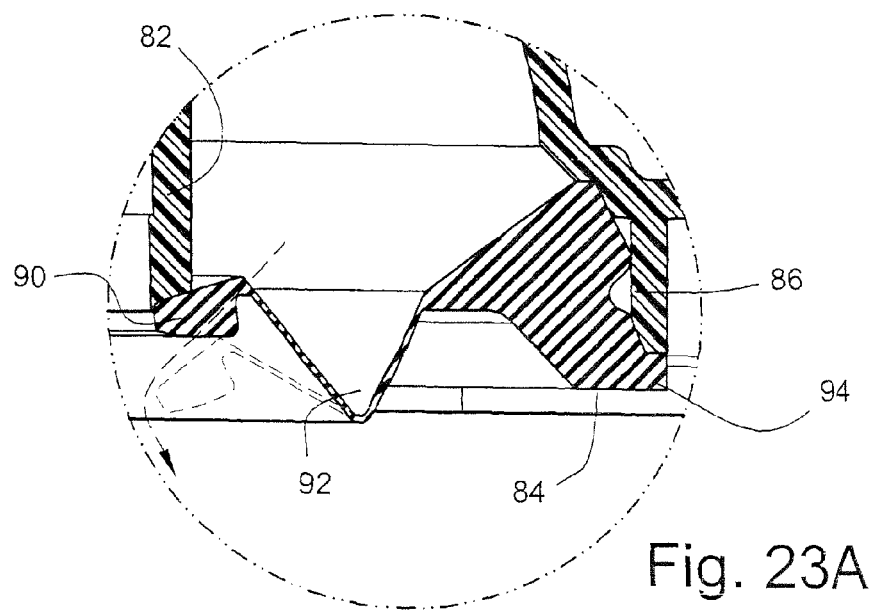
FIG. 23A is an enlarged detail view of a portion of FIG. 23.
Figure 23B:
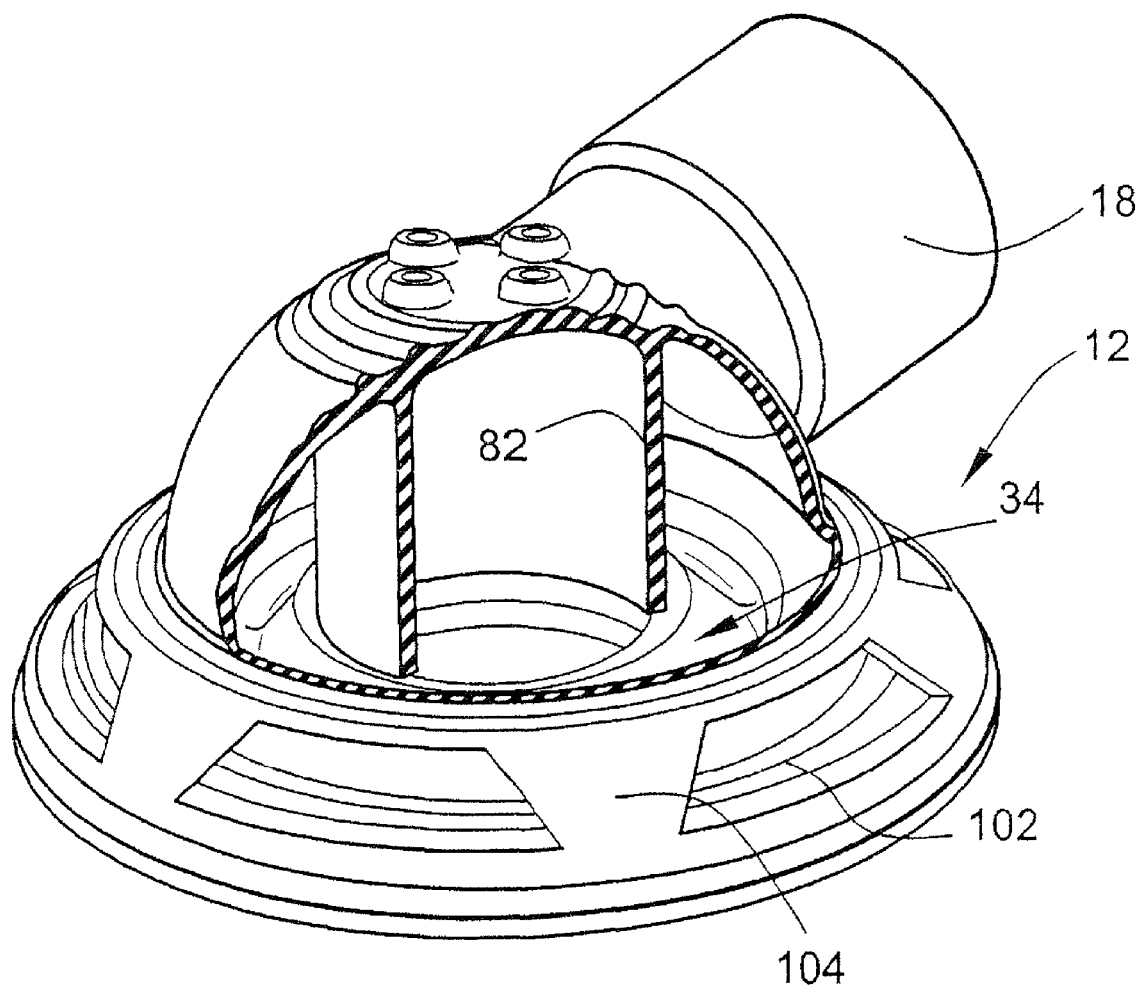
FIG. 23B is a perspective and cross-sectional view of an elbow according to an embodiment of the invention.

FIG. 22 illustrates an assembled view of the components shown in FIG. 21, while FIG. 23 shows a cross-sectional view of the assembled swivel elbow assembly. As shown in FIG. 23, the anti-asphyxia valve membrane 34 is preferably made of an elastomeric material. The swivel elbow 16 includes a generally cylindrical inner tube 82. The cylindrical tube 82 may provide a baffle between incoming air delivered via swivel joint 76 and vented air, as indicated by the directional arrows in FIG. 23. FIG. 23A shows an enlarged detailed view of a portion of the assembly shown in FIG. 23, while FIG. 23B is a partial cross-sectional view illustrating the elbow as connected to frame with member 34 in position.

The anti-asphyxia valve membrane 34 includes a main body 84 which seals and/or interlocks, e.g., via friction, with upstanding wall member 86 formed as part of swivel elbow 16. Anti-asphyxia valve membrane 34 also includes an aperture 88 (FIG. 21) which includes an inner shoulder 90 (FIG. 23) for sealing against the outer surface of cylindrical tube 82 of swivel elbow 16. The anti-asphyxia valve membrane 34 includes an outer shoulder 94 that prevents over-insertion of the membrane 34 within the swivel elbow 16 and allows for a snug fit with upstanding wall member 86 of swivel elbow 16.

Figure 24:
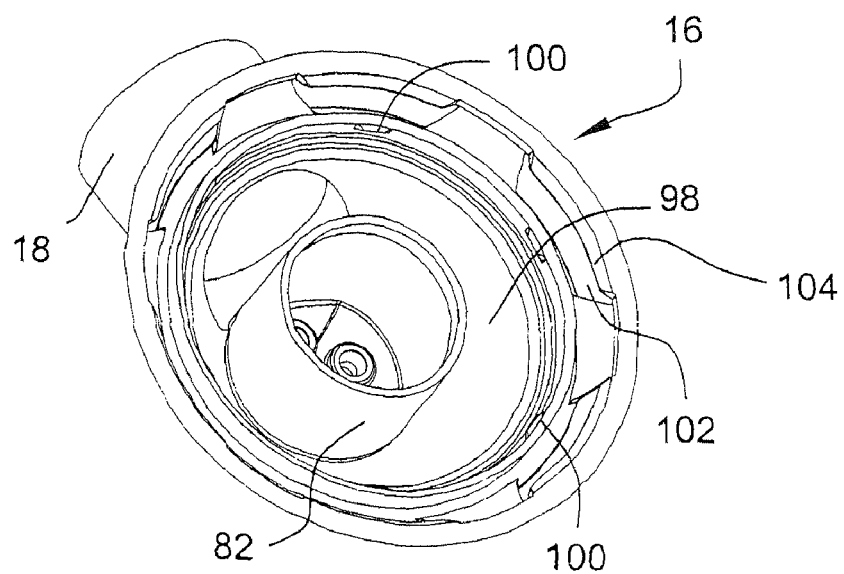
FIG. 24 is a rear perspective view of a swivel elbow according to an embodiment of the present invention.

FIG. 24 illustrates a perspective view of swivel elbow 16 as seen from the patient's side. Air is delivered via inlet conduit 18 into dome portion 98 of swivel elbow 16. The swivel elbow includes a plurality of friction enhancing members 100 designed to ensure that the anti-asphyxia valve membrane 34 stays frictionally engaged with the swivel elbow 16.

Figure 25:
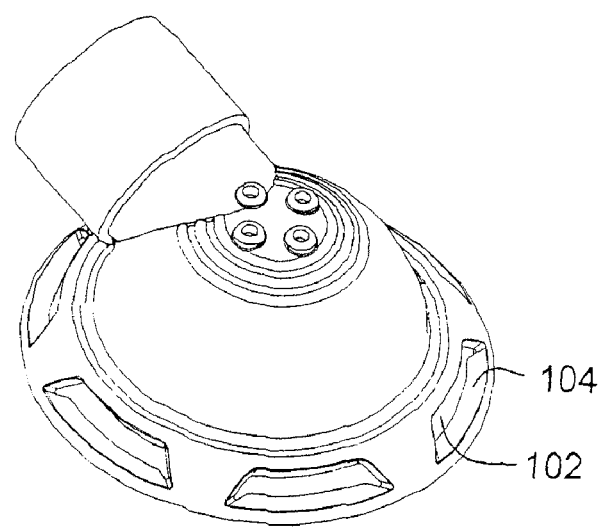
FIG. 25 is a front perspective view thereof.

The swivel elbow 16 also includes a plurality of slots or apertures 102 adjacent to which a plurality of tab members 104 are positioned, as seen in FIGS. 24 and 25. The tab members 104 are inclined (FIG. 24) so that they slightly expand or cam-out upon engaging flange 64 as shown in FIG. 12, until overcoming the flange 64 and seating the tab members 104 within groove or undercut 66, at which point the parts snap-fit to establish a connection. The provision of apertures 102 helps to weaken the swivel elbow 16 such that upon an attempt to disassemble the swivel elbow from the mask, the portion supporting the tab members or the tab members themselves deform and/or break away from the swivel elbow 16, thereby rendering the mask unusable, in which case a new mask would be required for the patient. However, the selective weakening does not adversely impact the performance of the mask. Apertures 102 may also act as windows for breathing to atmosphere when the anti-asphyxia valve member is de-activated.

Figure 26:
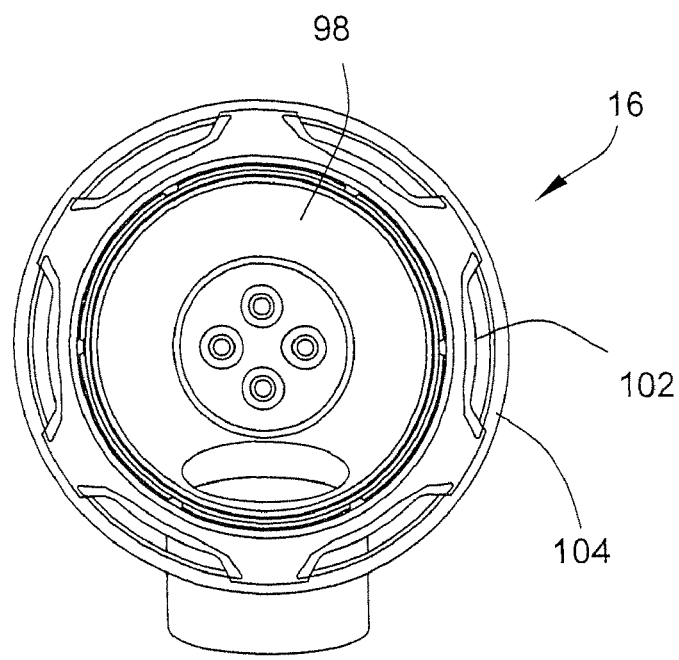
FIG. 26 is a rear view thereof.
Figure 27:
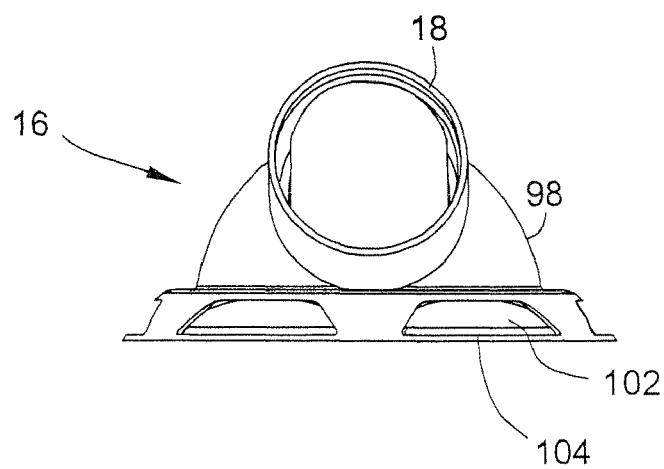
FIG. 27 is a bottom view thereof.
Figure 28:
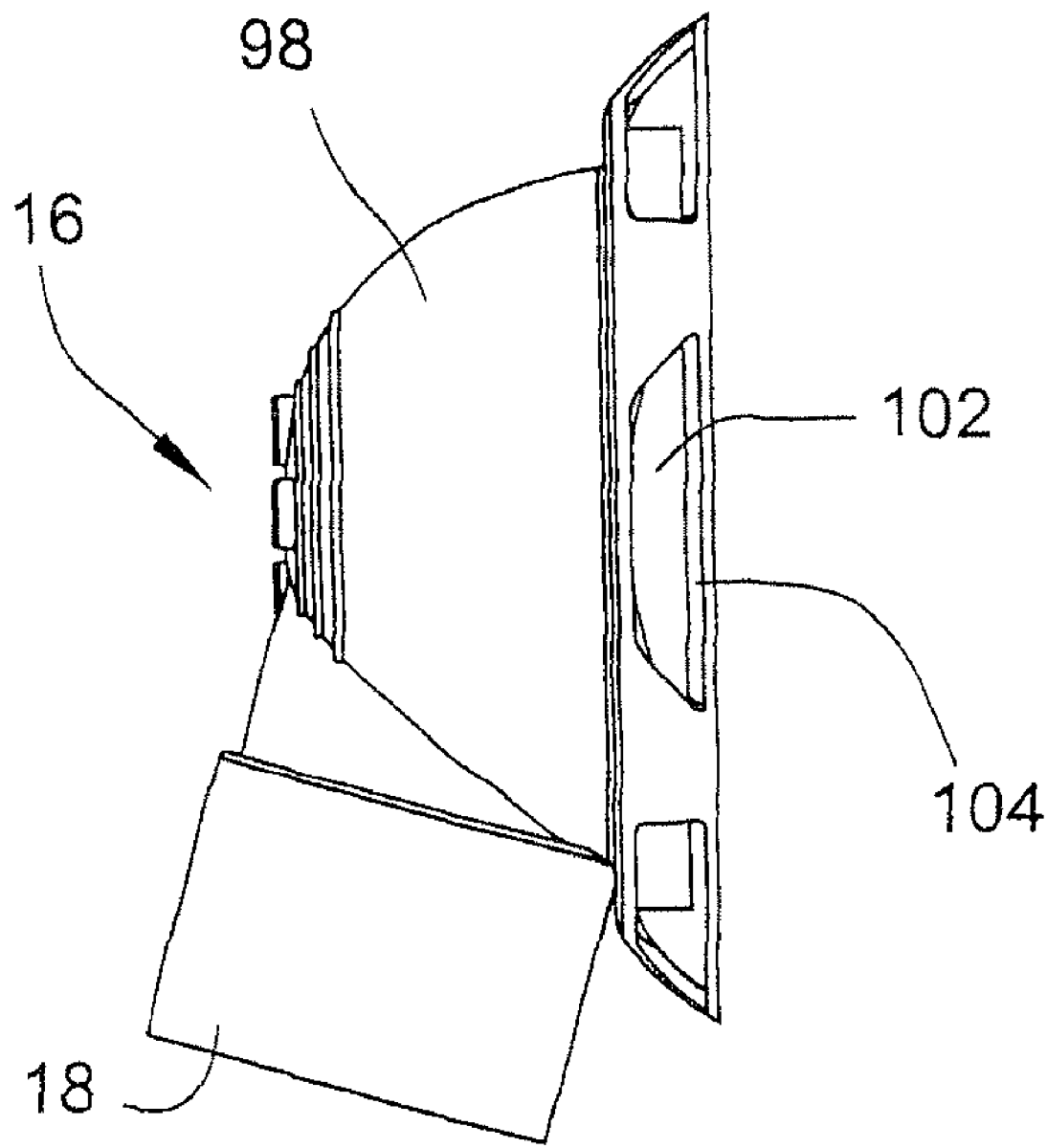
FIG. 28 is a side view thereof.
Figure 29:
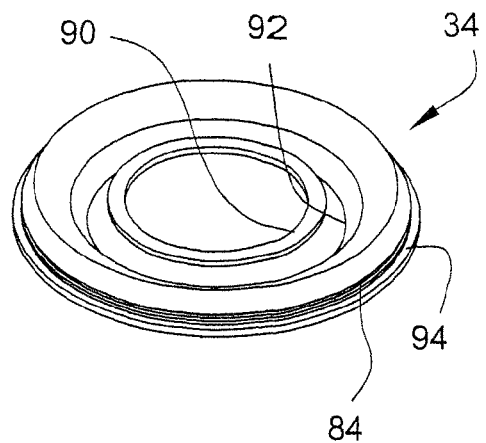
FIG. 29 is a front perspective view of an anti-asphyxia valve membrane according to the present invention.
Figure 30:
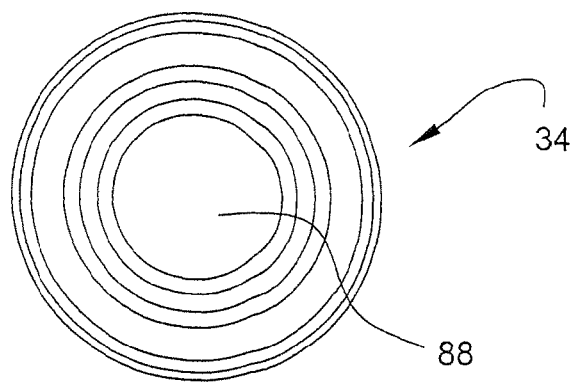
FIG. 30 is a front view thereof.
Figure 31:
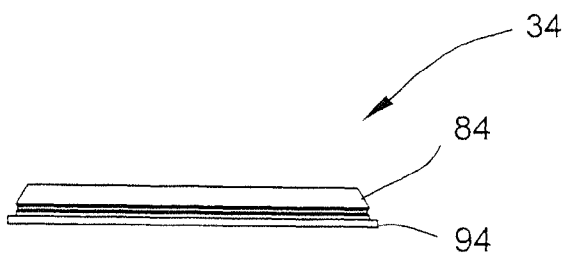
FIG. 31 is a side view thereof.

FIGS. 26 through 28 illustrate various views of the swivel elbow 16 in isolation, while FIGS. 29 through 31 illustrate various views of the anti-asphyxia valve member 34 in isolation.

Figures 1, 28A:
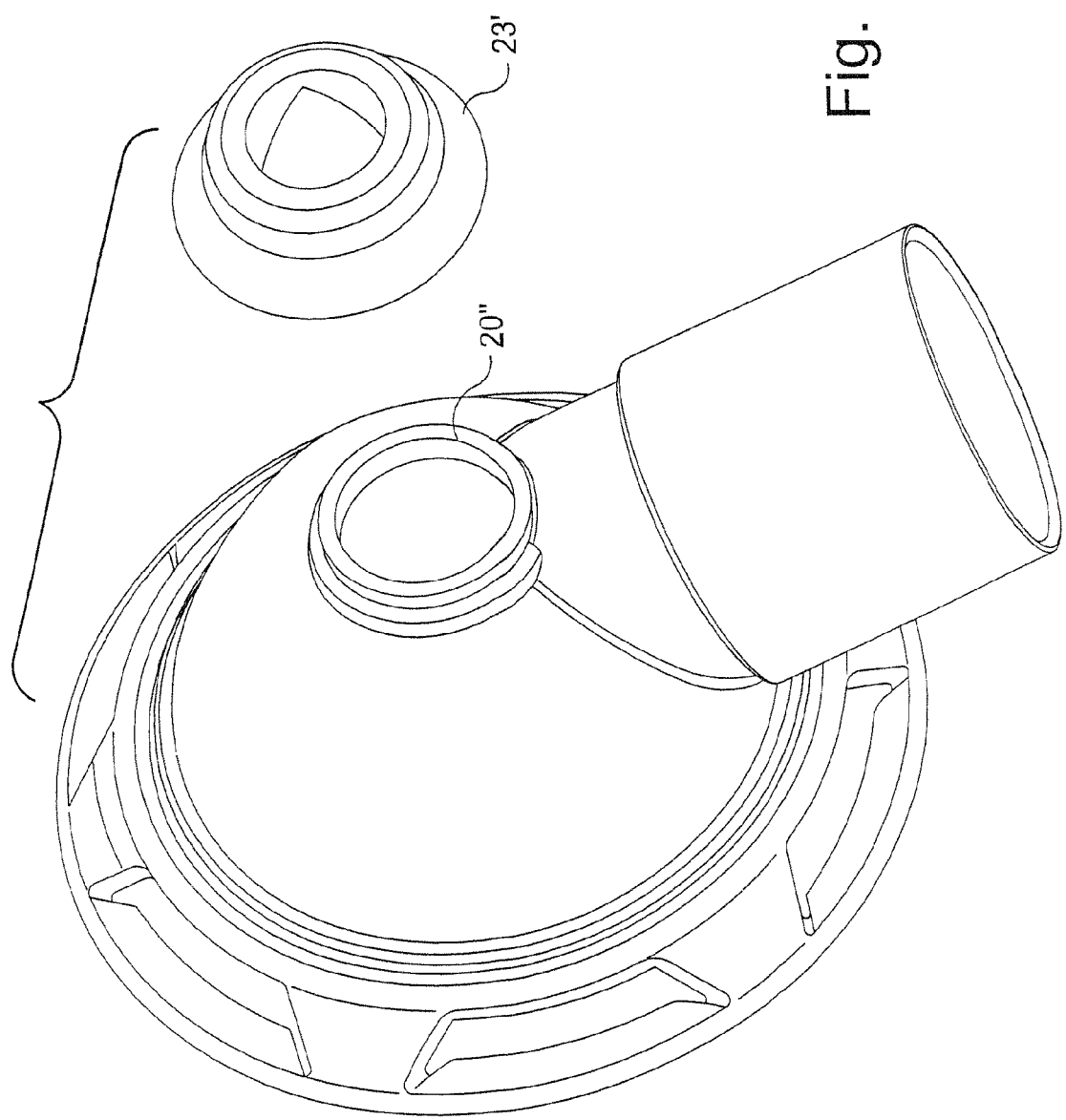
FIG. 28A illustrates a perspective view of a swivel elbow according to another embodiment of the present invention.
Figures 2, 28A:
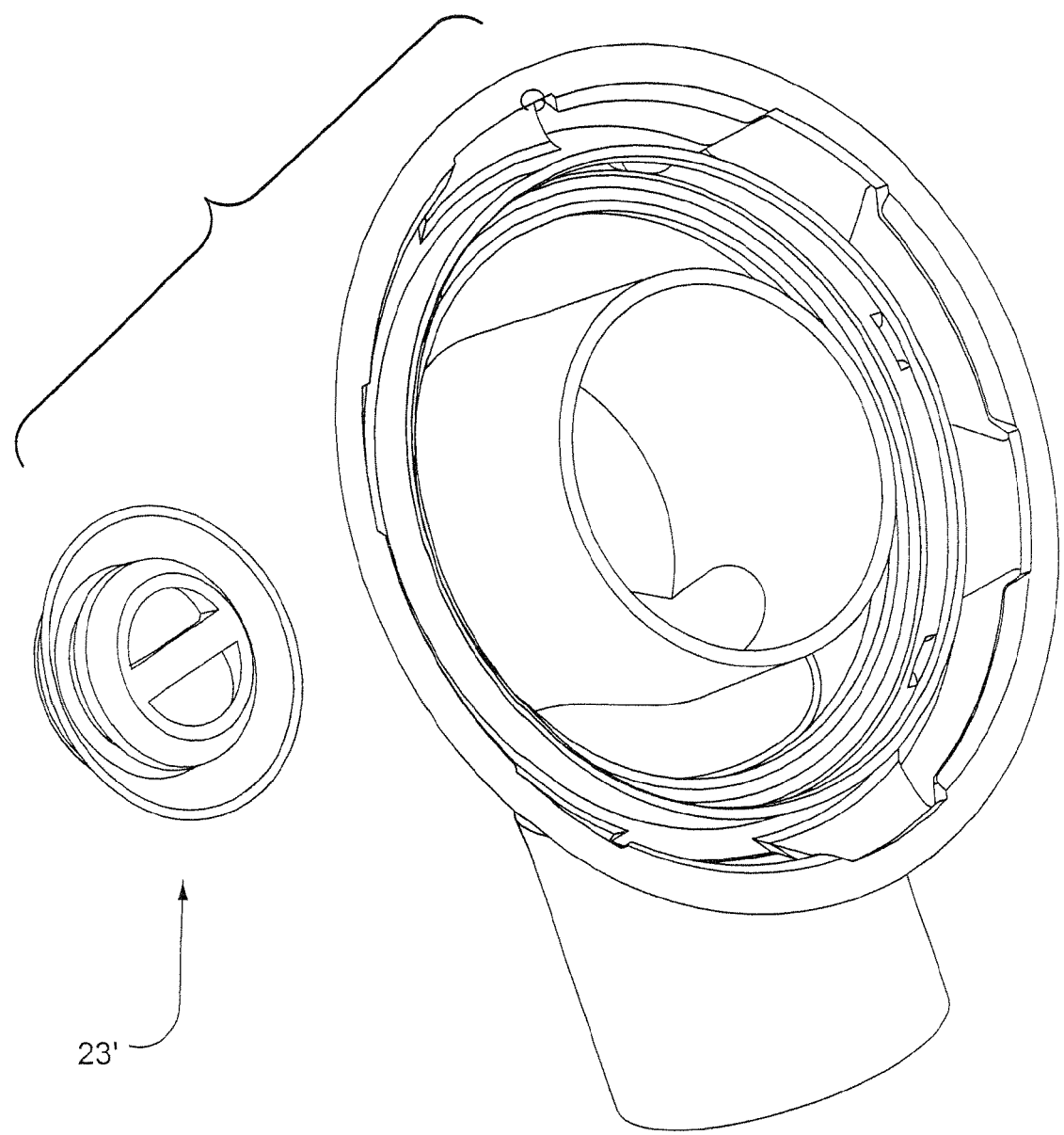

FIG. 28A illustrates another embodiment of the invention, including a swivel elbow 16' which is similar to elbow 16 shown in FIG. 22. One of the main differences is that elbow 16' includes a single aperture 20' provided for washout of exhaled $CO_2$ gas. Aperture 20' may be fitted with a duck bill valve 23, which is known in the art.

FIGS. 28A-1 and 28A-2 illustrate an elbow according to a slight modification, in which the aperture 20" is raised and a valve member 23' is attached thereto.

In the embodiments of FIG. 28A and FIGS. 28A-1 and 28A-2, members 23, 23' constitute valve members. In another embodiment, members 23, 23' could constitute plugs that selectively seal the aperture. When the plug is in place, the aperture is sealed and the elbow is non-vented. When the plug is removed, the aperture is exposed, thereby serving as an access port to receive a tube, e.g., naso-gastric in nature.

Figure 28B:
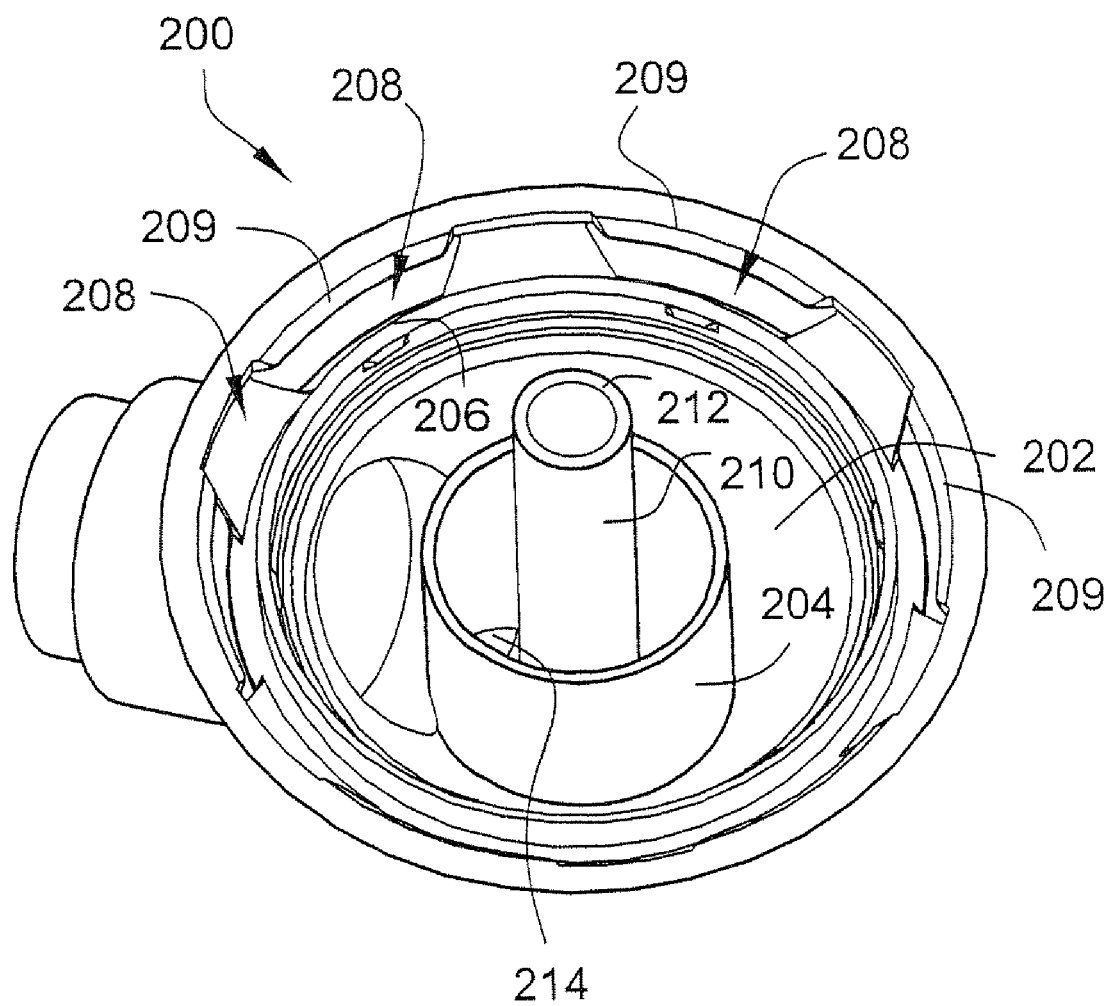
FIGS. 28B-28C illustrate views of an elbow according to an alternative embodiment of the present invention.
Figure 28C:
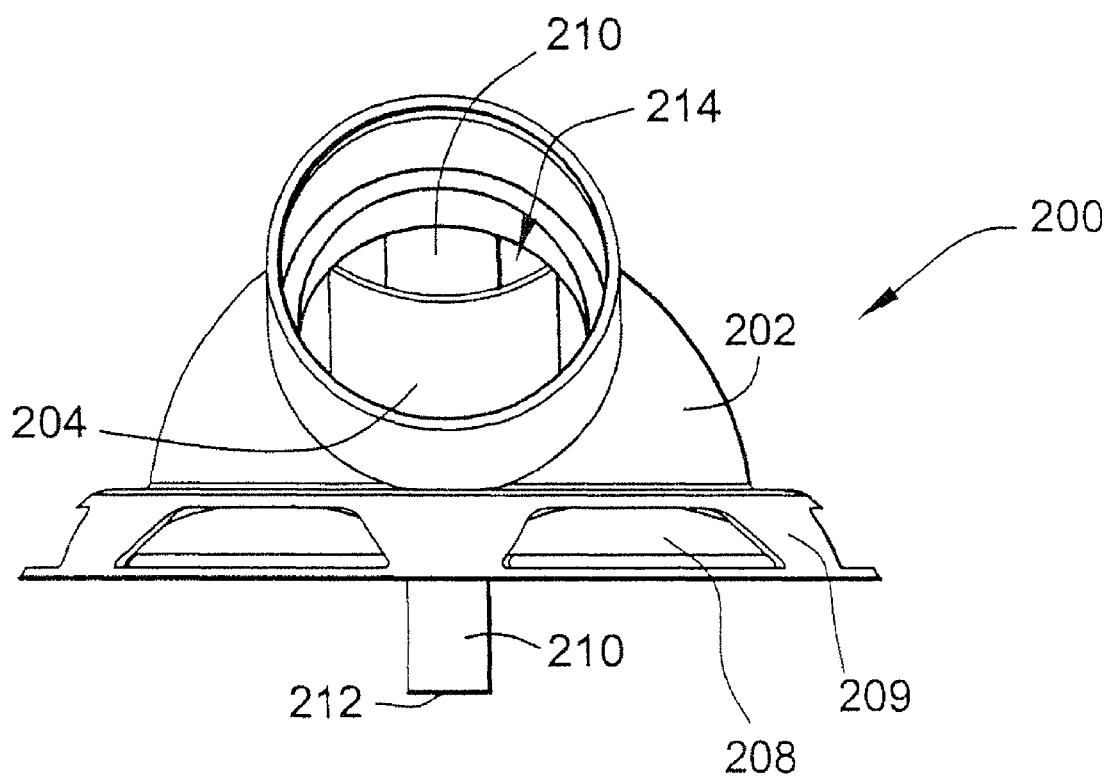

FIGS. 28B and 28C illustrate a swivel elbow 200 according to yet another embodiment of the present invention. Elbow 200 is intended to include an anti-asphyxia valve membrane (not shown) as described above. As shown in FIG. 28A, elbow 200 includes a dome portion 202 and a cylindrical center tube member 204. Upstanding wall 206 and tube member 204 are structured to support anti-asphyxia valve member. Dome is provided with a plurality of slots or apertures 208 and tab members 209, each of which function as described herein. Provided to a peak portion of the dome 202 is a tube 210 having a first end 212 that extends through central aperture of anti-asphyxia valve membrane. Tube 210 includes a second end (not visible) which is integrally connected or provided to the peak of dome 202. As such, dome will include only a single aperture, like that shown in FIG. 28A.

As shown in FIG. 28C, tube member 204 includes an aperture 214 which is provided at a base of tube member 204. Aperture 214 in this example is eye-shaped, although it could have any shape.

Figure 28D:
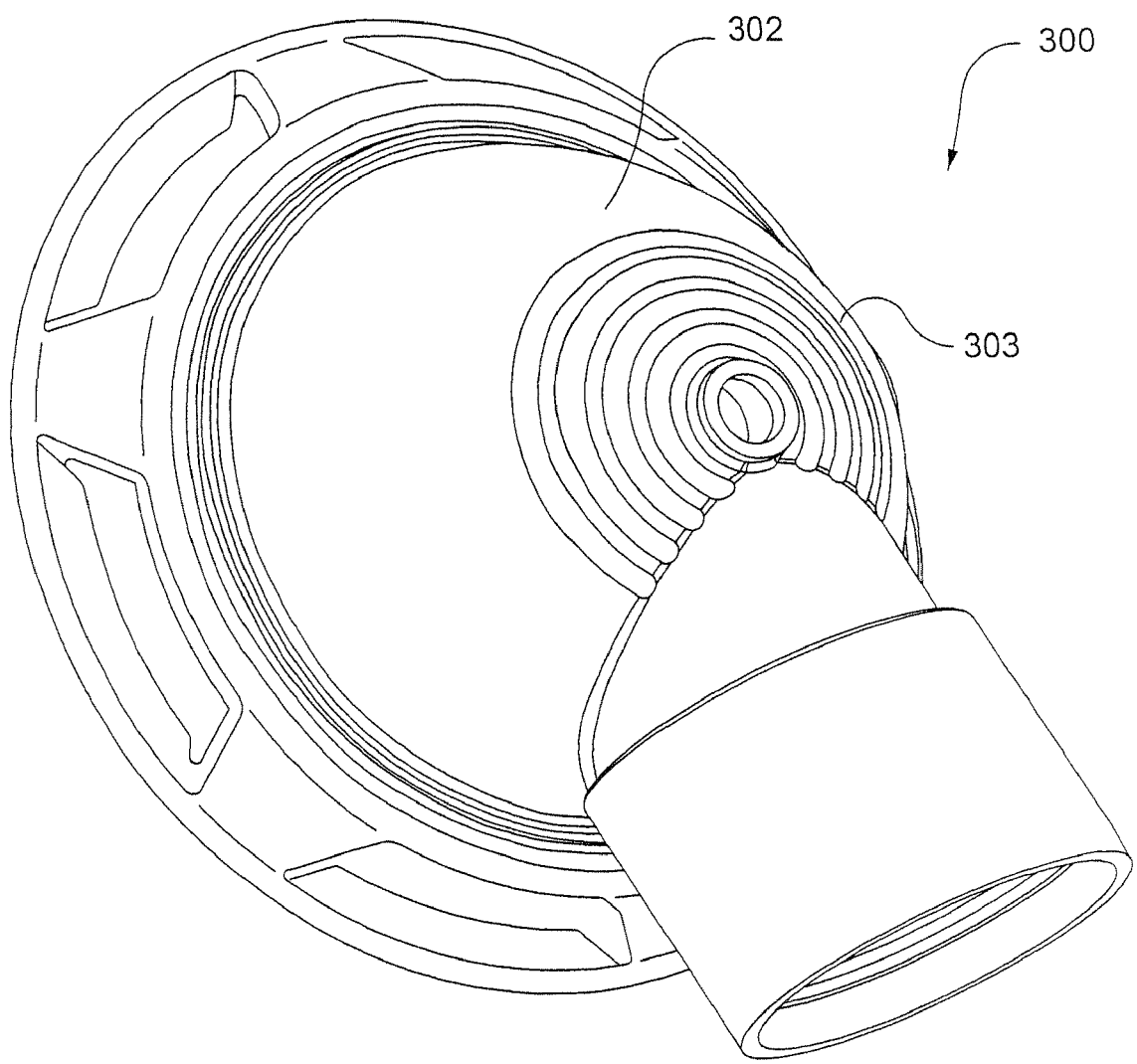
FIGS. 28D-28H illustrate views of an elbow according to yet another embodiment of the present invention.
Figure 28E:
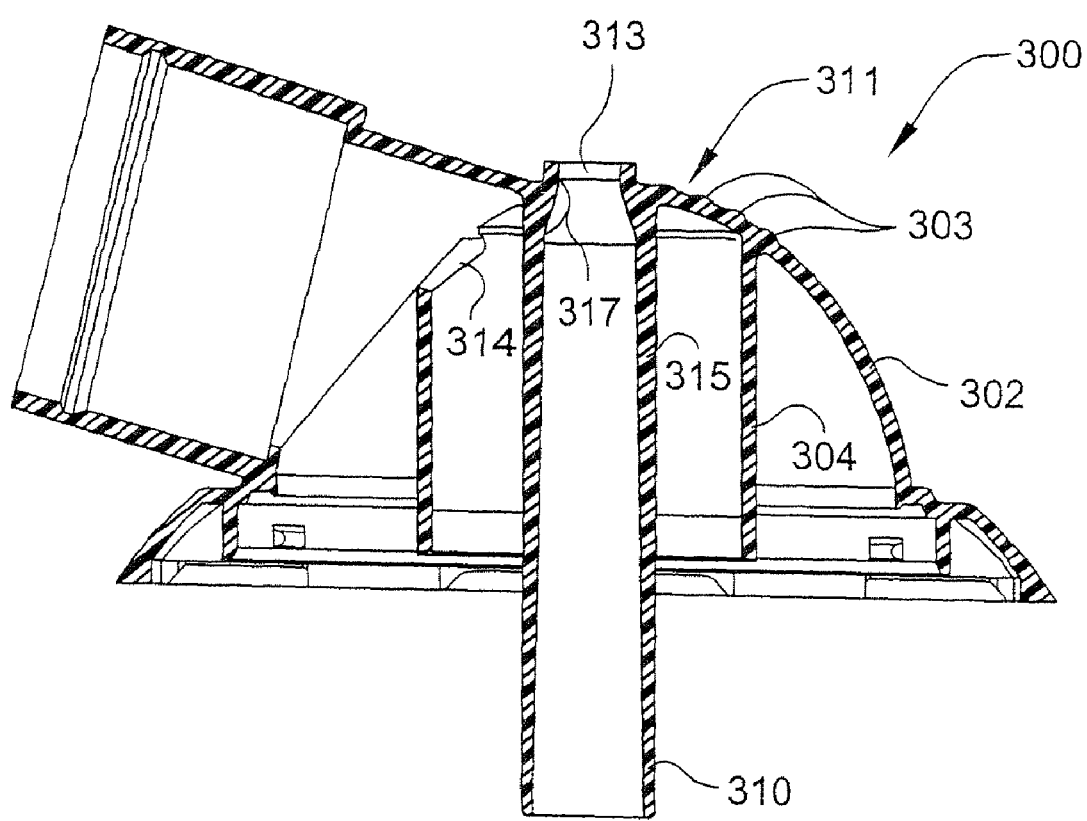
Figure 28F:
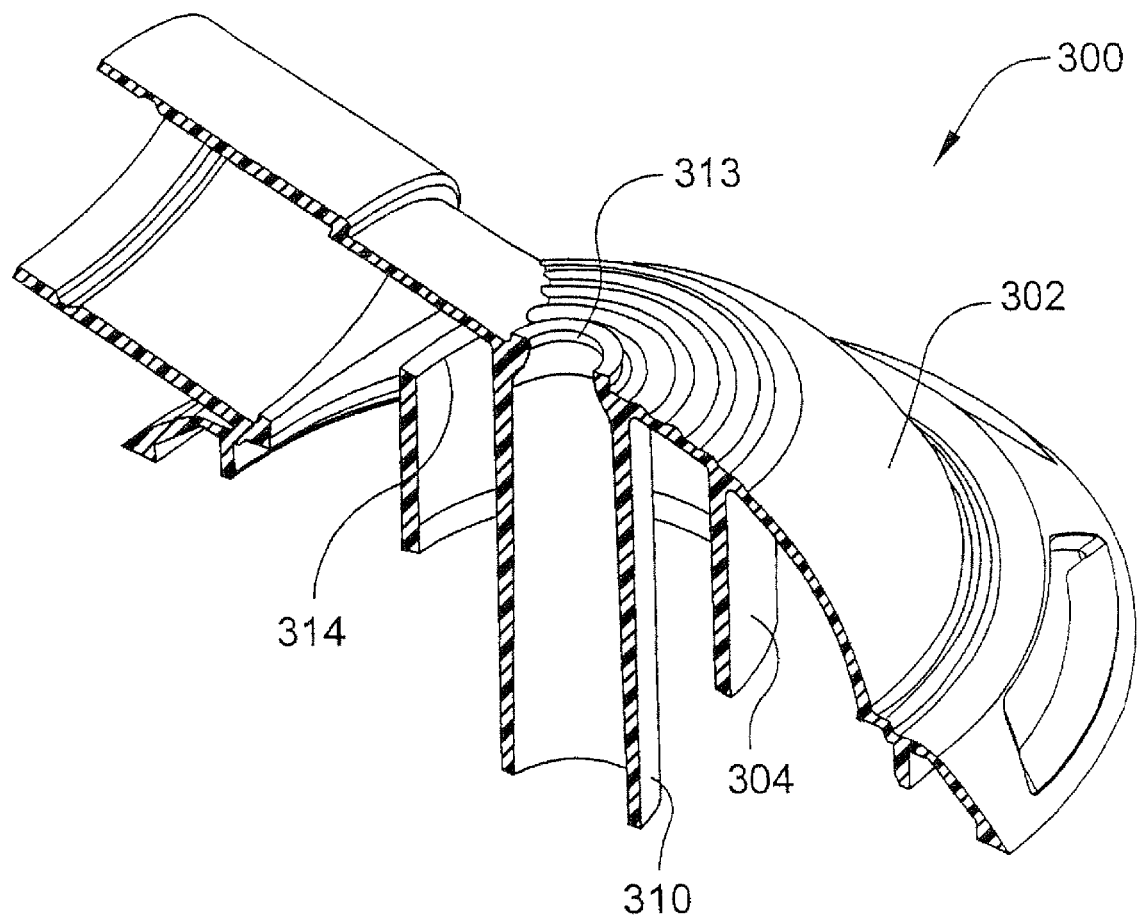
Figure 28G:
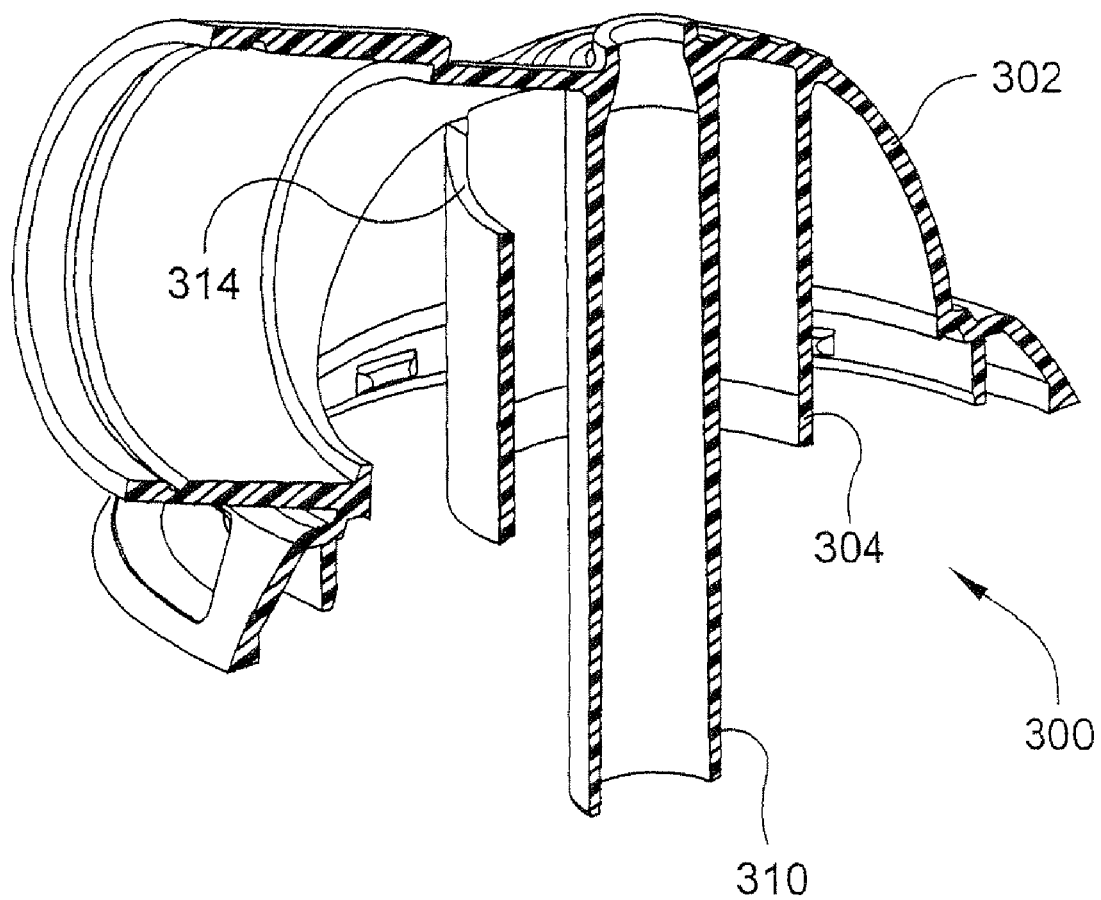
Figure 28H:
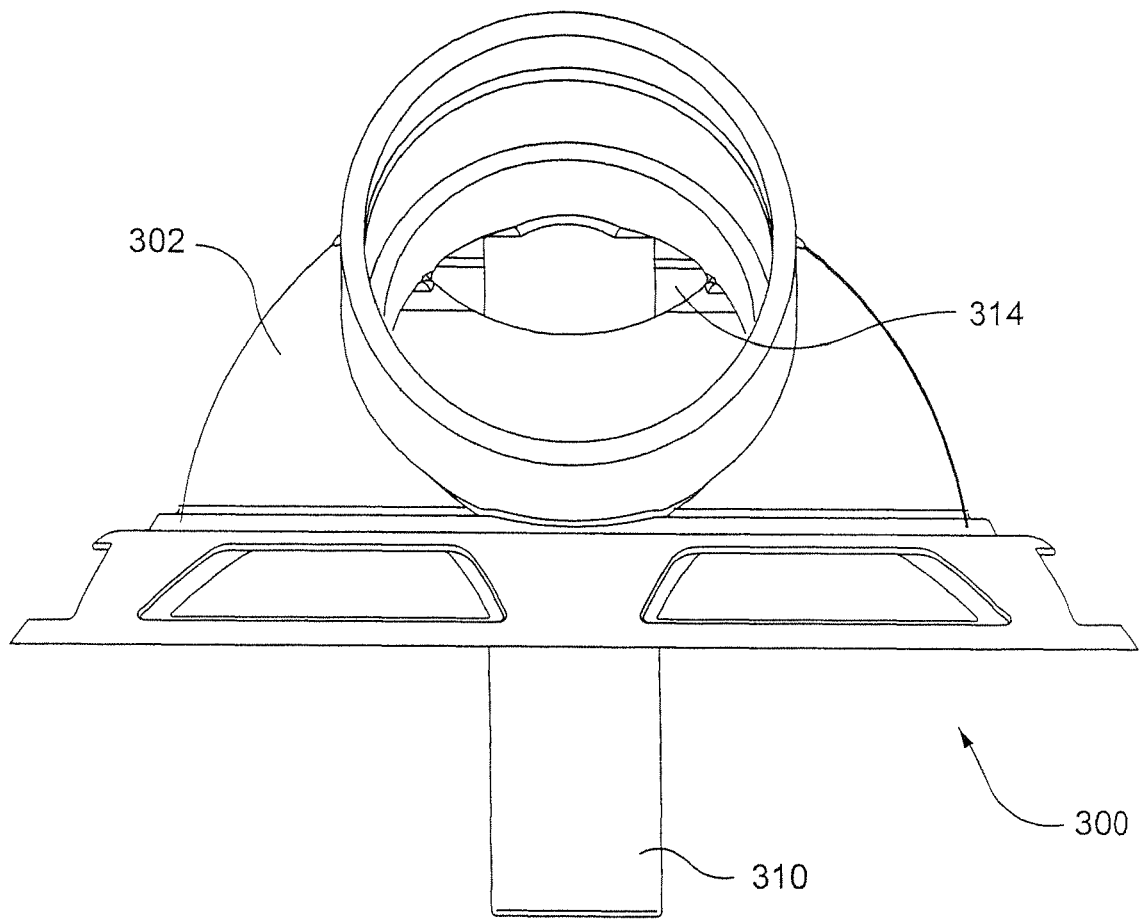

FIGS. 28D-28H illustrate an elbow 300 according to another embodiment of the present invention, which is similar to the embodiment of FIGS. 28B and 28C. As shown in FIGS. 28D and 28E, dome portion 302 includes a plurality of concentric, raised rings 303. As shown in FIGS. 28E-28H, center tube portion 304 extends just outside dome portion 302, but ends before reaching the lower end of the elbow housing which helps with $CO_2$ gas washout. An inner tube 310 extends from the top of the dome portion 302 and past the end of the elbow housing. The top 311 of the inner tube 310 is profiled, as shown in FIGS. 28E-28G. The opening 313 leading to atmosphere is of smaller cross-section than the central portion 315 of tube 310. A transition 317 is formed between the opening 313 and central portion 315. Transition, e.g., may take the form of a tapered conical section. Like the embodiment of FIGS. 28B and 28C, central tube 302 includes an aperture 314 to allow the flow of gas from the air delivery conduit to the inside of tube 302, which helps to lower impedance.

FIGS. 31-A to 31-I illustrate a mask assembly 10 according to another embodiment of the present invention. FIG. 31-A is a front view of the mask assembly 10, while FIG. 31-B is a side view of mask assembly 10. The illustrated reference numbers denote components or parts that have been described in relation to one or more embodiments described above, e.g., FIG. 1.

Mask assembly 10 includes a swivel elbow 16' that is more specifically discussed in relation to FIGS. 31-C-31-F. Elbow 16' includes an inlet conduit 18 (FIG. 31F) having a hose end 18a with a plurality of resiliently deformable tabs 18b that are structured to allow selective attachment to and detachment from a swivel 76. Each tab 18b includes a radially extending protrusion 18c that locks in place within an interior of groove 76a of swivel 76. FIG. 31-E shows the assembled position. The elbow 16 is preferably made from a polyester, e.g., natural POCAN®, a Bayer product, although other materials are possible. The swivel 76 may be made of clear polycarbonate, although other materials are possible. This assembly allows for removal of the hose (not shown) without compromising the integrity of the frame. The internal geometry and functioning of the dome portion of elbow 16' is similar to or the same as that described above or in relation to FIGS. 28D-28H. Elbow 16' may be used in conjunction with anti-asphyxia valve member 34', as shown in FIGS. 31-G to 31-I, whose function is similar to the member 34 described in relation to FIGS. 29-31.

FIG. 32 illustrates a headgear clip 106 according to one embodiment of the present invention. The headgear clip 106 includes a first end 108 for engagement with headgear clip receptacle 24 shown in FIGS. 1 and 2 and a second end 110 for engagement with a headgear strap of headgear assembly. The first end 108 includes first and second arms 112 which may be flexed toward one another in the plane of the paper so as to squeeze into receptacle 24. The receptacle 24 includes an appropriate protrusion or catch 114 (FIG. 1) in a locked position. To unlock the arms 112 from the catch 114, each receptacle 24 includes a pair of opposed arm members 116 which may be pressed toward one another to thereby compress the arms 112 towards one another, thereby placing the headgear clip 106 in a position such that it can be removed from the outrigger 22 and the receptacle 24. The geometry of clips 106 allows them to spring out of receptacles 24 when opposing arms 116 of receptacle are pressed. Each headgear clip 106 includes a central leg 118 including a groove 120 which is designed to receive a protrusion 122, shown in FIG. 2. FIG. 33 is a front perspective view of the headgear clip 106, while FIG. 34 is a rear view of the headgear clip 106. Of course, different headgear clip and clip receptacles can be used instead.

Figure 34A:
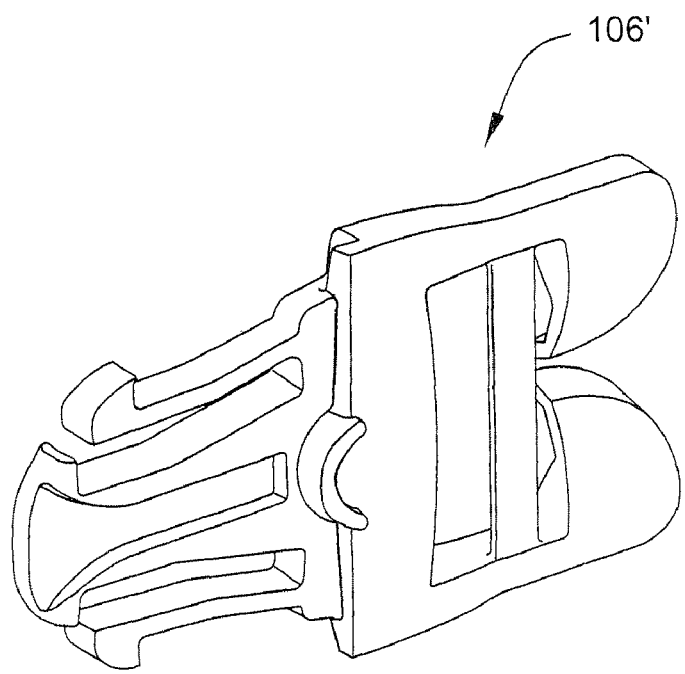
FIGS. 34A and 34B illustrate front and rear perspective views of a headgear clip according to another embodiment of the present invention.
Figure 34B:
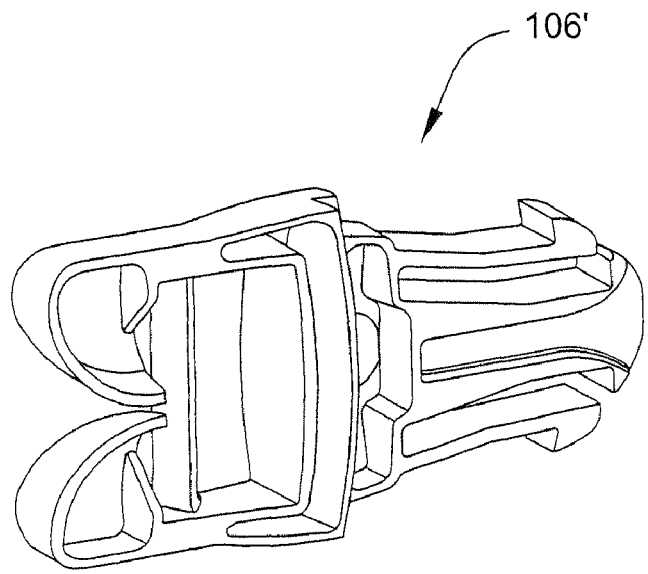

FIGS. 34A and 34B illustrate another embodiment of a headgear clip 106' which is similar to the clip 106 shown in FIGS. 32-34. Several changes have been made which may reduce manufacturing costs, facilitate manufacture, and/or enhance performance.

Figure 35:
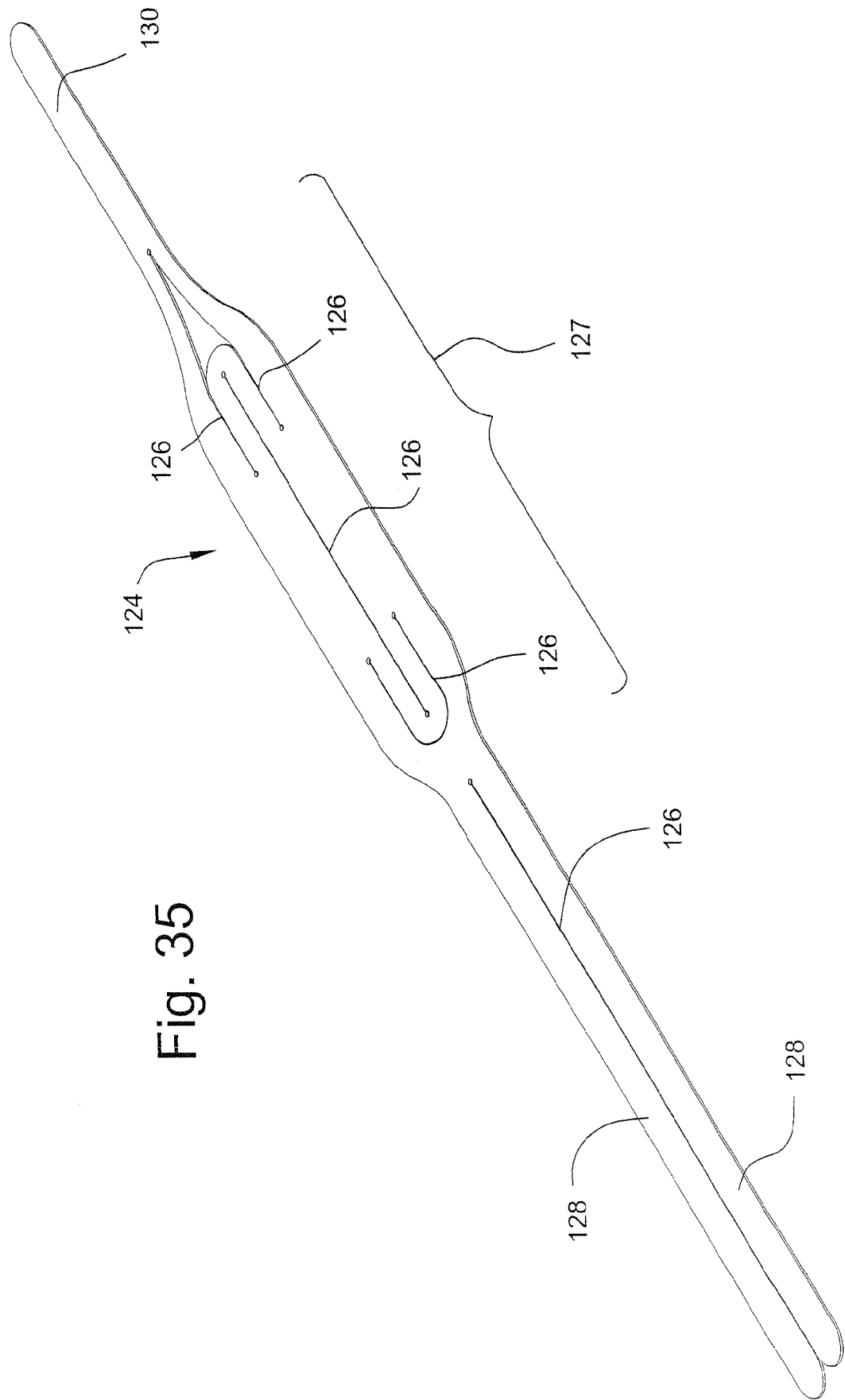
FIG. 35 illustrates a perspective view of headgear according to one embodiment of the present invention.

FIG. 35 illustrates a first embodiment of headgear 124 according to the present invention. Headgear 124 may be manufactured by starting with a substantially flat piece of appropriate material, such as polyester loop material, Breathoprene®, leather, cloth, plastic, etc., and then cutting, scoring or weakening the headgear along predetermined cut lines 126 whereby the headgear 124 may be repositioned to approximate the shape of the patient's head. The headgear 124 may include side straps 128 and front strap 130. Side straps 28 may be created with a single slit 126. Also, in this example, main body 127 of strap has an appropriate amount of slits, e.g., 2-5 slits or more, to optimize coverage and stability of the headgear 124 or patient's head. Generally speaking, each of slits 126 expand in use to form a plurality of open spaces 126', when the headgear is placed on the patient's head.

Figure 36:
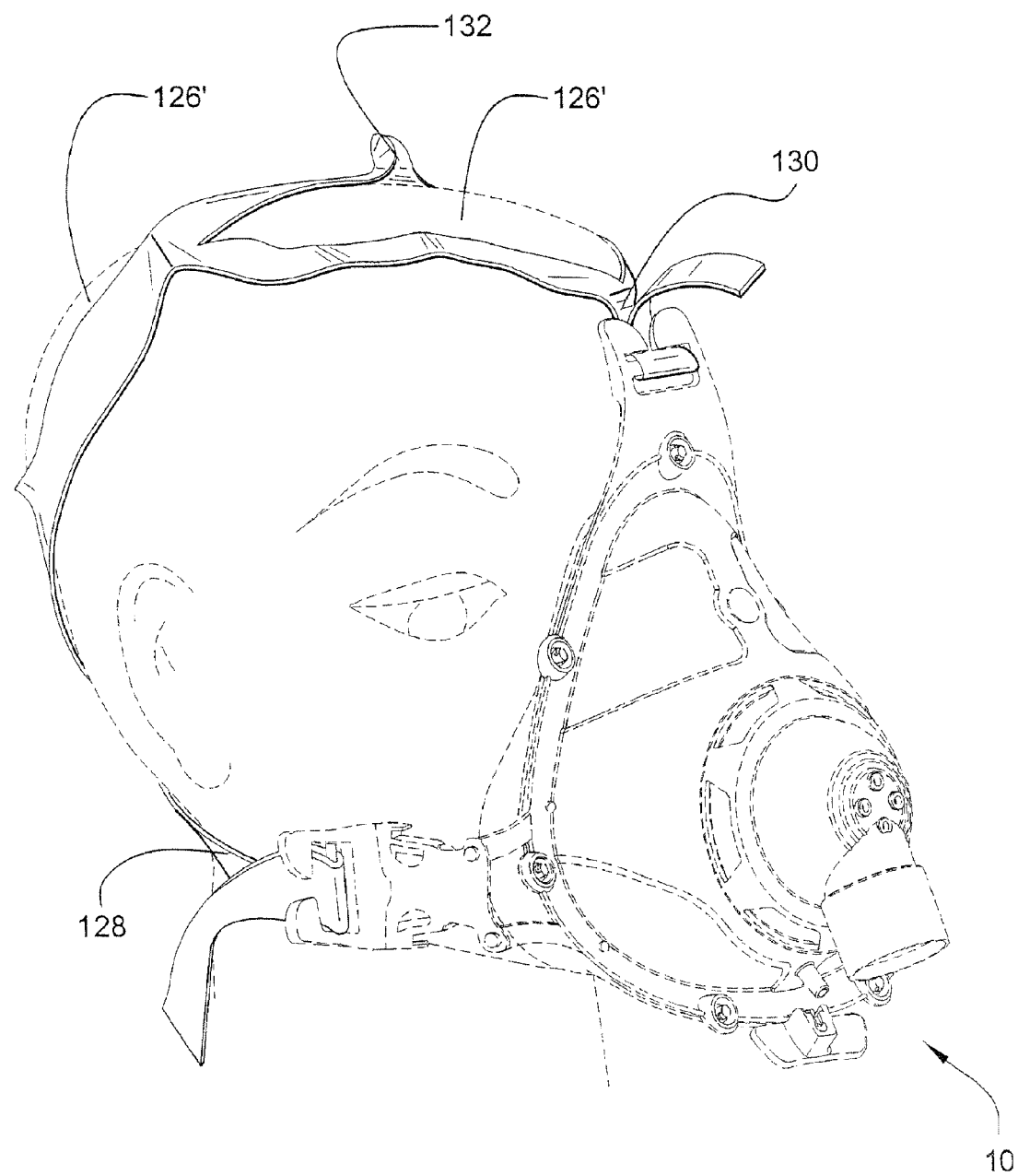
FIG. 36 is a front perspective view of the headgear of FIG. 35 in position on a human head.
Figure 37:
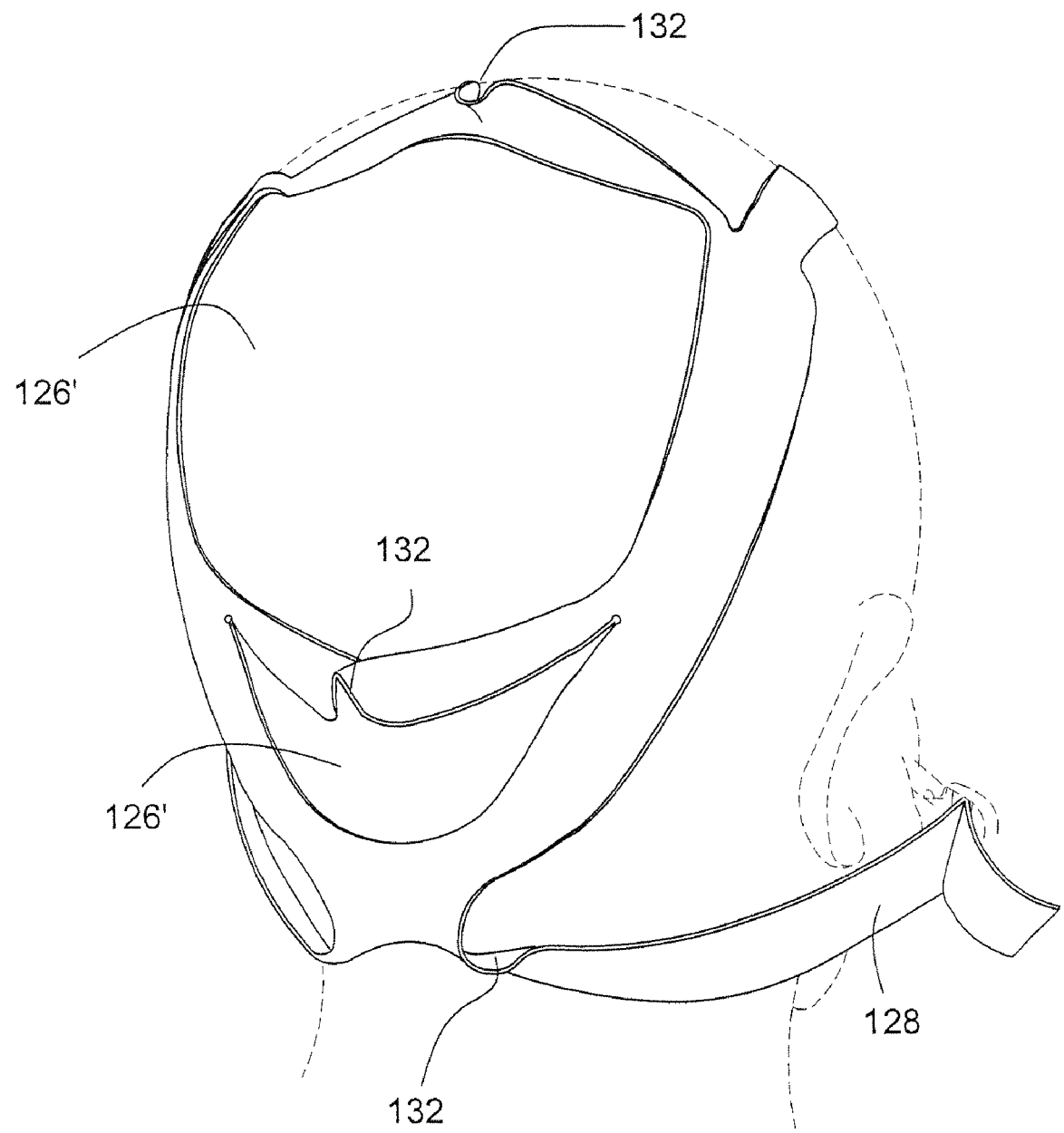
FIG. 37 is a rear perspective view of the headgear of FIG. 35 on a human head.

The positioning of the headgear 124, including the side straps 128 and front strap 130, in relation to the mask assembly 10 and the patient's head is shown in FIG. 36. FIG. 37 illustrates a rear perspective view of the patient's head with the headgear 124 provided thereto. This position cups the occiput of the head to thereby create stability. As can be seen from FIGS. 36 and 37, the headgear includes a plurality of fold lines 132 which are created due to repositioning of the headgear 124 from the position shown in FIG. 35 to the position shown in FIGS. 36 and 37. These predetermined fold lines 132 are acceptable for use in a clinical or hospital environment. However, they do not adversely affect the performance of the headgear 124.

Figure 38:
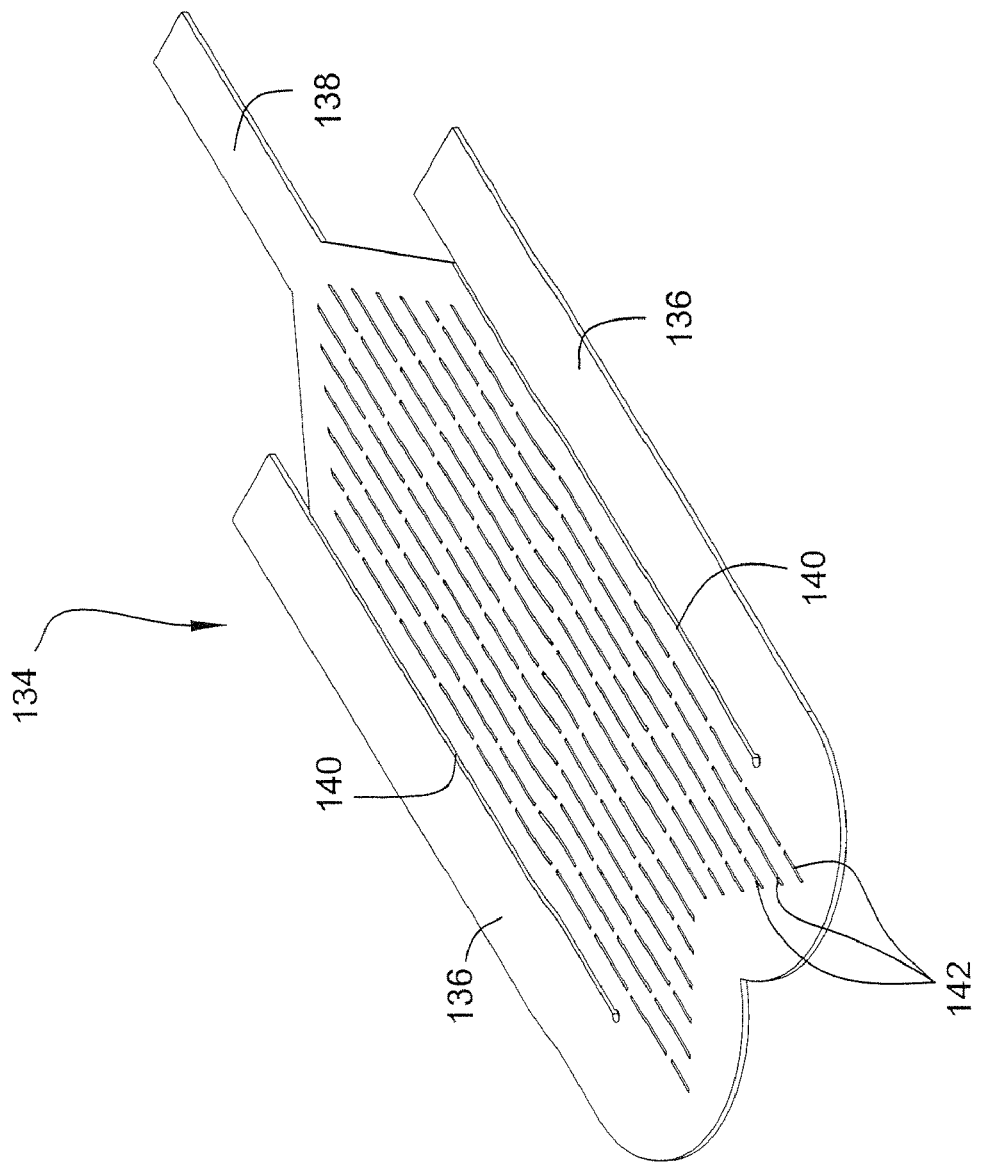
FIG. 38 illustrates yet another embodiment of headgear according to the present invention.
Figure 39:
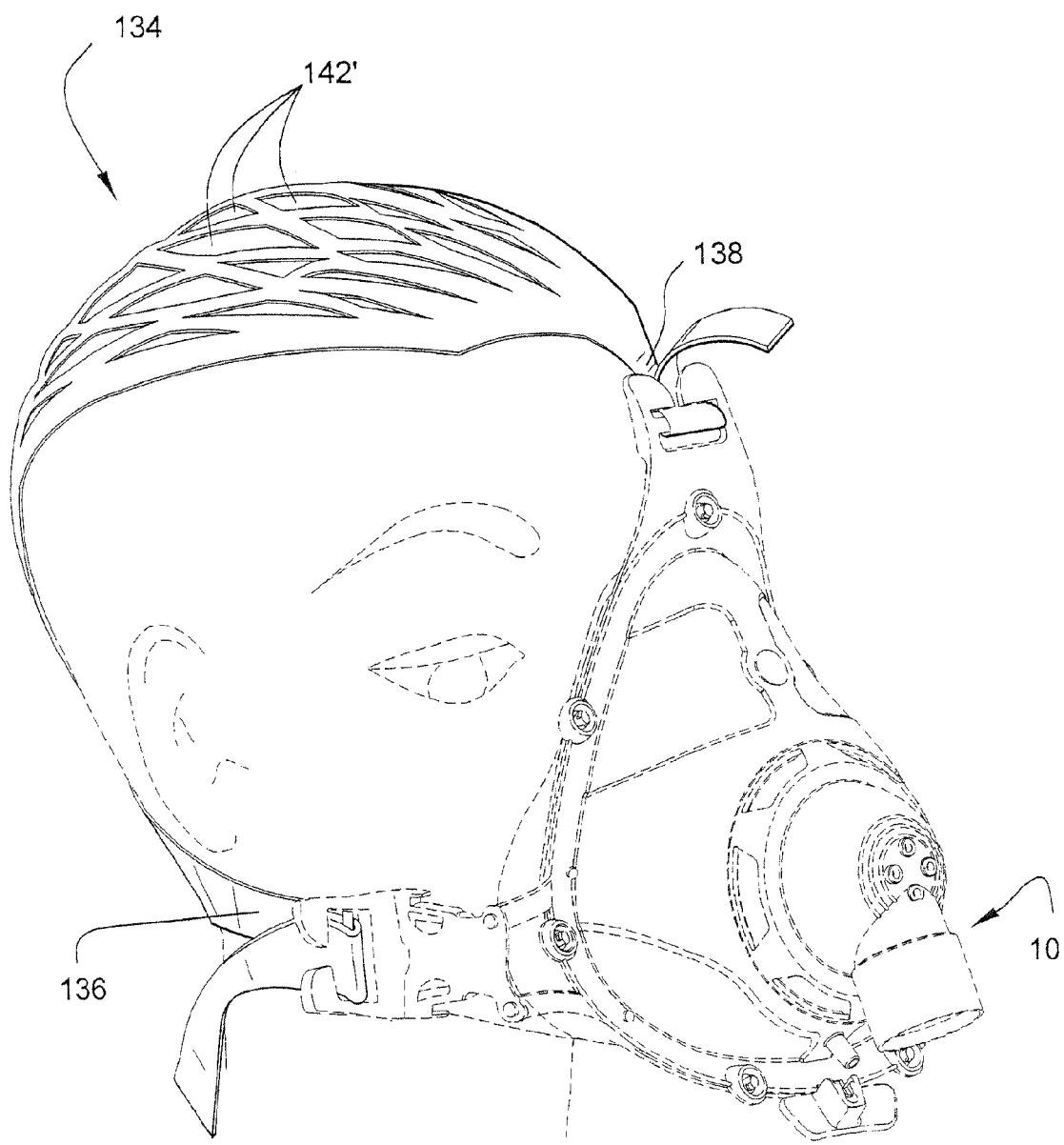
FIG. 39 illustrates the headgear of FIG. 38 from front perspective view on a human head.
Figure 40:
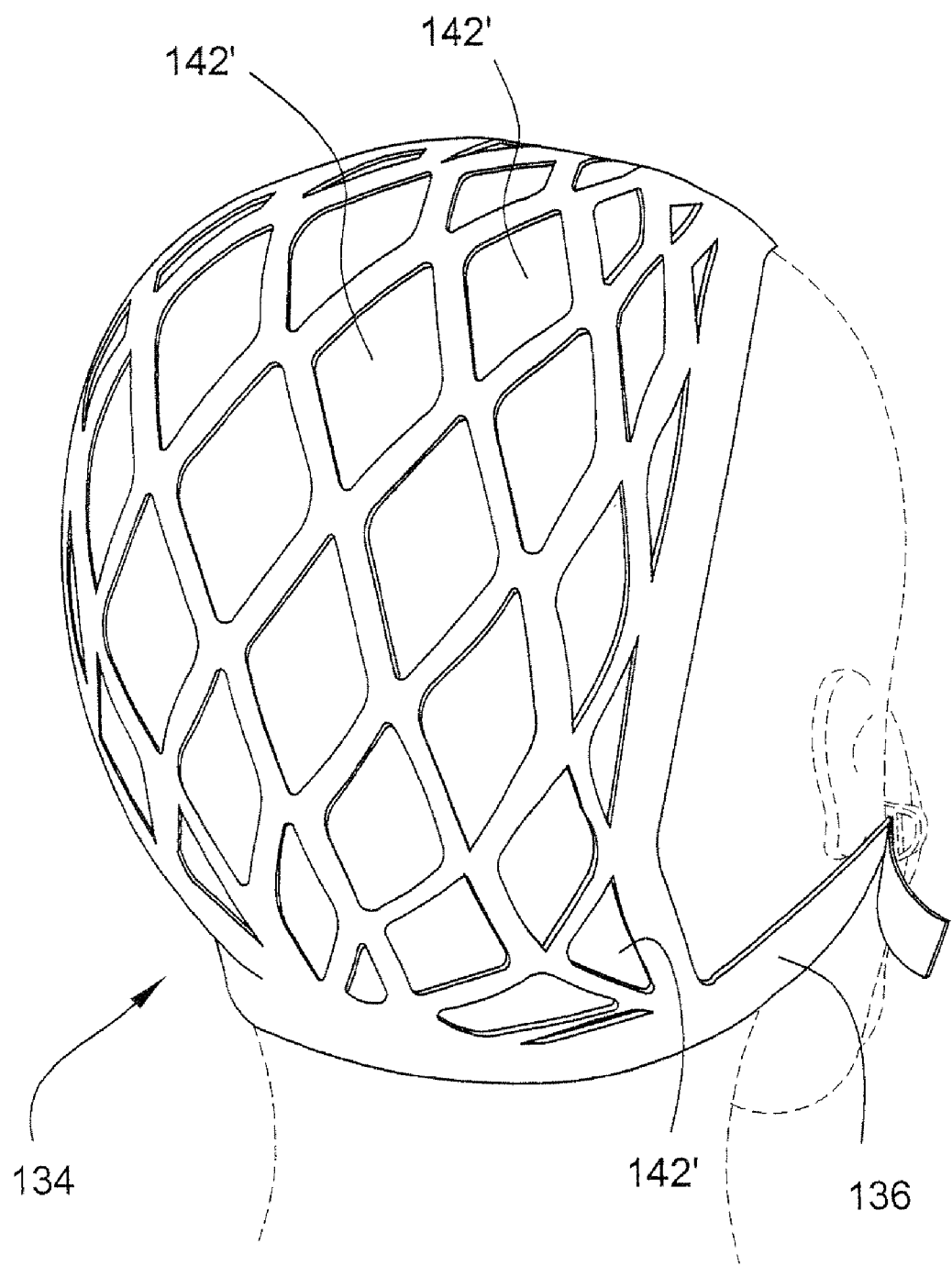
FIG. 40 illustrates the headgear of FIG. 38 in rear perspective view on a human head.

FIG. 38 illustrates a second embodiment of headgear 134 according to the present invention. Headgear 134 includes side straps 136 and front strap 138. Again, the headgear 134 may be manufactured by providing a flat piece of material appropriate for use as headgear on a patient. Each side strap 136 is created by cutting the material along a predetermined cut line 140. The headgear 134 may include a plurality of additional cut lines 142, which creates a net-like configuration on the patient's head, as shown in FIGS. 39 and 40. Each cut line 142 forms an open area 142', to effectively cup the patient's head. Open areas 142' provide for ventilation of the patient's head. Open areas 142' may be in the shape of a polygon, e.g., a triangle or a diamond. Of course, other headgear arrangement may also be used to support mask assembly on the patient's head.

Figure 41:
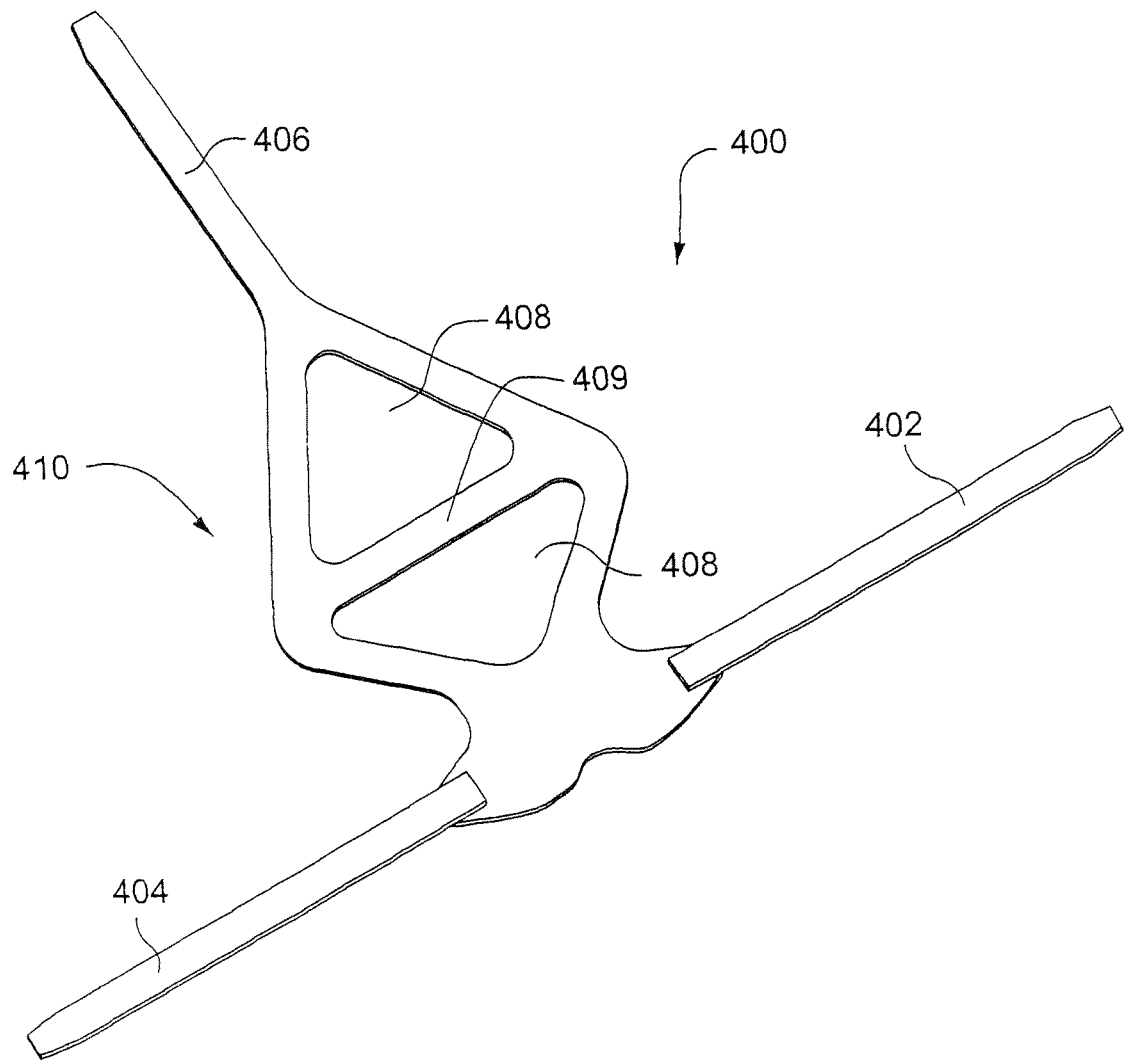
FIG. 41 illustrates a perspective view of headgear according to still another embodiment of the present invention.
Figure 42:
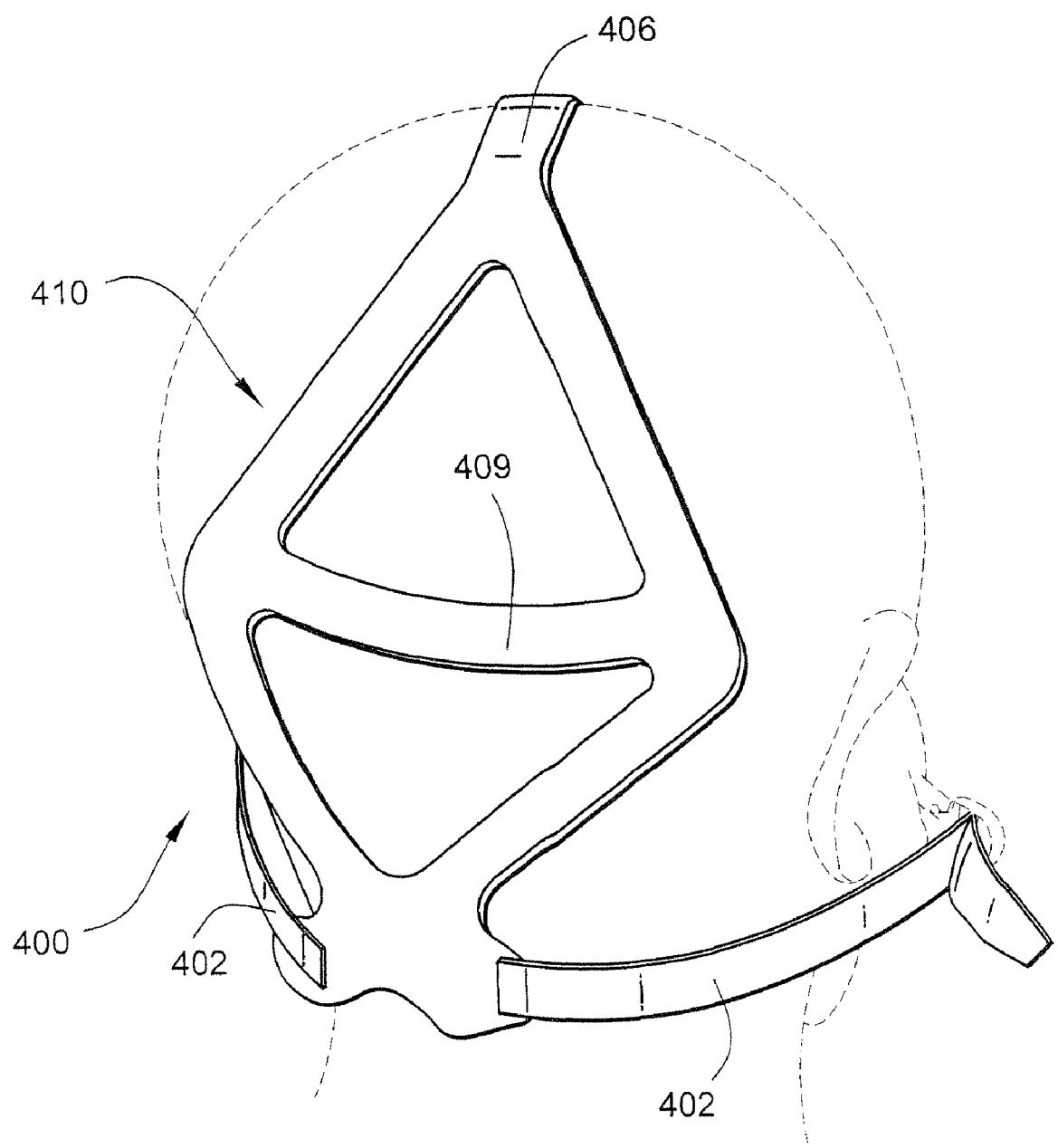
FIG. 42 is a perspective view of the headgear of FIG. 41 on a model patient's head.

FIG. 41 illustrates headgear 400 according to another embodiment of the present invention. Headgear includes side straps 402, 404 and a top strap 406, such that it can be used with the mask shown in FIG. 1. Headgear 400 includes cutouts 408 which help with ventilation and ensure that the headgear is fully retained. Cutouts 408 help headgear to conform to the patient's head. Headgear 400 includes a unidirectional stretch back piece 410. Cutouts 408 may be separated by a divider 409 which may be detachably connected, e.g., via stitching and/or Velcro®, etc. FIG. 42 shows the headgear in position on a model patient's head.

Disposable Characteristics

The mask assembly 10 is intended to be used by a single patient for a limited life span and not reused on further patients. This removes the time and expense of cleaning and reassembling the product. In addition, it removes the difficulties found when components can be lost or assembled incorrectly. For safety reasons, and to avoid cross-infection, the product should have both the function and/or aesthetics of a disposable product in order to alert the user and discourage extended use or use on more than one patient.

The mask assembly has been configured so as to satisfy needs of a clinical or hospital staff. This has been achieved while retaining mask performance desired by patients, which performance includes comfort, minimized leaks, etc., and therefore facilitates patient compliance with treatment.

The mask appears to be disposable from the feeling that it is less durable than a reusable mask. The mask is purposely prone to distortion through handling because it is made from materials that have an expected service life, e.g., of about 7-14 days, and preferably no more than 7 days. In addition, the mask has the characteristic of displaying its "age", e.g., via stress whitening (described in more detail below), and therefore provides an indication to users of the mask system's aging and approaching end-of-life. This aging characteristic is in contrast to prior art disposable masks that typically, without warning, fail in use, for example, when they are stressed while undergoing the procedures of disassembly, washing, assembly or fitting.

The mask system provides a warning to users of approaching end-of-life. In addition, the aging characteristic is intended to serve the safety function of dissuading cross-patient use—the second intended user is disinclined to select or don a used mask. In this way, the aging characteristic facilitates the control of cross-infection and is therefore particularly useful in a clinical multi-patient environment.

Frame

The frame may be formed by polypropylene, polyethylene, PETE, etc., and may be manufactured using a molding process, e.g., injection molding. Preferably, the frame is made of polypropylene with a thin walled section (approximately 0.25-1 mm, preferably about 0.5 mm) that gives it the characteristic of being more flexible than typical multi-use mask frames. Flexibility is desirable because it gives the feeling of being less durable.

In the present embodiment, aging is achieved through the exhibition of "stress whitening." Stress whitening occurs as a result of excessive or repeated deformation of polypropylene and other materials such as polyethylene or PETE. Such excessive and/or repeated deformation will eventually cause the frame material to turn white, ergo the term "stress whitening."

The present embodiment incorporates the characteristic to display stress whitening through an appropriate combination of design and/or components. For example, the wall thickness and stress loading can be designed so as to control stress whitening to occur in those portions of the mask which are most visible to the clinician. For example, the outriggers 22, e.g., legs 68, shown in FIG. 8 may be designed such that they will deform when the headgear is fitted and as such they will exhibit stress whitening with use. As described above, the outriggers 22 include legs 68 which are intended to bend, flex or pivot about axis 72, as shown in FIGS. 8 and 9. Repeated and/or excessive such movement can cause stress whitening. In other embodiments, stress whitening can be used to form a readable text message (e.g., "replace mask" or "discard") which appears only after stress whitening has occurred. Of course, the mask could be designed such that stress whitening occurs in other locations.

Stress whitening will give the visual indication that the mask system has been used. If the mask frame is configured so that the development of stress whitening (e.g., increase in intensity or area displaying stress whitening, or both) occurs as a result of repeated deformation during use, then the mask will also provide a visual indication of aging and approaching end-of-life.

The development of stress whitening will also serve to provide a safety warning to users. By warning of imminent end-of-life, it thereby cautions against use of the mask where it can be expected to fail in use.

Although the mask may exhibit some degree of stress whitening, stress whitening alone will not cause breakage, thereby causing a catastrophic failure. By contrast, the state of the prior art is that masks exhibit a tendency toward unexpected catastrophic failure, e.g., a component snapping, without warning.

A complimentary but independent feature further enhances the frame's disposable characteristic. Some and preferably all components are configured to assemble with a one-way snap action. Once the mask frame/vent and anti-asphyxia valve and cushion components are assembled, they cannot be disassembled without breakage occurring. Further, disposable characteristics of a mask system are that the mask cannot effectively be cleaned as it cannot be disassembled which is a further indication that it is disposable, it is low cost, it has white headgear that is likely to show dirt, grime and wear, and/or it is appropriately labeled.

The frame may include a headgear strap with a self-tensioning feature. This will facilitate a clinical party (i.e., non-patient) fitting of the mask without assistance of the patient. The flexible legs 68 that extend from the frame include attachment points for the lower two headgear straps. The flexibility allows for the legs to fold towards the back of the patient's head and thereby provide extra length to the headgear straps/flexible arms combination when fitting the mask system, thus allowing for the headgear to be located over the patient's head. Then, when the mask and headgear are in place, the legs spring forward, i.e., away from the patient's face, thereby placing some tension to the headgear mask assembly. This helps to avoid the need for cooperation of the patient.

Cushion

The cushion 14 disclosed herein may adopt at least some of the same geometry as is available in the current Mirage® Full Face mask, which includes an upper membrane and an underlying profile. See U.S. Pat. No. 6,513,526 incorporated herein by reference in its entirety.

The cushion 14 is attached to the frame 12 by sandwiching the cushion between the cushion clip 44 and the frame 12. However, the cushion 14 may be attached to the frame 12 using mechanical (e.g., tongue and groove) and/or adhesive techniques.

In an alternative assembly, the cushion can be molded directly to the frame, e.g., via over-molding, with the frame being made of polypropylene and the cushion being made of TPE.

Anti-Asphyxia and/or Back Flow Reduction Valve

The anti-asphyxia valve situated in the swivel elbow 16 functions as both an anti-asphyxia valve and a back flow reduction device. The valve is permanently assembled from three components—the elbow, the valve membrane 34 and the frame 12. To assemble, the membrane 34 is an interference fit with the elbow 16 (see, e.g., FIGS. 23, 23A, 23B) which is then a permanent snap fit to the frame 12. The snap fit includes an undercut on the frame, e.g., groove 66 in FIG. 12, which connects with six tab members 104, for example, on the elbow 16.

When the flow generator is switched off, or in the case of malfunction such as a power cut, the valve membrane 34 sits in the original or unextended position. The edge of the membrane forms a seal against the inner tube 82 of the elbow 16 and thus prevents flow from the mask reaching the inlet conduit 18 and consequently the flow generator. Thus, the valve prevents gas flow back to the flow generator which is particularly useful in circumstances where $O_2$ is ported into the mask. Any $O_2$ that is supplied to the mask cannot reach the flow generator, i.e., the valve acts as an $O_2$ divertor valve (ODV) and removes a potential fire hazard. In addition, see U.S. patent application Ser. No. 10/433,980 assigned to ResMed Limited and incorporated by reference in its entirety.

In the unpressurized state, air reaches the mask through the six slots 102 (FIGS. 23B, 24 and 25) in the elbow 16 which connects with the circular inlet in the frame. Ambient air is channeled between the lower surface of valve member 34 and surface 36 (FIG. 3) of frame 12. Thus, the valve is also acting as an anti-asphyxia device. This embodiment has an advantage over ResMed's anti-asphyxia valve mentioned above in that it closes the flow to the inlet conduit 18. This prevents air from be rebreathed from the inlet conduit 18.

When the flow generator is switched on and pressure is applied, the membrane 34 extends from its original position and forms a seal against the circular inlet (e.g., surface 36 in FIG. 3) of the frame 12. This pressurized air from the inlet conduit 18 can flow around the elbow inner tube 82 and directly through the circular inlet of the frame. The inner shoulder 90 may separate from the end of tube 82, as shown in phantom in FIG. 23A. In this position, the valve member is configured such that it may provide an audible noise, e.g., a whistle. This may provide comfort or a positive feedback signal to the patient/clinician that the device is assembled properly and/or that pressurized gas is being properly channeled. The audible signal, e.g., whistle, can be created by vibrations in a manner similar to that created when playing the reed of a musical instrument. Alternatively, a small gap may be designed to create the whistle effect. The device, e.g., the anti-asphyxia valve, may be arranged such that a noise is created if the system is not correctly assembled, to thereby provide a warning to the user or clinician. In general, the mask can be designed to include or not include noise, depending on preference.

This design achieves a lower profile elbow, which is desirable both for aesthetic reasons and it improves the stability of the mask. Another factor to consider when designing the elbow is the entry impedance of the mask. It is desirable to minimize impedance in order to prevent pressure swings occurring during breaths.

The lower profile elbow is achieved by a number of factors. Firstly, the elbow acts as the housing for the membrane and the valve is placed at the interface of the elbow in the frame. This reduces the number of components that are required (and associated manufacturing costs) as well as removing the bulk of a further interface. Secondly, the inlet conduit 18 is at an angle from the mask of greater than 90°, e.g., 100°-120°. Thirdly, the diameter of the inlet cavity has been increased. This increases the cross-sectional area presented to the inlet flow (and thus reduces the entry impedance) for a given elbow inlet angle.

The valve is physically larger than the existing ResMed anti-asphyxia valve mentioned above to achieve a reduced impedance in the elbow compared to the currently available ODV.

Mask Vent

The mask vent is incorporated in the elbow. Existing ResMed full face masks have their vents incorporated in the mask frame.

Inadvertent leak is virtually zero due to the configuration of the vent and anti-asphyxia valve. This performance is achieved partly by configuring the anti-asphyxia valve to include a relatively soft part, e.g., membrane 34 made, e.g., of silicone, to seal between the frame and the swivel elbow.

When a vented mask is adopted to be used with a ventilator there is a requirement to calibrate the vent. This process typically requires blocking of all the pathways to atmosphere so that the path to atmosphere occurring at the vent may be isolated and thereby characterized.

By putting the vent in the elbow it is relatively easy to block the orifice joining the mask chamber and the elbow downstream of the vent so as to achieve the required isolation. This configuration avoids the difficult to perform blocking of the large path to atmosphere that occurs at the mask aperture, i.e., the mask chamber entry point which receives the patient's face. A plug may be used to block the orifice between the elbow and the mask chamber, but it may be also easily achieved in the clinical setting by placing a finger over the orifice.

This is an advantage in a situation as compared to the prior art, which includes three sizes of frames with a vent in each frame, thereby requiring different tools for each frame/vent for calibration. This embodiment of the invention simply has a single elbow to calibrate for flow, independent of the mask frame size.

The anti-asphyxia valve may be adopted for use in a multiple use full face mask as it is made from silicone where it will be robust, washable and capable of reassembly. The anti-asphyxia valve is then a common part, requiring less inventory and there will be no need to develop a new anti-asphyxia valve for a new face mask.

Frame Port and Port Cap

The frame port cap is configured to meet clinical needs. The port cap is integrated into the cushion configuration, which allows the port cap to be formed at the time of cushion manufacture, thereby eliminating the need for separate manufacturing. This allows for a one molding operation to make the cushion and mask components. It also allows the port cap to pass through manufacturing and distribution chain as one component with the cushion. This simplifies handling and inventory logistics, and reduces manufacturing and warehousing costs.

The location of the port cap in relation to the cushion are such that when the cushion is attached to the frame, the port cap is conveniently positioned to be attached to the frame port.

These features are particularly welcome in the clinical setting where there is need to frequently attach and detach a port cap (e.g., when attaching or detaching lines to the frame port or for the measurement of treatment pressure, servo control of flow generator or delivering treatment gas such as $O_2$). With the port caps attached to the cushion it is always conveniently available to be attached to the frame port.

In addition, the port cap has one or more large grip wings to facilitate convenient manipulation. A problem identified by the inventors is that the typical small port caps supplied with prior art masks are an annoyance to the regular clinical user. Grip wings may be supplied for a group of port caps or individually associated with each port cap.

Preferably, the port and port cap are located at the bottom of the mask so as to avoid interference with other components of the mask assembly, as described in U.S. Pat. No. 6,439,230, assigned to ResMed Limited and incorporated herein by reference in its entirety. Of course, the port and port cap could be located in other convenient positions around the mask frame. In addition, multiple ports and caps could be provided to the same mask.

Headgear

The headgear performs in a manner that contributes to the systems aging characteristic. This performance is achieved by use of material that gives a display of its accumulation of grime, i.e., soiling. The chosen material accumulates and displays its accumulation of grime, e.g., by visual and tactile signals. Preferably, the headgear when first brought into service is generally white or other a light shade of color.

In addition to the objective visual signal, the aging characteristic achieved through the perception of soiling will provide a useful psychological signal. Potential users will not want to don a seriously soiled headgear while a clinical staff will be prompted to choose a fresh mask system for patients especially when fitting a patient new to the mask.

Grime may be attributable to skin, sweat, oils, facial secretions, etc. The aging characteristic may be incorporated into the headgear and/or mask frame in such a way that the headgear or mask frame exhibits age due to exposure with such sources of grime. In other words, grime may provide a visual indication on the headgear frame to signal the clinician that it is time to replace the mask system.

In another alternative, the aging characteristic can be provided with headgear which frays or otherwise decomposes after repeated use beyond the nominal set limits.

The headgear strap configurations allow for more consistent location of straps under the patient's ear and thereby avoid the annoying contact of the strap with the lower portion of ear.

Headgear may be configured from a die cut side piece, e.g., a laminated material which in its unassembled form is shaped to minimize waste and thus reduce costs/control. The waffle pattern, when expanded, will allow for expansion and correct placement on the head. This design achieves a three-point fitting configuration. A two-dimensional piece of material is used to achieve a three-point headgear which achieves the performance of a four or five-point headgear. This allows for placement of the top strap to follow a line which is low on the ears and resembles what is achievable with a four strap headgear, which allows for desirable distribution of forces but with the convenience of one top strap.

Headgear Clip

The headgear clip mechanism includes a housing which incorporates release tabs and that is formed as part of the frame. A headgear clip is spring-fit into the receptacle on one side and acts as an attachment point for the headgear on the other side. The headgear attachment side has two slots. The first slot 111 (FIGS. 32-34), closest to the mask, is a fully formed slot through which the headgear is threaded. The second slot 113, closest to the headgear has large shaped tabs 115 formed on one side, between which a gap G exists. The gap G and the tapered shape of the tabs allows the headgear to be connected through the second slot by pulling down through the tabs. This assembly technique is much simpler than threading.

Further benefits of the clip design are that the clip is very large which makes it easier for manipulation. The tabs 116 (FIG. 1) to release the clip are operated from the top and bottom which facilitates the user configuration. Further, the tabs 116 form part of the frame, rather than part of the clip. Therefore, the tabs do not slide with the clip which makes single handed operation easier.

The headgear clip may include a ladder lock and lead-in design. The headgear clip may serve as a quick release mechanism, i.e., the sprung release of the clip is a quick release mechanism. It has an exaggerated tactile finger tab to make it easier to find should there be a need for rapid response quick release.

The headgear clip allows for quick manual assembly which serves both as a manufacturing aid and a benefit to customers as it allows for a presentation of a fully assembled product and benefits a clinical setting as it allows for quick reassembly when required.

Summary—General Effects of Preferred Embodiments

Hospital and fully featured hospital use is characterized by several factors: single patient use, clinician requirements, and/or a desirability to discourage reuse.

Ease of fitting may be achieved via a headgear spring/outrigger design. Ease of assembly prevents incorrect assembly and protects from interference and tampering. Disassembly is prevented between the cushion and frame since they are permanently connected. The elbow is snapped to the frame via a one-way snap, which cannot be disconnected without destroying or breaking the elbow and/or frame. The ports cap is formed as an integral portion of the cushion, thereby preventing its loss or detachment.

The mask is designed to discourage reuse because there is no method of efficient cleaning that is possible as there is no access to the anti-asphyxia valve. Moreover, the mask displays evidence of use, e.g., via stress whitening and distortion under force. Stress whitening may be achieved by some combination of material, wall section dimensions, geometric form and/or use of a yielding flexible part. The materials may include polypropylene, polyethylene or PETE, and may be made by molding, such as injection molding or they may be vacuum formed. The stress whitening may be provided via the outriggers although the top support of the frame, the forehead support, port cap, etc. may also be used to exhibit stress whitening. Moreover, a living hinge could also be used to display evidence of use.

Other alternatives to stress whitening include snapping via a one-way connection, to thereby prevent or inhibit reuse. Other possible indicators include exposure to air, $O_2$ or grime, exposure to condensation (moisture indicators), $CO_2$ detectors, etc.

The mask frame is intended to look disposable and non-durable via one or more of the following criteria: material choice, color (headgear is white, frame could also be white). Headgear could be cardboard with a plastic interior, material thickness, simple construction and/or an exposed construction method. The mask feels disposable, e.g., the frame is flexible and will deform with predetermined and/or repeated application of force.

The port and cap structure is advantageous since it is an integral component with the cushion, and cannot come apart from the assembly. Therefore, the port cap cannot be lost since it is attached to the cushion. This allows for lower manufacturing cost as the cushion and cap are one component rather than two. This also prevents cross-patient use.

The port cap includes one or more large grip tabs, which are easier to operate, particularly for clinicians. The large grip tabs allow for easy location. The grip tabs are visible, and show whether they are on or off, and their operation is obvious to inexperienced users, thereby avoiding the error of cap being left off.

The port cap is self-locating, meaning that the cap stays close to the port when removed, but requires little dexterity to place the port cap back onto the port, and does not require visual affirmation since affirmation can be provided via tactile means.

The port cap is positioned at the bottom of the frame, which is near the nares, thereby providing an advantage for the supply of oxygen. The port cap is not susceptible to being disturbed by movement of the patient's head. The port cap allows an air inlet tube and swivel to rotate freely. The most common position of the air inlet tube is always away from the bottom, and the smaller tubes can be easily routed along the tube as commonly occurs.

Alternative embodiments include a living hinge cap molded from the frame. This had the advantage of displaying evidence of use, e.g., stress whitening.

In still further embodiments, a barbed head may be pulled through the frame or cushion wall, with the barbed head sealing against the frame. The port cap can be molded with a thin strap directly to either the cushion or the frame. The port cap may be sandwiched between the cushion and frame, which decreases the chances that the port cap can be lost. The port cap can be co-molded with the frame. The port cap can be molded integrally with the anti-asphyxia valve or the vent or any elastomeric component. The port cap can be purposely made to break off with use to display hospital use, to thereby convey the disposable nature of the mask. Alternatively, the port cap may develop a cut end with overuse.

The above described self-tensioning feature facilitates fitting of the mask assembly to the patient. The self-tensioning spring provides elasticity when required, e.g., when initially taking the headgear over the head. This allows a larger degree of opening when fitting. In addition, it could be used with non-elastic headgear, and is particularly suitable for a third party/clinician fitting.

The self-tensioning aspect provides a spring to give some tension when initially fitted before tightening the straps. This prevents the straps from simply flopping and prevents the tangling of straps.

The self-tensioning aspect provides a visual indication that straps are not tight or tensioned. In a further embodiment, a tension indicator may be provided, which displays the amount of tension either by angle (this could be whilst on the patient) or with permanent deformation for clinical evaluation after patient use.

The self-tensioning aspect keeps the headgear from tangling away from the patient, and may include broad attachment points, which maintain strap alignment and does not twist.

The self-tensioning aspect also may display evidence of use, e.g., via stress whitening upon use. Evidence of use may also be demonstrated via use of various combinations of material, thickness and geometric form. The outriggers may also creep with use to a point at which it does not regain form after patient use.

In alternative embodiments, the outriggers could be used on reusable masks. The headgear clips can be snapped into use under certain tension. This has an advantage of maintaining form and a larger degree of opening but does not act as a spring. This may give a strong indication of use by not maintaining form after first use, and encourage the product to be thrown away after single patient use.

The outrigger assembly may include a living hinge, which may be advantageous from the aspect of keeping form in larger degree of opening but does not act as a spring. This would give a strong indication of use by not keeping form after first use, and encourage the product to be thrown away after single patient use. This would show use at the hinge point.

In other alternatives, a self-tensioning spring could be attached to headgear rather than the frame. In addition, a tension indicator may display the amount of tension either by angle, whilst on the patient, or with permanent deformation for clinical evaluation after patient use. The hinge could be part of a cushion or a captive part of the cushion frame interface rather than part of the frame. The hinge could be incorporated into the designs of other existing disposable and reusable masks.

Headgear according to the present embodiments include several features and/or advantages. For example, the headgear is manufactured using a strip design, which is the lowest volume for manufacture, meaning low wasted or inefficient use of materials. The design expands from a one-dimensional strip in manufacture to a three-dimensional cup in use.

The process for making the headgear can be from a single stamp or slit within the perimeter of the strip. The headgear need not cover much of the head, is cool and is unobtrusive. The headgear achieves a simple yet stable design. Different colors can be provided on each side of the material for a visual clue as to the part which is facing towards and away from the patient, which allows for ease of assembly and non-tangling of the strap components.

Alternative materials for the headgear include foam, silicone and/or breathable materials. The material can be elastic or non-elastic, of varying stiffnesses in different directions. Further, separate strips can be joined with varying stiffnesses. This will allow fine tuning of the elasticity of individual straps of the headgear. Various stiffnesses can also be achieved by sticking VELCRO® tapes over part of the headgear or by providing cross-stitching, etc. The headgear can also be manufactured by forming a number of individual components, laying them next to each other and then joining them via stitching, gluing, etc.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the invention.

The invention claimed is:

1. A mask assembly for delivering a flow of breathable gas to a patient, comprising:
    a frame defining a breathing chamber;
    an elbow connected to the frame, the elbow comprising an inlet conduit configured to deliver the flow of breathable gas to the frame, a cylindrical inner tube, a wall member surrounding the cylindrical inner tube, and at least one aperture adjacent the wall member; and
    a valve member provided between the frame and the elbow, the valve member being disposed between the wall member and the cylindrical inner tube, wherein the valve member is configured to allow breathing of ambient air through the at least one aperture of the elbow into the breathing chamber and to prevent a back flow of gas into the inlet conduit of the elbow in an absence of the flow of breathable gas and to permit the flow of breathable gas into the breathing chamber when delivered by the inlet conduit.

2. A mask assembly according to claim 1, wherein the cylindrical inner tube is in communication with atmosphere and the elbow comprises a dome that supports the tube, and wherein any back flow of gas is passed through the cylindrical inner tube and not the inlet conduit in the absence of the flow of breathable gas.

3. A mask assembly according to claim 2, wherein the cylindrical inner tube communicates with the atmosphere via a profiled end that is smaller towards atmosphere.

4. A mask assembly according to claim 3, wherein the cylindrical inner tube communicates with the atmosphere via at least one aperture in the dome.

5. A mask assembly according to claim 4, further comprising a duck bill valve provided in the least one aperture.

6. A mask assembly according to claim 1, wherein the valve member is structured to separate from the cylindrical inner tube when the flow of breathable gas is delivered by the inlet conduit to an aperture of the frame.

7. A mask assembly according to claim 1, wherein the valve member creates an audible indicator during the flow of the breathable gas.

8. A mask assembly according to claim 7, wherein the audible indicator comprises a whistle.

9. A mask assembly according to claim 1, wherein the valve member is connected to the elbow by an interference fit.

10. A mask assembly according to claim 9, wherein the valve member is configured to create an audible indicator when correctly assembled to the elbow.

11. A mask assembly according to claim 9, wherein the valve member is configured to create an audible indicator when incorrectly assembled to the elbow.

12. A mask assembly according to claim 9, wherein the valve member comprises a circular main body comprising an outer shoulder configured to engage the wall member.

13. A mask assembly according to claim 12, wherein the valve member comprises an aperture defining an inner shoulder, the inner shoulder sealing against the cylindrical inner tube in the absence of a flow of breathable gas.

14. A mask assembly according to claim 13, wherein the inner shoulder is connected to the outer shoulder by a V-shaped intermediate portion.

15. A mask assembly according to claim 1, wherein the valve member is made of a elastomeric material.

16. A mask assembly according to claim 15, wherein the valve member is made of silicone.

17. A mask assembly according to claim 1, wherein the inlet conduit is at an angle to the frame of greater than 90°.

18. A mask assembly according to claim 17, wherein the inlet conduit is at an angle to the frame of about 100°-120°.

19. A mask assembly comprising:
a frame;
an elbow provided to the frame and including an inlet conduit; and
a valve member provided between the frame and the elbow, the valve member being configured to allow breathing of ambient air and to prevent back flow of gas towards the inlet conduit of the elbow in an unpressurized state, wherein the elbow includes a center tube portion and an inner tube suspended from a dome portion of the elbow.

20. A mask assembly according to claim 19, wherein the inner tube is in communication with atmosphere and any back flow is guided through the inner tube and not the inlet conduit in the unpressurized state.

21. A mask assembly according to claim 20, wherein the valve member is structured to separate from the inner tube during operation in a pressurized state, to thereby allow pressurized gas to enter an aperture of the frame.

22. A mask assembly according to claim 19, wherein the elbow includes at least one inlet slot structured to allow ambient air to be channeled between the valve member and the frame for supply to the patient, when operating in the unpressurized state.

23. A mask assembly according to claim 19, wherein the valve member creates an audible indicator during operation in a pressurized state.

24. A mask assembly according to claim 23, wherein the valve member creates the audible indicator upon proper assembly.

25. A mask assembly according to claim 23, wherein the valve member creates the audible indicator upon improper assembly.

26. A mask assembly according to claim 19, wherein the inner tube communicates with the atmosphere via a profiled end that is smaller towards atmosphere.

27. A mask assembly according to claim 19, wherein the center tube portion includes an aperture near its connection to the dome portion and is generally aligned with the inlet conduit.

* * * * *